US011510600B2

(12) United States Patent
Valdes et al.

(10) Patent No.: US 11,510,600 B2
(45) Date of Patent: Nov. 29, 2022

(54) METHOD AND APPARATUS FOR QUANTITATIVE AND DEPTH RESOLVED HYPERSPECTRAL FLUORESCENCE AND REFLECTANCE IMAGING FOR SURGICAL GUIDANCE

(71) Applicant: The Trustees of Dartmouth College, Hanover, NH (US)

(72) Inventors: Pablo Valdes, Phoenix, AZ (US); Frederic Leblond, Montreal (CA); Keith D. Paulsen, Hanover, NH (US); Brian Campbell Wilson, Toronto (CA); David W. Roberts, Lyme, NH (US); Michael Jermyn, Longueuil (CA)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 854 days.

(21) Appl. No.: 15/044,097

(22) Filed: Feb. 15, 2016

(65) Prior Publication Data

US 2016/0278678 A1 Sep. 29, 2016

Related U.S. Application Data

(63) Continuation of application No. PCT/US2014/051356, filed on Aug. 14, 2014, and a
(Continued)

(51) Int. Cl.
*A61B 5/1455* (2006.01)
*A61B 5/1459* (2006.01)
(Continued)

(52) U.S. Cl.
CPC ...... *A61B 5/14556* (2013.01); *A61B 1/00009* (2013.01); *A61B 1/00165* (2013.01);
(Continued)

(58) Field of Classification Search
CPC ..... A61B 5/4836; A61B 5/7264; A61B 6/032; A61B 6/037; A61B 6/4417; A61B 6/481;
(Continued)

(56) References Cited

U.S. PATENT DOCUMENTS

| 5,109,276 A | 4/1992 | Nudelman et al. |
| 5,810,731 A | 9/1998 | Sarvazyan et al. |

(Continued)

FOREIGN PATENT DOCUMENTS

| JP | 2006-195240 A | 7/2006 |
| KR | 10-2011-0097030 A | 8/2011 |

(Continued)

OTHER PUBLICATIONS

Konecky et al., "Spatial frequency domain tomography of protoporphyrin IX fluorescence in preclinical glioma models", Journal of Biomedical Optics, vol. 17, Issue 5, pp. 1-7, May 2012. (Year: 2012).*

(Continued)

*Primary Examiner* — Katherine L Fernandez
(74) *Attorney, Agent, or Firm* — Lathrop GPM LLP

(57) ABSTRACT

An imaging system, such as a surgical microscope, laparoscope, or endoscope or integrated with these devices, includes an illuminator providing patterned white light and/or fluorescent stimulus light. The system receives and images light hyperspectrally, in embodiments using a hyperspectral imaging array, and/or using narrowband tunable filters for passing filtered received light to an imager. Embodiments may construct a 3-D surface model from stereo images, and will estimate optical properties of the target using images taken in patterned light or using other approximations obtained from white light exposures. Hyperspectral images taken under stimulus light are displayed as fluorescent images, and corrected for optical properties of
(Continued)

tissue to provide quantitative maps of fluorophore concentration. Spectral information from hyperspectral images is processed to provide depth of fluorophore below the tissue surface. Quantitative images of fluorescence at depth are also prepared. The images are displayed to a surgeon for use in surgery.

15 Claims, 26 Drawing Sheets

Related U.S. Application Data continuation-in-part of application No. 14/373,443, filed as application No. PCT/US2013/022266 on Jan. 18, 2013, now abandoned, application No. 15/044,097, which is a continuation-in-part of application No. 14/375,311, filed as application No. PCT/US2013/024400 on Feb. 1, 2013, now Pat. No. 9,336,592, application No. 15/044,097, which is a continuation-in-part of application No. 14/370,713, filed as application No. PCT/US2013/020352 on Jan. 4, 2013, now Pat. No. 9,456,200.

(60) Provisional application No. 61/866,282, filed on Aug. 15, 2013, provisional application No. 61/588,708, filed on Jan. 20, 2012, provisional application No. 61/594,862, filed on Feb. 3, 2012, provisional application No. 61/583,092, filed on Jan. 4, 2012.

(51) Int. Cl.

| | | |
|---|---|---|
| *A61B 1/04* | (2006.01) | |
| *A61B 5/145* | (2006.01) | |
| *A61B 5/00* | (2006.01) | |
| *A61B 5/1495* | (2006.01) | |
| *A61B 1/06* | (2006.01) | |
| *A61B 1/00* | (2006.01) | |
| *A61B 5/055* | (2006.01) | |
| *G01J 3/28* | (2006.01) | |
| *A61B 1/05* | (2006.01) | |
| *G01J 3/12* | (2006.01) | |
| *G01J 3/02* | (2006.01) | |
| *A61B 1/07* | (2006.01) | |
| *A61B 1/313* | (2006.01) | |

(52) U.S. Cl.
CPC .......... *A61B 1/00193* (2013.01); *A61B 1/042* (2013.01); *A61B 1/043* (2013.01); *A61B 1/05* (2013.01); *A61B 1/0646* (2013.01); *A61B 1/0669* (2013.01); *A61B 1/0684* (2013.01); *A61B 1/07* (2013.01); *A61B 5/0071* (2013.01); *A61B 5/0077* (2013.01); *A61B 5/055* (2013.01); *A61B 5/1459* (2013.01); *A61B 5/1495* (2013.01); *A61B 5/14546* (2013.01); *A61B 5/14553* (2013.01); *A61B 5/7264* (2013.01); *G01J 3/0229* (2013.01); *G01J 3/1256* (2013.01); *G01J 3/2823* (2013.01); *A61B 1/3132* (2013.01); *G01J 2003/1269* (2013.01); *G01J 2003/2826* (2013.01)

(58) Field of Classification Search
CPC .................. A61B 6/5235; A61B 6/5247; G01J 2003/1269; G01J 2003/2826; G01J 3/0229; G01J 3/1256; G01J 3/2823
See application file for complete search history.

(56) References Cited

U.S. PATENT DOCUMENTS

| | | |
|---|---|---|
| 6,175,759 B1 | 1/2001 | Chan et al. |
| 6,208,886 B1 | 3/2001 | Alfano et al. |
| 6,379,302 B1 | 4/2002 | Kessman et al. |
| 6,661,571 B1 | 12/2003 | Shioda et al. |
| 6,678,398 B2 | 1/2004 | Wolters et al. |
| 6,793,350 B1 | 9/2004 | Raskar et al. |
| 6,961,405 B2 | 11/2005 | Scherch |
| 7,085,400 B1 | 8/2006 | Holsing et al. |
| 7,387,802 B2 | 6/2008 | Sambanthamurthi et al. |
| 7,804,075 B2 | 9/2010 | Ntziachristos et al. |
| 7,945,077 B2 | 5/2011 | Demos |
| 8,406,859 B2 | 3/2013 | Zuzak et al. |
| 8,948,851 B2 | 2/2015 | Leblond et al. |
| 9,052,384 B2 | 6/2015 | Hartov et al. |
| 9,336,592 B2 | 5/2016 | Fan et al. |
| 9,456,200 B2 | 9/2016 | Ji et al. |
| 9,655,545 B2 | 5/2017 | Ji et al. |
| 2002/0080481 A1 | 6/2002 | Tachihara et al. |
| 2002/0099295 A1 | 7/2002 | Gil et al. |
| 2003/0158470 A1 | 8/2003 | Wolters et al. |
| 2004/0015062 A1 | 1/2004 | Ntziachristos et al. |
| 2004/0215072 A1 | 10/2004 | Zhu |
| 2005/0085732 A1 | 4/2005 | Sevick-Muraca et al. |
| 2005/0111758 A1 | 5/2005 | Lange et al. |
| 2005/0215911 A1 | 9/2005 | Alfano et al. |
| 2006/0024390 A1 | 2/2006 | Schauss et al. |
| 2006/0033026 A1 | 2/2006 | Treado et al. |
| 2007/0145136 A1 | 1/2007 | Wiklof et al. |
| 2007/0038126 A1 | 2/2007 | Pyle et al. |
| 2007/0083124 A1 | 4/2007 | Ehben et al. |
| 2007/0165927 A1 | 7/2007 | Muradyan et al. |
| 2007/0167835 A1* | 7/2007 | Yu .................. A61B 5/0059 600/476 |
| 2007/0236414 A1 | 10/2007 | Lin |
| 2007/0236514 A1 | 10/2007 | Agusanto et al. |
| 2007/0238957 A1 | 10/2007 | Yared |
| 2007/0299335 A1 | 12/2007 | Declerck et al. |
| 2008/0218727 A1 | 9/2008 | Djeziri et al. |
| 2008/0267472 A1 | 10/2008 | Demos |
| 2009/0021746 A1 | 1/2009 | Toida et al. |
| 2009/0036902 A1 | 2/2009 | Dimaio et al. |
| 2009/0076732 A1 | 3/2009 | Sprigle et al. |
| 2009/0137908 A1 | 5/2009 | Patwardhan |
| 2009/0180178 A1 | 7/2009 | Luecke et al. |
| 2009/0295910 A1 | 12/2009 | Mir et al. |
| 2009/0326362 A1 | 12/2009 | Carise et al. |
| 2010/0019170 A1 | 1/2010 | Hart et al. |
| 2010/0056928 A1* | 3/2010 | Zuzak ................. A61B 5/0071 600/476 |
| 2010/0085423 A1 | 4/2010 | Lange |
| 2010/0145416 A1 | 6/2010 | Kang et al. |
| 2010/0201789 A1 | 8/2010 | Yahagi |
| 2010/0208963 A1 | 8/2010 | Kruecker et al. |
| 2011/0054355 A1 | 3/2011 | Hunter et al. |
| 2011/0102549 A1 | 5/2011 | Takahashi |
| 2011/0124988 A1* | 5/2011 | Cuccia ................ A61B 5/0059 600/310 |
| 2011/0128352 A1 | 6/2011 | Higgins et al. |
| 2011/0175910 A1 | 7/2011 | Yahagi |
| 2011/0183370 A1 | 7/2011 | Noiseux et al. |
| 2011/0222757 A1 | 9/2011 | Yeatman et al. |
| 2011/0275932 A1* | 11/2011 | Leblond ............... A61B 5/0062 600/425 |
| 2011/0293142 A1 | 12/2011 | Van Der Mark et al. |
| 2012/0002012 A1 | 1/2012 | O'Grady et al. |
| 2012/0112098 A1 | 5/2012 | Hoyt |
| 2012/0133740 A1 | 5/2012 | Klimov et al. |
| 2012/0307056 A1 | 12/2012 | Zuzak et al. |
| 2013/0012794 A1 | 1/2013 | Zeng et al. |
| 2013/0038689 A1 | 2/2013 | McDowall |
| 2013/0076863 A1 | 3/2013 | Rappel |
| 2013/0259805 A1 | 10/2013 | Bacskai |
| 2014/0020476 A1 | 1/2014 | Inoue et al. |
| 2014/0063241 A1 | 3/2014 | Li et al. |
| 2014/0362186 A1 | 12/2014 | Ji et al. |

(56) References Cited

U.S. PATENT DOCUMENTS

| | | |
|---|---|---|
| 2014/0378843 A1 | 12/2014 | Valdes et al. |
| 2015/0264340 A1 | 9/2015 | Seidl et al. |
| 2015/0374308 A1 | 12/2015 | Tichauer et al. |
| 2017/0085855 A1 | 3/2017 | Roberts et al. |
| 2017/0119330 A1 | 5/2017 | Tichauer et al. |

FOREIGN PATENT DOCUMENTS

| | | |
|---|---|---|
| KR | 10-1088364 B1 | 12/2011 |
| WO | 2000/027131 A2 | 5/2000 |
| WO | 2005/089637 A2 | 9/2005 |
| WO | 2005/099581 A1 | 10/2005 |
| WO | 2007/111570 A2 | 10/2007 |
| WO | 2009/061425 A1 | 5/2009 |
| WO | 2009/143491 A2 | 11/2009 |
| WO | 2010/090673 A1 | 8/2010 |
| WO | 2011/113162 A1 | 9/2011 |
| WO | 2013/040555 A2 | 3/2013 |
| WO | 2013/103870 A1 | 7/2013 |
| WO | 2013/109966 A1 | 7/2013 |
| WO | 2013/116694 A1 | 8/2013 |
| WO | 2013/122710 A1 | 8/2013 |
| WO | 2014/127145 A1 | 8/2014 |
| WO | 2015/023990 A1 | 2/2015 |
| WO | 2015/187620 A1 | 12/2015 |
| WO | 2016/007734 A1 | 1/2016 |

OTHER PUBLICATIONS

Raymond et al. (2010) "Lifetime-based tomographic multiplexing," Journal of Biomedical Optics, vol. 15, Issue 4, 9 pp.

U.S. Appl. No. 14/373,443, Final Office Action dated Dec. 17, 2018, 26 pp.

U.S. Appl. No. 12/994,044, filed Jan. 21, 2011, 2011/0153254, Jun. 23, 2011, U.S. Pat. No. 9,052,384, Alexander Hartov.

U.S. Appl. No. 13/145,505, filed Jul. 20, 2011, 2011/0275932, Nov. 10, 2011, U.S. Pat. No. 8,948,851, Feb. 3, 2015, Frederic Leblond.

U.S. Appl. No. 14/345,029, filed Mar. 14, 2014, 2014/0371600, Dec. 18, 2014, U.S. Pat. No. 9,655,545, May 23, 2017, Songhai Ji.

U.S. Appl. No. 14/370,713, filed Jul. 3, 2014, 2014/0362186, Dec. 11, 2014, U.S. Pat. No. 9,456,200, Sep. 27, 2016, Songhai Ji.

U.S. Appl. No. 14/373,443 2014/0378843, filed Jul. 21, 2014 Dec. 25, 2014, Pablo A. Valdes.

U.S. Appl. No. 14/375,311, filed Jul. 29, 2014, 2014/0369584, Dec. 18, 2014, U.S. Pat. No. 9,336,592, Xiaoyao Fan.

U.S. Appl. No. 14/767,836 2015/0374308, filed Aug. 13, 2015 Dec. 31, 2015, Kenneth Tichauer.

2016/0278678, Sep. 29, 2016, Pablo Valdes.

U.S. Appl. No. 15/367,243 2017/0085855, filed Dec. 2, 2016 Mar. 23, 2017, David W. Roberts.

U.S. Appl. No. 15/402,077 2017/0119330, filed Jan. 9, 2017 May 4, 2017, Pablo Valdes.

PCT/US2009/045082 WO 2009/143491, filed May 22, 2009 Nov. 26, 2009, Alexander Hartov.

PCT/US2009/066839 WO 2010/090673, filed Dec. 4, 2009 Aug. 12, 2010, Frederic Leblond.

PCT/US2012/055755 WO 2013/040555, filed Sep. 27, 2012 Mar. 21, 2013, Songhai Ji.

PCT/US2013/020352 WO 2013/103870, filed Jan. 4, 2013 Jul. 11, 2013, Songhai Ji.

PCT/US2013/022266 WO 2013/109966, filed Jan. 18, 2013 Jul. 25, 2013, Pablo Valdes.

PCT/US2013/024400 WO 2013/116694, filed Feb. 1, 2013 Aug. 8, 2013, Xiaoyao Fan.

PCT/US2014/016291 WO 2014/127145, filed Feb. 13, 2014 Aug. 21, 2014, Kenneth Tichauer.

PCT/US2014/051356 WO 2015/023990, filed Aug. 15, 2014 Feb. 19, 2015, Pablo Valdes.

PCT/US2015/033672 WO 2015/187620, filed Jun. 2, 2015 Dec. 10, 2015, David W. Roberts.

PCT/US2015/0369728 WO 2016/007734 filed Jul. 9, 2015 Jan. 14, 2016, Kenneth Tichauer.

Rajaram et al. (2008), "Lookup table-based inverse model for determining optical properties of turbid media" J Biomed Opt. 2008; 13(5): 050501.

U.S. Appl. No. 14/373,443, Non-Final Rejection dated Mar. 9, 2018; 20 pp.

Office Action corresponding to U.S. Appl. No. 12/994,044, dated May 15, 2014, 13 pgs.

Office Action corresponding to U.S. Appl. No. 12/994,044, dated Oct. 6, 2014, 15 pgs.

Office Action corresponding to U.S. Appl. No. 13/145,505, dated Jun. 20, 2013, 21 pgs.

Office Action corresponding to U.S. Appl. No. 13/145,505, dated Nov. 14, 2013, 10 pgs.

Office Action corresponding to U.S. Appl. No. 14/345,029, dated Jul. 25, 2016, 10 pgs.

Office Action corresponding to U.S. Appl. No. 14/345,029, dated Oct. 7, 2015, 10 pgs.

Office Action corresponding to U.S. Appl. No. 14/370,713, dated Feb. 2, 2016, 17 pgs.

Office Action corresponding to U.S. Appl. No. 14/373,443, dated Jun. 21, 2017, 20 pgs.

Office Action corresponding to U.S. Appl. No. 14/3/3,443, dated Nov. 16, 2016, 17 pgs.

Restriction Requirement corresponding to U.S. Appl. No. 12/994,044, dated Oct. 21, 2013, 6 pgs.

Restriction Requirement corresponding to U.S. Appl. No. 13/145,505, dated Mar. 27, 2015, 9 pgs.

Restriction Requirement corresponding to U.S. Appl. No. 14/373,443, dated Sep. 8, 2016, 10 pgs.

Restriction Requirement corresponding to U.S. Appl. No. 14/375,311, dated Oct. 5, 2015, 6 pgs.

Bradley et al. (2006) "A review of attenuation correction techniques for tissue fluorescence," Journal of the Royal Society Interface. 3(6):1-13.

Davis et al. (2005) "Contrast-detail analysis characterizing diffuse optical fluorescence tomography image reconstruction," J. Biomed. Optics. 10(5):050501. pp. 1-3.

Diop et al. (2012) "Deconvolution method for recovering the photon time-of-flight distribution from time-resolved measurements," Optics Letters. 37:2358-60.

Fan (May 2012) "Later Stage Brain Deformation Compensation In Image-Guided Neurosurgery," Ph.D. Dissertation. Dartmouth College.

Fan et al. (2011) "Simulation of Brain Tumor Resection in Image-Guided Neurosurgery," Medical Imaging 2011: Visulization Image-Guided Procedures, and Modeling, Proc. of SPIE Proceedings vol. 796. 79640U. pp. 1-11.

Fan et al. (2012) "Registering Stereovision Surface with Preoperative Magnetic Resonance Images for Brain Shift Compensation," Proceedings vol. 8316, Medical Imaging 2012: Image-Guided Procedures, Robotic Interventions, and Modeling. 83161C. pp. 1-10.

Fellers et al. (2012) "Acousto-Optic Tunable Filters (AOTFs)," Accessible on the Internet at URL: http://www.olympusmicro.com/primer/techniques/confocal/aotfintro.html. [Last Accessed Oct. 12, 2017].

Feng et al. (2010) "Relative Brain Displacement and Deformation During Constrained Mild Frontal Head Impact," J R Soc Interface 7(53):1677-88.

Friesen et al. (2002) "5-Aminolevulinic acid-based photodynamic detection and therapy of brain tumors (review)," Int. J. Oncol. 21(3):577-582.

Gao et al. (2010) "Snapshot Image Mapping Spectrometer (IMS) with high sampling density for hyperspectral microscopy," Optics Express. 18:14330-14344.

Hartov et al. (1999) "Error Analysis for a Free-Hand Three Dimensional Ultrasound System for Neuronavigation," Neurosurg. Focus. 6(3):5. 14 pgs.

Hillman (2007) "Optical brain imaging in vivo: techniques and applications from animal to man," J. Biomed. Optics. 12(5):051402.

(56) References Cited

OTHER PUBLICATIONS

Joshi (2010) "DigiWarp: a method for deformable mouse atlas warping to surface topographic data," Phys. Med. Biol. 55(20):6197-214.
Kuroiwa et al. (1998) "Development of a fluorescein operative microscope for use during malignant glioma surgery: a technical note and preliminary report," Surg. Neurol. 50(1):41-48.
Leblond et al. (2007) "Diffuse optical fluorescence tomography using time-resolved data acquired transmission," Proceedings vol. 6431, Multimodal Biomedical Imaging II. 643106.
Miller et al. (2000) "Mechanical Properties of Brain Tissue In-Vivo: Experiment and Computer Simulation," Journal of Biomechanics 33:1369-1376.
Najib et al. (2011) "Transcranial brain stimulation: clinical applications and future directions," Neurosurg. Clin. N. Am. 22(2):233-51.
Nourrit et al. (2010) "High-resolution hyperspectral imaging of the retina with a modified fundus camera," J. Fr. Opthamol. 33(10):686-692.
Ntziachristos et al. (2000) "Concurrent MRI and diffuse optical tomography of breast after indocyanine green enhancement," Proc. Natl. Acad. Sci. USA 97(6):2767-72.
Ntziachristos et al. (2002) "Charge-coupled-device based scanner for tomography of fluorescent near-infrared probes in turbid media," Medical Physics. 29(5):803-9.
Patwardhan (2005) "Monte Cado Simulation of Light-Tissue Interaction: Three-Dimensional Simulation forTrans-Illumination-Based Imaging of Skin Lesions," IEEE Transactions on Biomedical Engineering. 52(7):1227-1236.
Saager et al. (2011) "Quantitative fluorescence imaging of protoporphyrin IX through determination of tissue optical properties in the spatial frequency domain," Journal of Biomedical Optics. 16(12):126013. pp. 1-5.
Sabet et al. (2008) "Deformation of the human brain induced by mild angular head acceleration," J. Biomech. 41:307-15.
Stummer et al. (2006) "Fluorescence-guided surgery with 5-aminolevulinic acid for resection of malignant glioma: a randomised controlled multicentre phase III trial," Lancet Oncology. 7(5):392-401.
Sun (May 2004) "Stereopsis-Guided Brain Shift Compensation," Ph.D. Dissertation. Dartmouth College.
Sun et al. (2005) "Stereopsis-Guided Brain Shift Compensation," IEEE Trans Med. Imaging. 25(8):1039-1052.
Swartling et al. (2005) "Fluorescence spectra provide information on the depth of fluorescent lesions in tissue," Optics Letters. 44(10):1934-1941.
Tichauer et al. (Apr. 2014) "Accounting for pharmacokinetic differences in dual-tracer receptor density imaging," Phys. Med. Biol. 59:2341-2351.
Tichauer et al. (Jan. 2013) "Dual-tracer background subtraction approach for fluroescent molecular tomography," Journal of Biomedical Optics. 18(1):016003.
Tichauer et al. (Jun. 2012) "Improved tumor contrast achieved by single time point dual-reporter fluorescence imaging," Journal of Biomedical Optics. 17(6):066001. pp. 1-10.
Valdes (2011) "Quantitative fluorescence in intracranial tumor: implications for ALA-induced PpIX as an intraoperative biomarker," J. Neurosurg. 115:11-17.
Valdes et al. (Jun. 1, 2012) "A spectrally constrained dual-band normalization technique for protoporphyrin IX pantification in fluorescence-guided surgery," Optics Letters. 37(11):1817-1819.
Vigneron et al. (2009) "2D XFEM-Based Modeling of Retraction and Successive Resections For Preoperative Image Update," Comput. Aided Surg. 14(1-3):1-20.
Zhang et al. (2000) "Turbidity-free fluorescence spectroscopy of biological tissue," Optic Letters. 25(19):1451-1453.
International Search Report with Written Opinion corresponding to International Patent Application No. PCT/US2009/045082, dated Jan. 7, 2010, 6 pgs.
International Search Report with Written Opinion corresponding to International Patent Application No. PCT/US2009/066839, dated Jun. 25, 2010, 7 pgs.
International Search Report with Written Opinion corresponding to International Patent Application No. PCT/US2012/055755, dated Feb. 28, 2013, 7 pgs.
International Search Report with Written Opinion corresponding to International Patent Application No. PCT/US2013/020352, dated Apr. 26, 2013, 7 pgs.
International Search Report with Written Opinion corresponding to International Patent Application No. PCT/US2013/022266, dated May 15, 2013, 8 pgs.
International Search Report with Written Opinion corresponding to International Patent Application No. PCT/US2013/024400, dated May 15, 2013, 10 pgs.
International Search Report with Written Opinion corresponding to International Patent Application No. PCT/US2014/016291, dated May 27, 2014, 11 pgs.
International Search Report with Written Opinion corresponding to International Patent Application No. PCT/US2014/051356, dated Dec. 9, 2014, 8 pgs.
International Search Report with Written Opinion corresponding to International Patent Application No. PCT/US2015/033672, dated Aug. 19, 2015, 9 pgs.
International Search Report with Written Opinion corresponding to International Patent Application No. PCT/US2015/039728, dated Oct. 7, 2015, 10 pgs.
Notice of Allowance corresponding to U.S. Appl. No. 12/994,044, dated Feb. 5, 2015, 11 pgs.
Notice of Allowance corresponding to U.S. Appl. No. 13/145,505, dated Sep. 30, 2014, 9 pgs.
Notice of Allowance corresponding to U.S. Appl. No. 14/345,029, dated Feb. 14, 2017, 9 pgs.
Notice of Allowance corresponding to U.S. Appl. No. 14/370,713, dated May 18, 2016, 9 pgs.
Notice of Allowance corresponding to U.S. Appl. No. 14/375,311, dated Jan. 20, 2016, 16 pgs.
Office Action corresponding to U.S. Appl. No. 12/994,044, dated Jan. 3, 2014, 11 pgs.

\* cited by examiner

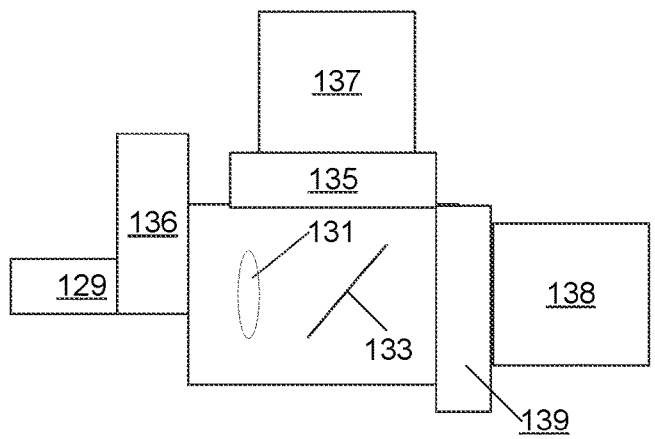
Fig. 1A
Fig. 1B
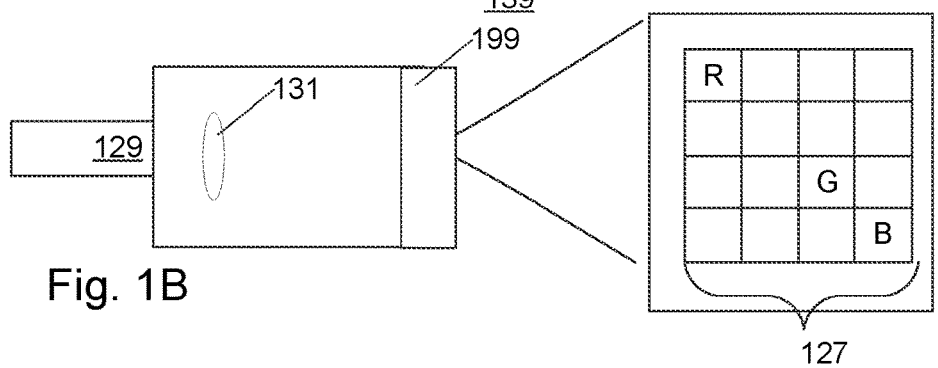
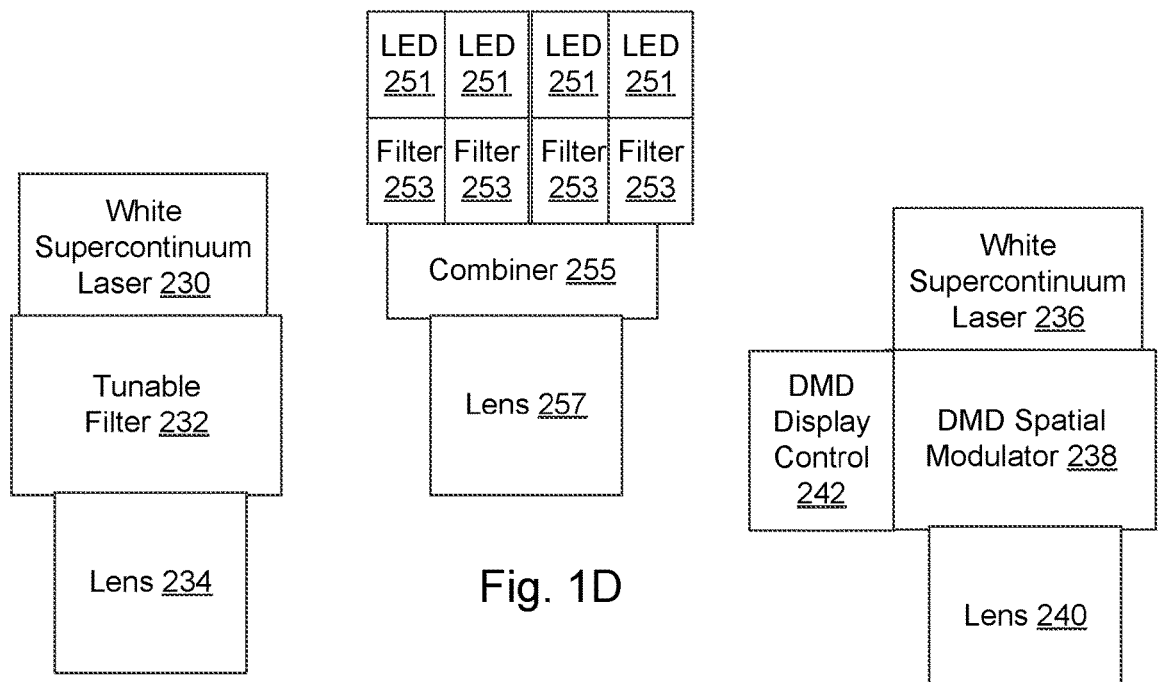
Fig. 1C
Fig. 1D
Fig. 1E

VIS fluorophores

Fig. 19

Depth-resolved fluorescence imaging (dFI)

Fluorescence
- Single-wavelength fluorophore excitation
- Spectrally-resolved fluorescence detection

Reflectance
- White-light tissue excitation
- Spectrally-resolved reflectance detection
- Single or multiple-wavelengths spatially-modulated tissue excitation

Non-model based technique
See flowchart D4 for data processing steps

Light transport based technique
See flowchart D5 for data processing steps

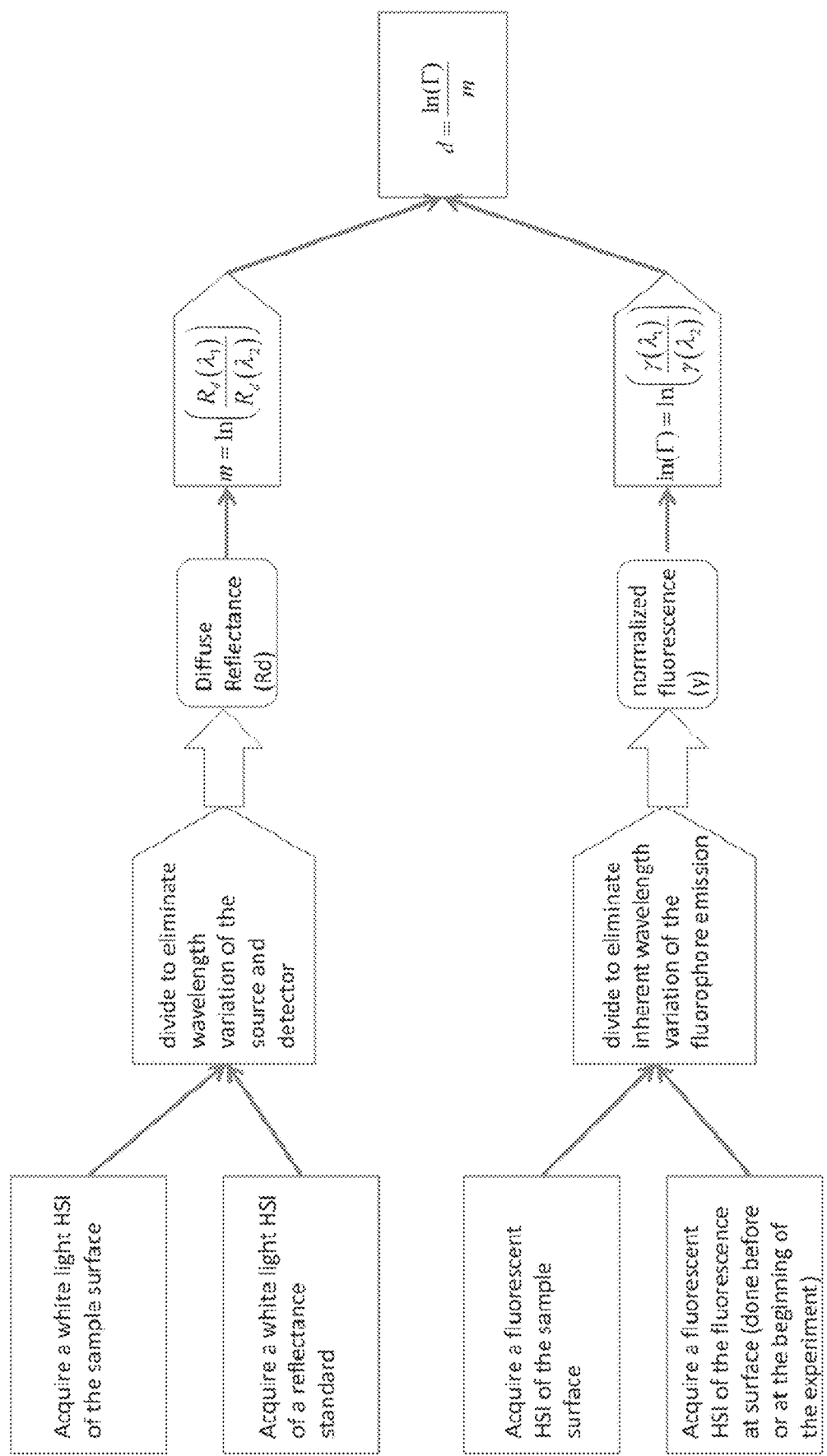
Flowchart D4 Fig. 20

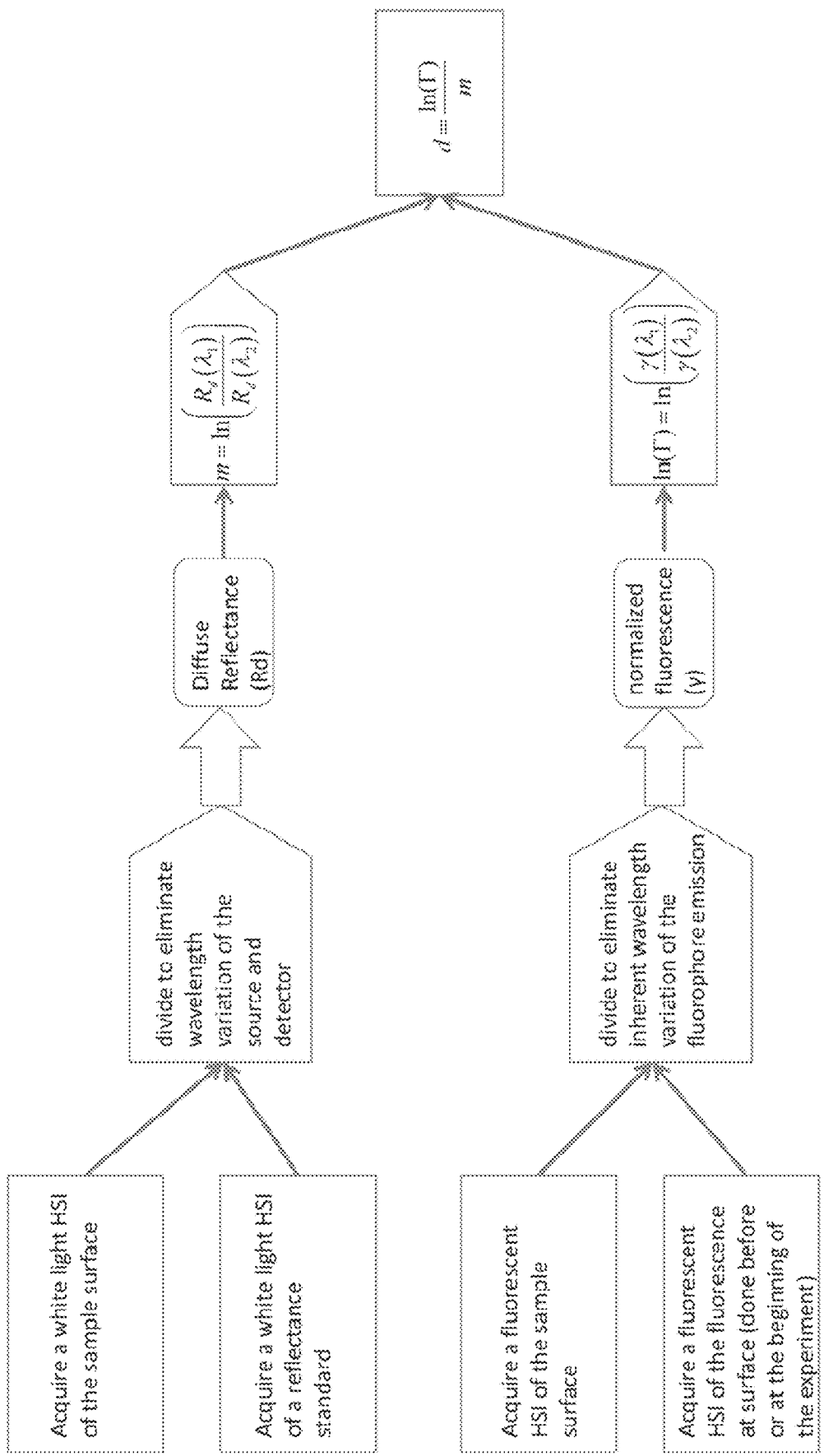
Flowchart D5   Fig. 21

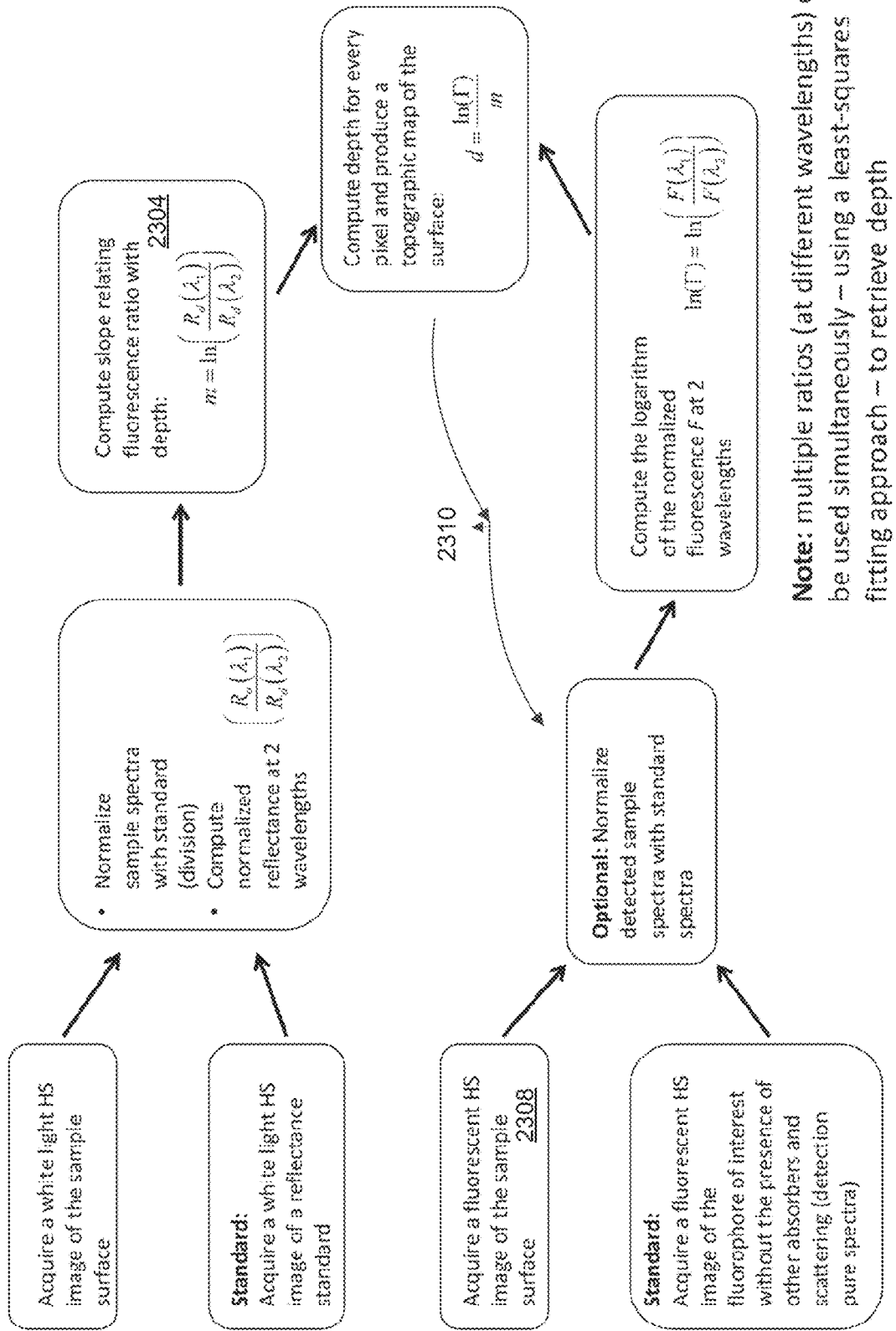

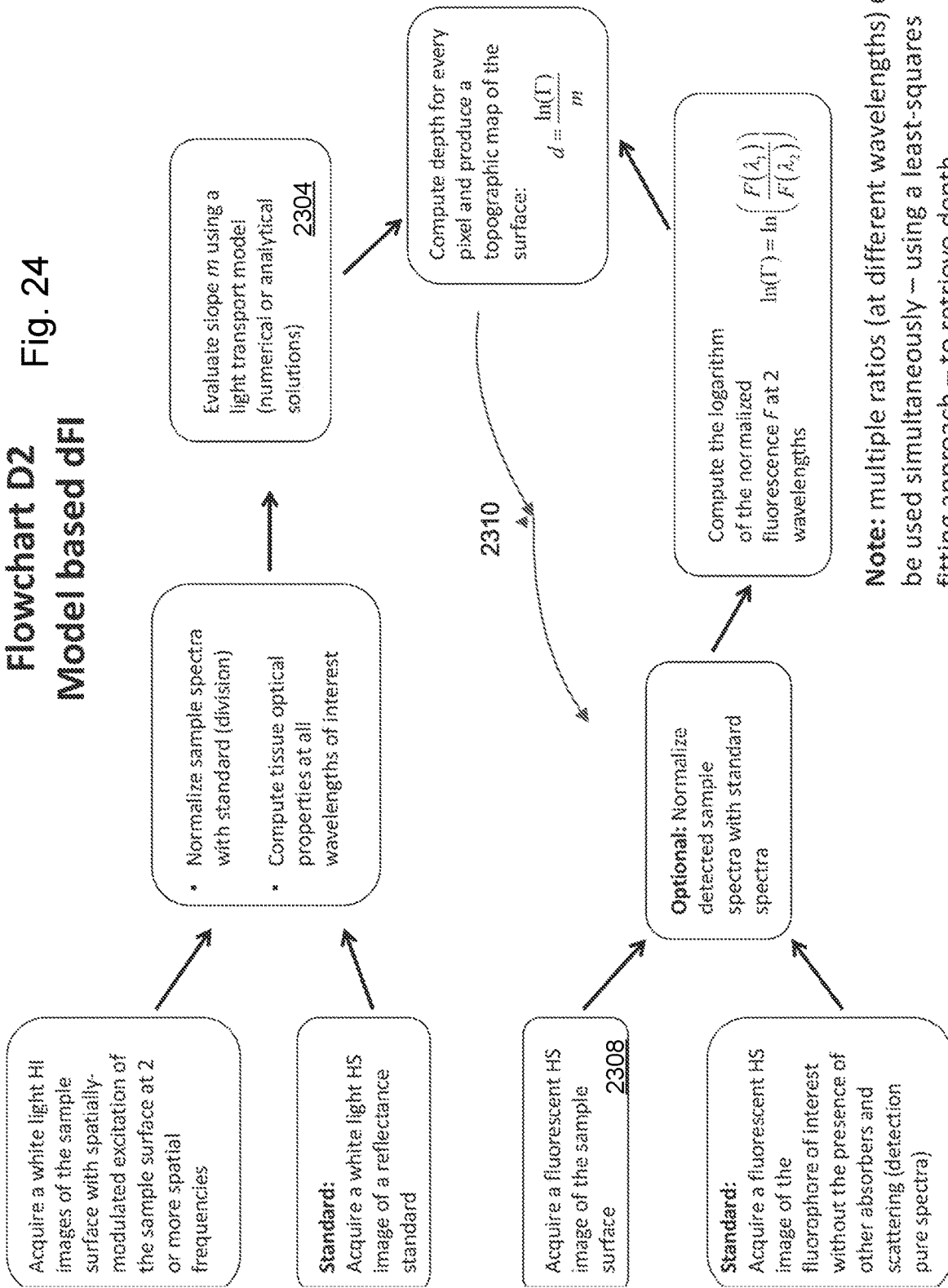

METHOD AND APPARATUS FOR QUANTITATIVE AND DEPTH RESOLVED HYPERSPECTRAL FLUORESCENCE AND REFLECTANCE IMAGING FOR SURGICAL GUIDANCE

RELATED APPLICATIONS

This application is a continuation of PCT Patent Application PCT/US2014/051356 filed Aug. 14, 2014 which claims priority to U.S. Provisional Patent Application 61/866,282 filed 15 Aug. 2013.

The present application is also a continuation-in-part application of U.S. patent application Ser. No. 14/373,443 filed Jul. 21, 2014 which is a U.S. National Phase Application of PCT Patent Application PCT/US2013/022266 filed Jan. 18, 2013, which claims priority to 61/588,708 filed Jan. 20, 2012.

The present application is also a continuation-in-part application of U.S. patent application Ser. No. 14/375,311 filed Jul. 29, 2014 which is a U.S. National Phase Application of PCT Patent Application PCT/US2013/024400 filed Feb. 1, 2013, which claims priority to 61/594,862 filed Feb. 3, 2012 and U.S. Patent Application 61/583,092, filed Jan. 4, 2012.

The present application is also a continuation-in-part application of U.S. patent application Ser. No. 14/370,713 filed Jul. 3, 2014, which is a U.S. National Phase Application of PCT/US2013/020352 filed Jan. 4, 2013, which claims priority to 61/583,092 filed Jan. 4, 2012.

The present application is also related to U.S. patent application Ser. No. 13/145,505, filed 20 Jul. 2011, now U.S. Pat. No. 8,948,851 which is a U.S. national phase of U.S. Patent Cooperation Treaty Application PCT/US/2009/066839 filed 4 Dec. 2009, which claims priority to U.S. Provisional Application 61/145,900 filed 10 Jan. 2009.

The aforementioned patent applications are hereby incorporated herein in their entirety by reference.

GOVERNMENT RIGHTS

This invention was made with government support under grant numbers R01 CA159324-01, K25 CA138578, R01 EB002082-11, 1R21 NS078607, and R01NS052274-01A2 awarded by the National Institutes of Health. The government has certain rights in the invention.

FIELD

The present application relates to the fields of surgery and imaging of surgical sites. In particular, the present application relates to hyperspectral fluorescence and reflectance imaging with quantification and depth resolution in model or non-model based implementations to improve the ability of a surgeon to distinguish tissue types during surgical procedures.

BACKGROUND

There are many types of lesions treatable with surgery. These lesions include tissues abnormal for any location in the body, such as malignant (or cancerous) tumors, and many slower-growing "benign" tumors. These lesions also include tissues that are abnormal for their location in a particular organ, but resemble normal tissues found in other locations in the body. Other lesions may incorporate material foreign to the body, including bacteria, viruses, or parasites, and associated zones of immune reactions. Still others involve developmental anomalies, such as arteriovenous malformations and berry aneurisms, or have portions with abnormal metabolic conditions. Other lesions may incorporate scars and adhesions from prior illness or injury. While lesions are of many kinds, it is generally desirable for a surgeon to be able to visualize the lesion being treated and to be able to discriminate between normal and lesion tissues—even when lesion tissue resembles surrounding normal tissue.

Many tumors and other lesions do not have a capsule or other connective tissue that separates them from nearby normal tissues; these may have irregular boundaries. Invasive malignant tumors in particular often have infiltrations and filaments containing malignant cells that penetrate into adjacent normal tissue. Some tumor types, including gliomas, produce motile cells that may migrate a short distance away from the tumor into normal tissue; once these cells have found a hospitable location they may grow and form a new spinoff or satellite tumor. The new tumor may or may not become attached to the parent tumor, if it becomes attached it may resemble an invasive filament of tumor. Either way, the tumor may develop a somewhat ragged edge with filaments and spots penetrating into adjacent tissue.

To reduce recurrence of many tumors after surgical treatment, including many malignancies, it is considered desirable to remove all detectable portions of the tumor.

While filaments of tumor, and motile cells, may stop extending for a time when they reach an organ capsule, resulting in tumor encapsulated in the organ, it is often undesirable to remove an entire organ or organ lobe—especially when an organ is critical for life and the tumor may not have invaded the entire organ. For example, removal of more brain tissue or spinal cord than necessary can cause life-altering neurological impairment or death. Similarly, it may be desirable to save as much as possible of a patient's liver, his only remaining kidney, or his dominant arm. There are other organs and body structures where tumors may form but where it may be desirable to retain as much post-surgery organ structure and function as possible.

Invasive filaments and clones from formerly motile cell portions of some tumors may not be readily discerned by a surgeon even under magnification because some portions of some benign and some malignant tumors have tissue that superficially resembles tissue like that from which the tumor arose in both color and, to a certain extent, in texture; a tumor that arose in an organ often has portions that are difficult to visually distinguish from surrounding tissue. Other lesion types may also have portions with color and structure that resemble nearby healthy tissue, making it difficult for the surgeon to distinguish the lesions from the healthy tissue.

A prior method of ensuring complete tumor removal while retaining as much organ as possible involves a pathologist cooperating with the surgeon. The surgeon removes the tumor and some adjacent tissue, while the pathologist immediately examines frozen sections to verify that the removed tissue includes a tumor-free margin. Should tumor portions be found to extend to boundaries of the removed tissue, extension of tumor beyond the removed tissue is assumed and more adjacent tissue is removed before closing the incision. This method is slow, requiring extended anesthesia times and repeated frozen sections, and may require removal of more tissue than necessary because frozen sections can only be performed after the tissue is removed from the patient. Further, not all abnormal tissue types are readily distinguished in a frozen section. An alternative or supplemental method involves pathological examination of stained sections to verify complete tumor removal with removal of adequate margins of healthy tissue, however stained sections often take so much time to prepare that any further removal requires re-operation.

Generally, surgeons treat lesions that are visible to them during surgery. At times, lesions and tumors may lie under the surface of an organ, or under a visible and exposed surface of an operative site, where they may be obscured by overlying tissue and not readily visible, or may have poor contrast relative to surrounding stroma. It is desirable to make these lesions, including portions of malignant tumors, visible to a surgeon so that they can be more readily treated, with less normal overlying tissue damaged during treatment, than with current techniques.

Some fluorescent compounds will accumulate in tumors and other abnormal tissues. Further, some prodrugs, such as 5-aminolevulinic acid (5-ALA) can be metabolized into fluorescent compounds to a greater extent in some tumor tissues than in surrounding normal stroma. Marking of tumors with 5-ALA metabolites and using resultant fluorescence at the surface of an operative site to guide surgery has been reported in the literature. For example Stummer, et al., "Fluorescence-Guided Surgery with 5-Aminolevulinic Acid for Resection of Malignant Glioma: A Randomized Controlled Multicentre Phase III Trial," Lancet Oncology, Lancet Oncology, Lancet Oncol., 2006. 7(5): p. 392-401, published online Apr. 13, 2006 at oncology.thelancet.com, reports that removal of malignant glioma tumor tissue marked with fluorescent metabolites of 5-ALA and fluorescing in the visible spectrum at the surface of an operative site under violet-blue excitation light during surgical treatment of glioma improved extent of tumor resection and enhanced six month progression free survival in human subjects. Similar studies have also been performed in laboratory rodents, including mice and rats with tumor models. It is expected that these results may apply for other lesion types.

Most tissues of the human body are soft tissues inherently flexible and deformable. Further, many soft tissues interface with other tissues along boundaries where considerable movement may take place. During surgery, as adjacent structures such as skin, muscle, and bone are moved and pressure applied with instruments such as retractors, these tissues deform and shift. Since these tissues may deform both between imaging and surgery, and during surgery, it is common for surgeons to find that lesions, including tumors and foreign objects, and other surgical targets are no longer in positions they occupied in preoperative images. For a surgeon to properly treat these lesions, the surgeon must locate them during surgery. Further, for surgeons to avoid unintended damage to other nearby structures, it may also be necessary to locate those other structures precisely.

There are chromophores naturally present in biological tissues, including human tissue. A leading such chromophore is the iron-containing heme group—as found in myoglobin and hemoglobin. Heme is generally found in both oxygenated and de-oxygenated forms in the body, and it is well known that absorption spectra of heme differs between the oxygenated and de-oxygenated forms; this difference in absorption may be used to identify tissues having different oxygen concentrations. Blood vessels, and some other structures that it may be desirable to protect during surgery, may have or may contain concentrations of such chromophores.

Many malignant tumor types have high metabolic activity due to rapid cell division and growth. These tumors often outgrow the local oxygen supply; some tumors stimulate rapid proliferation of blood vessels to overcome this, and some tumors develop core areas of low oxygen tension and may develop necrotic portions. Imaging of heme concentrations and oxygenation may assist in locating some types of malignant tumor tissue, as well as imaging tissues such as muscle, bone marrow, liver, spleen, and blood vessels including arteriovenous malformations and aneurysms that naturally have high heme concentrations.

Muscle, including cardiac muscle, and brain activities consume more oxygen when active than when idle. A normal physiological response to this increase of oxygen consumption with activity is to dilate blood vessels to increase blood flow in affected tissue. In many diseases, including peripheral vascular disease, and cardiovascular disease, as well as cerebrovascular disease, ischemic bowel disease, the centers of some types of tumors, and other conditions, this physiological increase of flow is impaired resulting in a local decrease in oxygenation of heme. A significant decrease in oxygenation, such as may be caused by damaged blood vessels, may produce pain or other signs and symptoms, as in intermittent claudication or angina. Further, mapping increases in blood flow due to brain activity can be of interest in monitoring activity in the brain.

For all these reasons, it is desirable to be able to map areas of heme concentration, to map areas of oxygenated hemoglobin and de-oxygenated hemoglobin, and to be able to view dynamic changes in oxygenation with tissue activity.

Other chromophores naturally present in some tissues, including some types of tumor tissues, are naturally fluorescent. Further, optical properties of normal tissues of different tissue types are known to differ, and some optical properties of some diseased tissues tissue types have been shown to differ from normal tissues of the same organ.

The extent of resection for brain tumor procedures has been shown to correlate with patient survival and quality of life. Accurate tumor tissue identification with a surgical microscope alone can be challenging because of lack of visual or mechanical features in tissue to discriminate between normal tissue and tumor. Fluorescence-guided neurosurgery marks tumor tissue with a fluorescent contrast agent, and uses fluorescence detection technologies to identify tumor tissue using the fluorescence signals emitted from tumor tissue. Current surgical microscopes enabled for fluorescence imaging typically perform single-band, single-spectral-wavelength, detection. Although useful, significant levels of tumor tissue can be left undetected using this fluorescence imaging approach.

Prior fluorescence detection technologies in the operating room display features and functionalities such as: i) surgical microscopes modified for broad-beam fluorescence imaging currently allow for wide-field, for example, up to 50 cm$^2$, single-band, 620-720 nm, non-spectrally resolved fluorescence detection that assesses fluorescence qualitatively, without accounting for non-linear effects of tissue optical properties on the emitted fluorescence; and ii) surgical point-probe spectroscopy devices for fluorescence detection currently allow single-point, for example a 1 mm$^2$, spectrally-resolved fluorescence detection that may or may not measure fluorescence quantitatively.

SUMMARY

An imaging system, such as a surgical microscope or endoscope, includes an illumination device for illuminating a target with light selectable from patterned white light and specific wavelengths of light. The system receives light from the target and images the light hyperspectrally, in an embodiment using a hyperspectral imaging array, and in an embodiment using tunable filters for passing a filtered portion of the received light to an imager. Embodiments construct a 3-D surface model of the target from, in an embodiment stereo images and in another embodiment structured-light images, and processes images taken in patterned white light to estimate optical properties of the target. Hyperspectral images taken under specific wavelengths of light are displayed as fluorescent images, and corrected for optical properties of tissue to provide quantitative maps of fluorophore concentration. Spectral information from the hyperspectral images is processed to provide images with depth information of fluorophore concentration. The images are displayed to a surgeon for use in surgery In another embodiment, an optical and image processing system has a white light source coupled to pass light through a bandpass optical filter forming filtered light; a spatial modulator coupled to modulate light from the light source, forming modulated light; projection apparatus configured to project onto tissue light selected from the group consisting of filtered light and modulated light; a hyperspectral camera configured to receive light from tissue; and an image processing system coupled to receive images from the hyperspectral camera and configured with a memory containing machine readable instructions for performing at least a function selected from the group consisting of quantitative fluorescent imaging, depth resolved fluorescent imaging, and hemoglobin oxygen saturation imaging.

BRIEF DESCRIPTION OF THE DRAWINGS

The features and advantages of the invention will be apparent from the particular description of embodiments of the invention, as illustrated in the accompanying drawings in which the drawings are not to scale, emphasis instead being placed upon illustrating the principles of the invention.

FIGS. 1A, and 1B represent alternative forms of hyperspectral camera for the system of FIG. 1.

FIGS. 1C and 1D represents a stimulus light source for use in the system of FIG. 1.

FIG. 1E represents a spatially modulated light source for use in the system of FIG. 1.

FIG. 19 is an introduction to data flow diagrams for depth-resolved fluorescent imaging (dFI), and in particular favoring fluorophores in the visible spectrum range.

FIG. 20 is a data flow diagram for a non-model-based technique of depth-resolved fluorescent imaging.

FIG. 21 is a data flow diagram for a model-based technique of depth-resolved fluorescent imaging.

FIG. 23 is a data flow diagram for a non-model-based technique of depth-resolved fluorescent imaging.

FIG. 24 is a data flow diagram for a model-based technique of depth resolved fluorescent imaging.

DETAILED DESCRIPTION OF THE EMBODIMENTS

A hyperspectral imaging device is an imaging device that is capable of resolving wavelengths of received light into signals representing multiple discrete wavelength bands, but which resolves wavelengths into more than the traditional color-cameral three overlapping primary color wavelength bands (red, green, and blue) at each pixel, or macropixel, of a received image. Such a hyperspectral imaging device may in some embodiments resolve wavelengths into more and narrower wavelength bands, by separately resolving intermediate colors such as yellow or orange into their own wavelength bands. A hyperspectral imaging device may also cover a broader range of the electromagnetic spectrum than visible light alone, such as by covering both visible and portions of the infrared light spectrum; some hyperspectral imaging devices are capable of resolving received infrared light into signals representing intensity of light received within each of a large number of separate wavelength bands including multiple bands within the infrared spectrum. Some hyperspectral imaging devices provide a spectrum at each pixel, or macropixel, of each image received; others may provide images having intensity information only within a selection of multiple, predetermined, wavelength bands. A wide-field hyperspectral imaging device is capable of acquiring full field of view images of the region of interest, such as the surgical field of view, similar to broad beam fluorescence imaging devices used for wide field imaging Our hyperspectral imaging device is capable of selecting wavelengths of interest in the visible and infrared regions of the electromagnetic spectrum, and as such capable of acquiring multiple images at wavelengths of interest, using pixel by pixel full spectra reconstruction using multiple images acquired at wavelengths of interest. In a "snapshot" embodiment our device resolves light into 32 or 64 predetermined colors or wavelength bands, and in a tunable-filter embodiment, into 100 or more wavelength bands.

Figure 1:
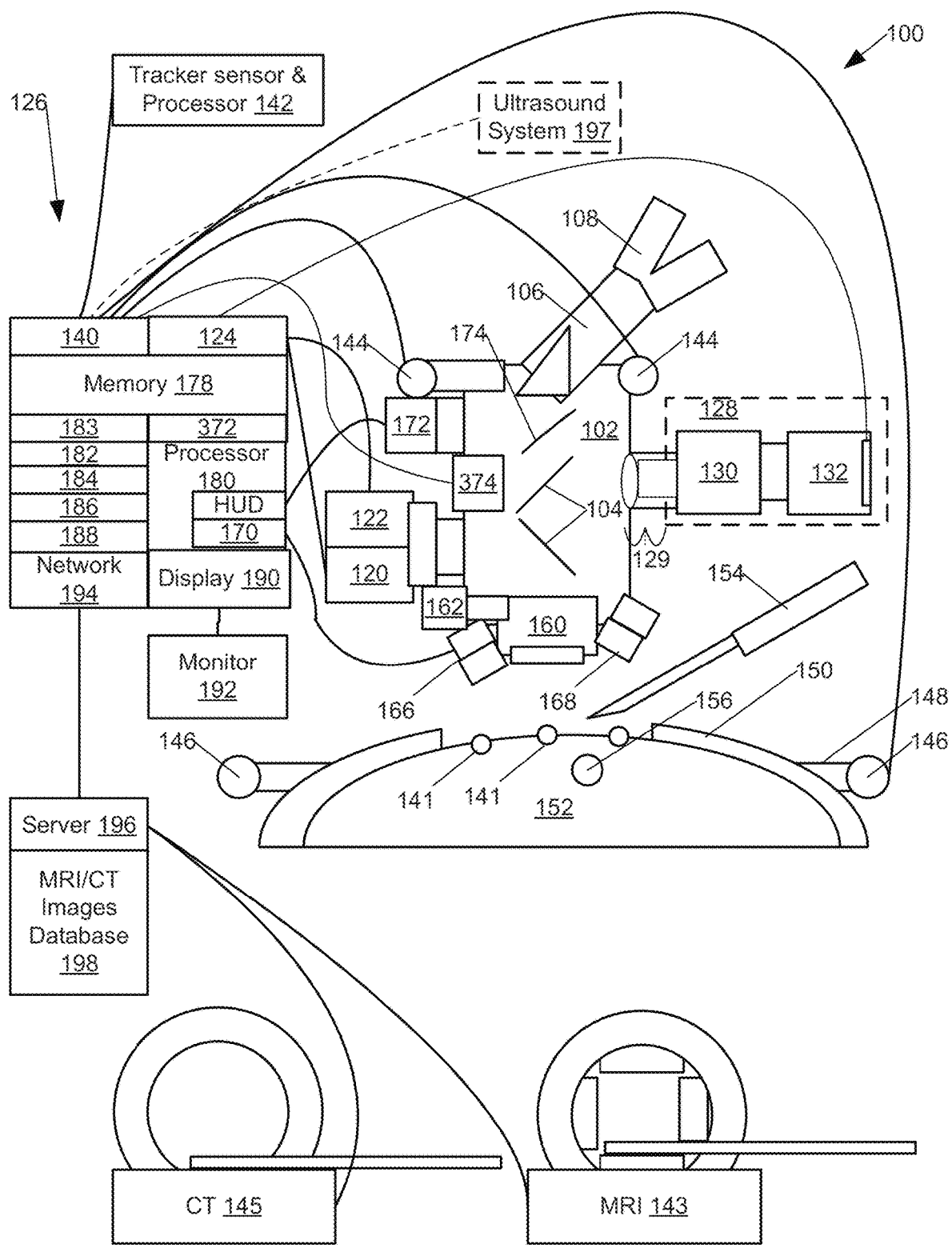
FIG. 1 is a diagram of one exemplary system for assisting a surgeon in locating structures in soft tissues during surgery, in an embodiment.

FIG. 1 illustrates a system 100 for supporting surgery, according to some embodiments.

The system of FIG. 1 includes a microscope body 102, which has multiple beam splitters 104 that permit light to be diverted to several optical ports simultaneously or alternatively in succession, depending on the microscope and operator preferences. Attached to a first optical port of body 102 is a tube 106 leading to a surgeon's binocular optical eyepieces 108.

Attached to a second optical port of body 102 are a first high definition electronic camera 120 and a second high definition electronic camera 122. Cameras 120, 122 are coupled to provide images to image capture interface 124 of a digital image processing system 126. Attached to a third optical port of body 102 is a hyperspectral imaging device 128 that in an embodiment has a tunable filter 130 adapted to receive light from body 102 and a high resolution broad-bandwidth electronic camera 132. In a particular embodiment, hyperspectral imaging device 128 couples to body 102 through a flexible, coherent, fiber-optic image-conveying, optical cable 129. The camera 132 of the hyperspectral imaging device 128 is also coupled to provide images to image capture interface 124 of the digital processing system 126. In an embodiment, tunable filter 130 is a liquid crystal tunable filter. In an alternative embodiment, tunable filter 130 is an acousto-optic tunable filter.

Referring again to FIG. 1, a tracker interface 140 of the image processing system 126 is coupled to use tracking sensors 142 attached to a reference location within an operating room to track relative locations of microscope location sensors 144 and patient location sensors 146. In an embodiment, tracking sensors 142 and an associated processor of tracker interface 140 are a commercially available Treon® StealthStation®, (trademarks of Medtronic, Louisville, Colo., USA) optical tracking system. Microscope location sensors 144 are rigidly attached to the microscope body 102, and patient location sensors 146 are attached to a frame 148 that may be attached to a patient while the patient is undergoing a surgical procedure. In a particular embodiment, frame 148 is adapted to be attached to a patient's skull 150 by screws (not shown) for the duration of a neurosurgical procedure during which the patient's brain 152 is exposed, and during which patient's brain 152 may be operated on with surgical instruments 154 to remove or destroy one or more lesions 156.

Microscope body 102 also has zoom optics 160, adapted for operation by a zoom motor/sensor 162, and a focus adjustment (not shown) adapted for operation by a focus motor (not shown). The microscope also has multiple illuminators 166, 168. In an embodiment, illuminators 166 include white-light illuminators 166, and wavelength-selective fluorescent stimulus illuminators 168, operating under control of an illumination interface 170 of the image processing system 126. The microscope body also has a heads-up display (HUD) projector 172 capable of providing graphical images through a combiner 174 of body 102 such that the graphical images are presented for viewing by a surgeon through surgeon's eyepieces 108. The surgeon's field of view through the operating microscope and its associated HUD is co-registered with that of the imaging system, allowing display of tissue classifications, mapped tumor locations, and hyperspectral imaging results superimposed on visible brain tissue, one-to-one comparisons, and intraoperative surgical decision making. At standard working distances between microscope and surgical cavity, surgical instruments 154 fit between zoom optics 160 and tissue of brain 152.

Image processing system 126 also has a memory 178 into which image capture interface 124 saves images received from cameras 120, 122, 132; and at least one processor 180. Processor 180 is adapted for executing processing routines such as surface fluorescence quantification imaging qFI, fluorescence depth modeling routines 186 and both depth-resolved fluorescence imaging (qFI) and quantitative depth-resolved fluorescence imaging (qdFI), endogenous biomarker quantification using spatial frequency domain techniques (see below) and hyperspectral image processing routines 188 stored in memory 178 and operable on images stored in memory 178. Processor 180 is also adapted for preparing images for display through display interface 190 onto monitor 192, and for communicating through network interface 194 to server 196; server 196 has database 198 containing information derived from preoperative MRI and CAT scans.

Server 196 is also interfaced through a network to an MRI scanner 143 as known in the medical imaging art that provides preoperative images of a patient's brain 152, including surface features 141, and tumor 156, prior to prepping the patient for surgery and opening the patient's skull 150 (brain 152, tumor 156, surface features 141 are shown with patient prepared for surgery and skull opened). Server 196 is also interfaced through a network to a CT scanner 145 that is capable of imaging a patient's brain prior to prepping the patient for surgery and opening the patient's skull 150.

While the system of FIG. 1 is illustrated in context of an operative microscope, we anticipate that our surgical vision enhancement system may be constructed in any of several other formats useful in the surgical art, including a laparoscope format and an endoscope system. For example, a laparoscopic system 280 (FIG. 1G) may have a coherent optical-fiber bundle 282 having a light-source-and-camera end 286 and a scope end 287. The light source and camera end 286 is coupled through a beamsplitter 288 to a combined stimulus and broad spectrum light source resembling that of FIG. 1F, and beamsplitter 288 is also coupled to an infrared and visible light hyperspectral camera 294 resembling that of FIG. 1A. A combined projection and imaging lens 290 both projects spatially modulated light of desired wavelengths from scope end 287 of fiber bundle 282 onto tissue 292, and images both fluorescent and backscattered light onto fiber bundle 282 and thus into camera 294. A digital image processing system 126, similar to that of FIG. 1, is provided to receive, record, and process images from the hyperspectral camera 294 and to drive the digital multimirror device of the spatial modulator 268 with predetermined spatial-light patterns.

Operation of the system 100 has several modes, and each mode may require execution of several phases of processing on processor 180, executing one or more of several routines, as mentioned above. Computational efficiency and high performance are desirable in processor 180, since it is desirable to minimize the operative time for which a subject is anesthetized.

For example, processor 180 executes the hyperspectral image processing routine to perform the hyperspectral fluorescence and reflectance imaging of the tissue, as described herein. Processor 180 executes hyperspectral, reflectance, and in some embodiments spatially modulated light, image processing to determine optical properties of the tissue, processor 180 then executes qFI (quantified fluorescence imaging) routines to correct fluorescence images for quantification of surface and near-surface fluorophores imaged in fluorescence images. The processor 180 also uses the hyperspectral camera 128 to capture a hyperspectral fluorescent image stack and executes dFI (depth-resolved fluorescent imaging) and/or qdFI (quantified depth-resolved fluorescent imaging) routines from memory 178 to process the hyperspectral fluorescent image stack to map depth and quantity of fluorophore in tissue. The hyperspectral fluorescence and reflectance imaging may also be performed in connection with stereo-optical extraction routines executed on processor 180, using images captured by stereo cameras 120, 122, to perform tissue surface contour and feature extraction for light transport modeling in qFI, dFI & qdFI and tomographic display of mapped depth and quantity of fluorophore. In an embodiment the hyperspectral fluorescence and reflectance image processing is performed on processor 180 in connection with fluorescence depth modeling, as described in U.S. patent application Ser. No. 13/145,505, filed in the United States Patent and Trademark Office on Jul. 2, 2011, and U.S. Provisional Patent Application 61/588,708, filed on Jan. 20, 2012 and incorporated herein in its entirety by reference, and as described herein, where fluorescence and reflectance spectral information is derived from hyperspectral imaging device 128. In an alternative embodiment the hyperspectral fluorescence and reflectance image processing is performed by processor 180 executing depth-resolved fluorescent imaging routines as described in the unpublished paper A Non-Model Based Optical Imaging Technique For Wide-Field Estimation Of Fluorescence Depth In Turbid Media Using Spectral Distortion submitted herewith as an attachment, and as described in PCT/US13/22266 filed Jan. 18, 2013, which claims priority to (523259) 61/588,708 filed Jan. 20, 2012, both of which are included herein by reference.

In some embodiments, an optional ultrasound system 197 is provided to map deep brain structures using medical ultrasound as known in the art. In some embodiments, information from the ultrasound system 197 is coregistered with information from the stereo optical system herein described and jointly used for modeling shift of deep brain tumors and structures, particularly where surgical cavities exist and/or surgical instruments, such as retractors, are present in a surgical site.

In an alternative embodiment, with reference to FIG. 1A hyperspectral imaging device 128, which may optionally couple to microscope body 102 through optical cable 129, has a lens system 131 adapted for focusing images, a dichroic filter 133 adapted for separating light into shorter wavelength light and longer wavelength light, and, for imaging the shorter wavelength light, a short wavelength tunable optical filter 135 and image sensor 137. Light received from optic cable 129 enters imaging device 128 through a dichroic filter-changer 136 having a neutral-density filter and notch filters adapted to exclude stimulus-wavelength light. Also provided, and coupled to image the longer wavelength light, are a long wavelength tunable optical filter 139 and longer wavelength image sensor 138. Each tunable optical filter 135, 139 is a bandpass filter, in a particular embodiment with a three nanometer bandpass, and is tunable from 400 to 1000 nanometers wavelength, and image sensor 137. 138 are broadband sensors as known in the optoelectronics art; in a particular embodiment short wavelength image sensor 137 is a CMOS (complementary metal oxide semiconductor) or CCD (charge coupled device) image sensor, while longer wavelength sensor 138 is a high-sensitivity electron-multiplying CCD image sensor. Tunable optical filters are coupled to, and controlled by, processor 180 such that they may be set to a desired wavelength by processor 180.

In an alternative embodiment, with reference to FIG. 1B hyperspectral imaging device 128, which may optionally couple to microscope body 102 through optical cable 129, has a lens system 131 adapted for focusing images and a photosensor device 199 having an rectangular array of tiling patterns of photosensors, such as tiling pattern 127, where each tiling pattern corresponds to a pixel of a captured image. Unlike typical Bayer-pattern 3-color cameras, in an embodiment, each tiling pattern 127 has a rectangular pattern of sixteen, thirty-two, or sixty-four, or other rectangular pattern, of photosensors each of which has a color filter over it; while a selected few of the color filters are traditional red, green, and blue color filters adapted for generating a coregistered traditional color image, the remaining color filters are Fabry-Perot interference filters of differing thicknesses such that photosensor device 199 has a separate photosensor in each tiling pattern sensitive to each of N specific, preselected, wavelengths between 1000 and 400 nanometers; for N 13, 29, or 61 for a total number of photosensors per pattern of 16, 32, or 64. In alternative embodiments, the tiling pattern may have a different number of photosensors. Photosensor arrays with tiling patterns of integrated Fabry-Perot interference filters of multiple wavelengths over photosensors are expected to be available from IMEC vzw, Kapeldreef 75 3001 Leuven, Belgium in late 2013. Using a tiled photosensor array having a well-chosen selection of filters allows video-rate image collection of hyperspectral image cubes.

In an embodiment, as illustrated in FIG. 1C, fluorescent stimulus light source 168 has an intense, broadband, white light source such as a supercontinuum laser 230 arranged to project light through a tunable filter 232 having bandpass of 3 to 10 nanometers, and tunable for a bandpass center over the range 400 to 1100 nanometers wavelength. Wavelength-selected light passed from laser 230 through filter 232 is focused by lens 234 onto tissue 152. Tunable filter 232 is electrically tunable, and is coupled to, and controlled by, processor 180. In a particular embodiment, filter 232 is a tunable Lyot filter.

In an alternative embodiment, illustrated in FIG. 1D, fluorescent stimulus light source 168 has several light-emitting diodes (LEDs) 251, each of which has a different emissions spectrum, each LED being coupled through a bandpass filter 253; in a particular embodiment light-emitting diode and filter pairs are provided such that the light source 168 can be configured to provide light of violet 390 nm, blue 438 nm, cyan 475 nm, teal 512 nm, green 542 nm, yellow 586 nm, and red 631 nm wavelengths. A wavelength or wavelengths provided at any one time is determinable by driving only selected LEDs of LEDs 251. Light from bandpass filters 253 is combined into a single beam by combiner 255, and a lens 257 is provided to adjust beam shape.

In an embodiment, a combination white and fluorescent-stimulus light source 260 (FIG. 1F) capable of providing both unpatterned and spatially modulated light at either a selected stimulus wavelength or at a broadband white wavelengths is coupled to a lighting port of the microscope to illuminate tissue. In a particular embodiment, light source 260 has paired LEDs 251 and filters 253 adapted to provide selected wavelengths of stimulus light similar to those of the embodiment of FIG. 1D, and a controllable white light source 262, such as a supercontinuum laser or xenon incandescent lamp. Light from one or more active light sources such as a selected LED 251 and filter 253, or an active white light source 262, is combined by combiner 264 and provided to a spatial modulator 268; in a particular embodiment spatial modulator 268 is a digital multimirror device (DMD) capable of modulating light under control of a display controller 270 with any of thousands of spatial illumination patterns, including an unmodulated pattern. In other embodiments, spatial modulator 268 may incorporate a digitally-controlled liquid-crystal display and a display controller 270, or may incorporate a slide-changer or film-transport device adapted to interpose selected film frames having spatial modulation patterns on them. Modulated light from spatial modulator 268 then passes through one or more lenses 272, which may include a coherent fiber bundle, for transmitting and focusing the modulated light onto tissue.

In an embodiment, white light illuminator 166 has a high-intensity, broadband, white light source such as a supercontinuum laser 236 or other lamp arranged to project light onto a mirror of an digital-micromirror projection device (DMD) 238 such those produced by Texas Instruments for use in digital projectors for computer graphical display and for use in digital projection televisions. Light from DMD 238 is projected by a lens system 240 onto tissue 152. DMD 238 is equipped with DMD control electronics 242 as known in the art of digital projectors, and is coupled to an additional graphical display controller (not shown) of digital image processing system 180. The arrangement of laser 236, DMD 238, lens 240, control electronics 242, display controller, and digital image processing system is capable of projecting either unpatterned light or a predetermined black-and-white pattern or image of light onto tissue 152.

System Functions

Figure 2:
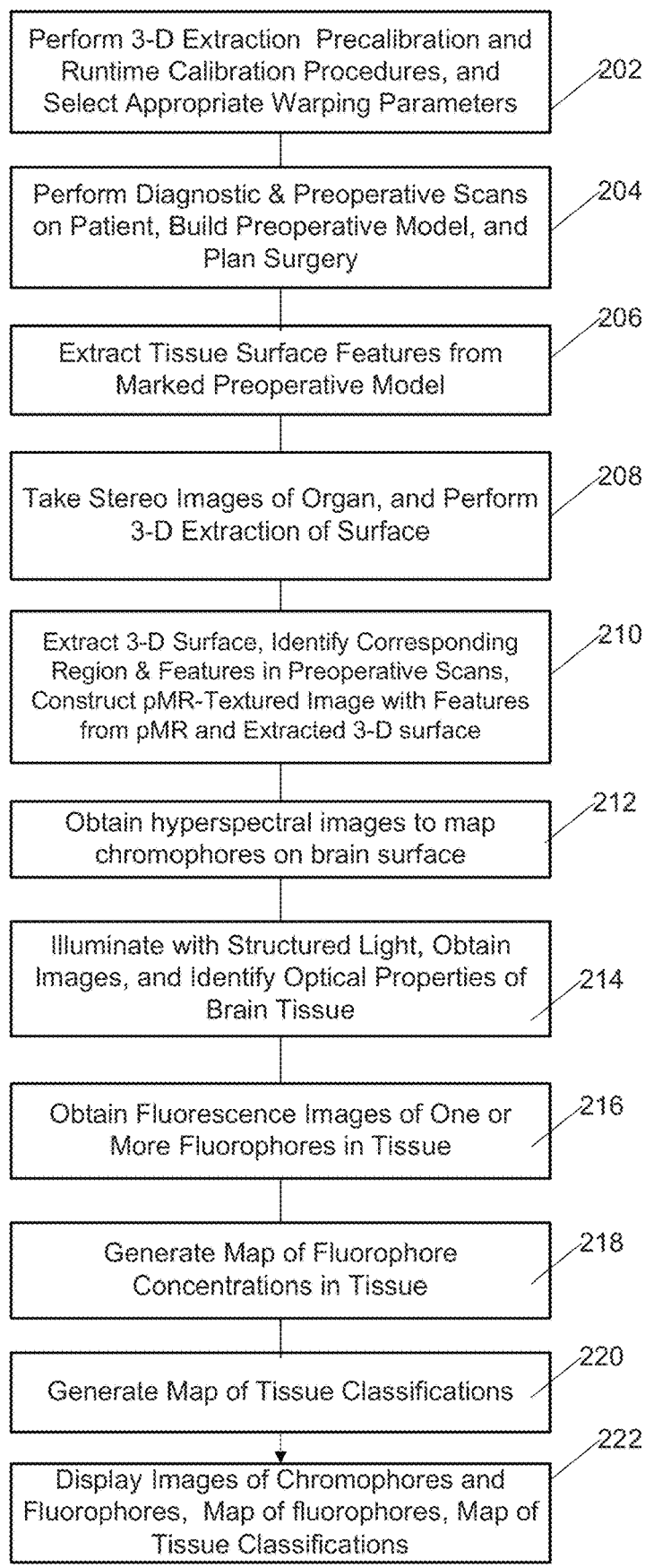
FIG. 2 is a flowchart of one exemplary method for determining locations of structures in soft tissues during surgery, in an embodiment.
Figure 3:
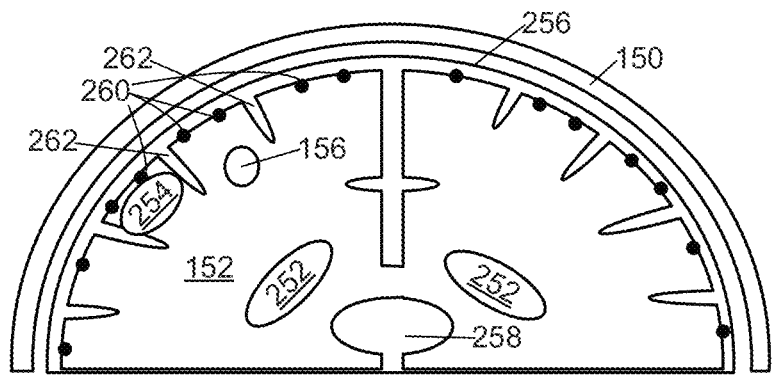
FIG. 3 shows a cross-sectional illustration of a brain, such as a human brain, with skull and meninges.

Surgical applications of the system are described with reference to brain surgery; however the system is applicable to surgery on other organs as well. In a brain surgery situation patients are prepared, the system is operated, and surgery performed, according to the flowchart of FIG. 2. The system of FIG. 1 is prepared and calibrated 202 for proper three-dimensional surface extraction, according to the procedure outlined below. FIG. 3 shows a cross-sectional illustration of the brain 152 of FIG. 1, showing skull 150 and meninges. FIGS. 1, 2, and 3, are best viewed together with the following description.

The patient is subjected to appropriate diagnostic and pre-operative MRI (Magnetic resonance Imaging) (pMR) and/or CT (Computed Tomography X-ray) (pMR) scans. These pMR scans provide a preoperative three-dimensional model of tissue of the patient, in a particular embodiment the tissue of the patient includes the patients' brain 152 (FIG. 1 and FIG. 3). A surgeon performs preoperative planning 204, which includes identifying lesion tissue, such as tumor tissue 156, as targeted tissue for removal in the preoperative model of the tissue. The preoperative planning may also include identifying other important structures 252, such as particular blood vessels, nerve tracts, nearby areas critical for particular functions such as Broca's area 254, and other nearby structures that the surgeon desires to preserve during operation. The tumor tissue 156 targeted for removal, and other important structures 252, 254 that are desired to be preserved, are marked in the preoperative model at their locations as provided in the preoperative scans, indicating their respective locations before surgery begins. The preoperative model established from preoperative scans are detailed and visualize some brain surface structures, such as blood vessels 260, and sulci 262; sulci (plural of sulcus) are creases or folds at the surface of the brain. The surface of the dura is presumed to be at the surface of the brain as shown in the pMR model and scans. A model of the surface of the brain is extracted from the pMR model and scans. The pMR model is in a patient-centered coordinate system.

Figure 4:
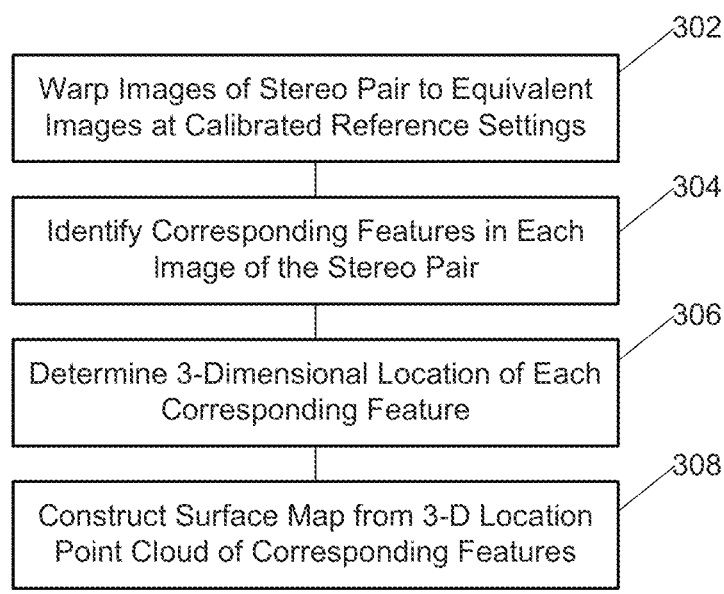
FIG. 4 is an exemplary flowchart of a method for determining a three dimensional surface map, in an embodiment.
Figure 5A:
FIG. 5A shows a pre-durotomy surface map annotated with features from the pMR model.
Figure 5B:
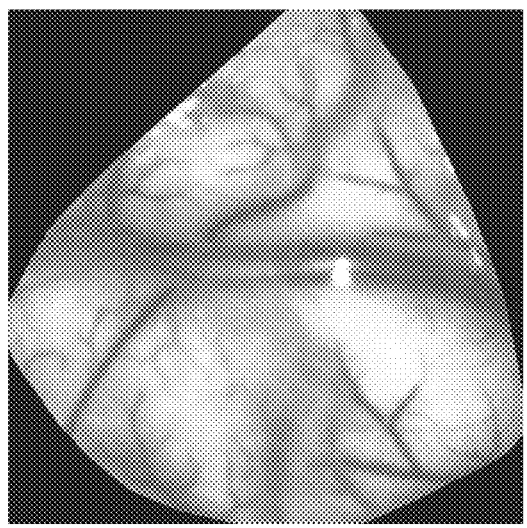
FIG. 5B shows a post-durotomy surface map.

Once consent is obtained, the patient is prepared for surgery, and patient tracking sensors 146 are attached to the patient's skull. In some embodiments, fiducials are used to provide registration marks in preoperative and intraoperative imaging to ease registration of the pMR coordinate system to intraoperative imaging. The patient tracking sensors are registered to the patient-centered coordinate system of the pMR model. Positions of the patient tracking sensors are determined in the patient-centered coordinate system, and the patient's skull 150 is opened, exposing the dura 256 matter. Dura is opened. The microscope zoom optics 160 and focus are set to a desired runtime optical setting, and the microscope body 102 position is adjusted such that it is over the surgical wound and a field of view of the microscope includes brain tissue 152 over the tumor 156. The microscope location and orientation is tracked relative to the patient using tracking sensors 142, microscope location sensors 144 and patient tracking sensors 146 to register a focal plane of the microscope to the pMR coordinate system and pMR images. These sensors, and/or fiducials, may also be used to register intraoperative imaging of other modalities, such as X-Ray, CT or MRI, to the pMR coordinate system. A first pair of stereo images is then taken 208. Once taken, this first pair of stereo images is then processed using any features visible on the brain surface as follows:
  a) Stereo visual surface extraction (FIG. 4) is performed of the dural surface in the images to create a brain surface map by
     1) Warping 302 the images to equivalent images as if taken at the reference settings;
     2) Identifying 304 corresponding features in both warped images;
     3) Tracing rays from the corresponding features to determine 306 three-dimensional locations of those features, the 3-dimensional locations forming a point cloud;
     4) Constructing 308 an extracted dural surface map from the point cloud of three-dimensional locations; and
     5) Transforming the extracted brain surface map to the patient-centered coordinate system of the pMR model by applying any necessary rotations and translations.

After a hyperspectral image stack is obtained and processed as described below under Hyperspectral Reflectance Imaging Mode by illuminating the brain surface with unpatterned or spatially unmodulated light, and/or a sequence of patterns of spatially structured white light from illuminator 166, and photographing the surface with hyperspectral camera 128, the image stack is processed by processor 180 to generate a map of absorption & scattering light transport parameters and chromophores of interest, such as oxygenated and deoxygenated hemoglobin, on or in the brain surface. These map images may be displayed.

Processor 180 provides DMD spatial modulator 238 of white light illuminator 166 with a sequence of patterns for spatially modulated light, where the spatially modulated light is projected onto tissue 152. A series of images of the brain is obtained 214 with each pattern of illuminating light at wavelengths of interest, including both stimulus and fluorescence wavelengths for a fluorophore that is expected to be present in tissue 152. In particular embodiments, the subject has been administered appropriate medications such that tissue 152 contains one or more of protoporphyrin IX generated in tissue by metabolizing aminolevulinic acid, fluorescein or a fluorescein-labeled molecule such as an antibody, or indocyanine green or an indocyanine green-labeled molecule such as an antibody. In alternative embodiments other fluorophores may be used. These images are processed to estimate optical properties of tissue 152 in each voxel of tissue for improved quantification of fluorophore concentration and depth localization of fluorophores.

As described below under Fluorescent Imaging Mode, the brain is illuminated with one or more stimulus wavelengths for the fluorophores, and images are captured 216 at one or more emissions wavelengths. In two-dimensional embodiments a two-dimensional map of fluorophore distribution is constructed 218, and corrected using the estimated optical properties for quantification of fluorophore. In three-dimensional embodiments, a three-dimensional map of fluorophore distribution in tissue is constructed 218, as described below with reference to Fluorescent Depth-Resolved Imaging Mode, or in other embodiments as described below with reference to Fluorescent Quantitative Depth-Resolved Imaging Mode, which includes use of the estimated optical properties for quantification of fluorophore concentrations. In an embodiment, the map describes fluorophore concentrations at up to one centimeter deep in the brain, or deeper in some other types of tissue such as breast tissue. This map is then combined with the extracted 3-dimensional surface model, and topographic or tomographic images of fluorophore concentration are displayed. In a particular embodiment, where two fluorophores are used, difference maps are also prepared indicating differences in concentrations between the two fluorophores, and these maps are displayed.

A classifier, which in embodiments is one of a k-nearest-neighbors (kNN) classifier, a neural network classifier, and an support vector machines (SVM) classifier, is then used to classify 220 (FIG. 2) tissue at each voxel, and thereby generate a map of tissue classifications up to one centimeter deep in the brain surface. The classifier operates on chromophore concentrations, including oxygenated and deoxygenated hemoglobin and ratios of oxygenated to deoxygenated hemoglobin, fluorophore concentrations, and optical properties as determined for that voxel. Finally, the images and generated maps are displayed.

Calibration for 3-D Surface Extraction

Calibration of the stereo surface mapping and its operation are as described in patent application "Method and Apparatus for Calibration of Stereo-Optical Three-Dimensional Surface-Mapping System" number PCT/US13/20352 filed 4 Jan. 2013, and its parent documents, the contents of which are incorporated herein by reference.

Stereovision Calibration and Reconstruction

Figure 6:
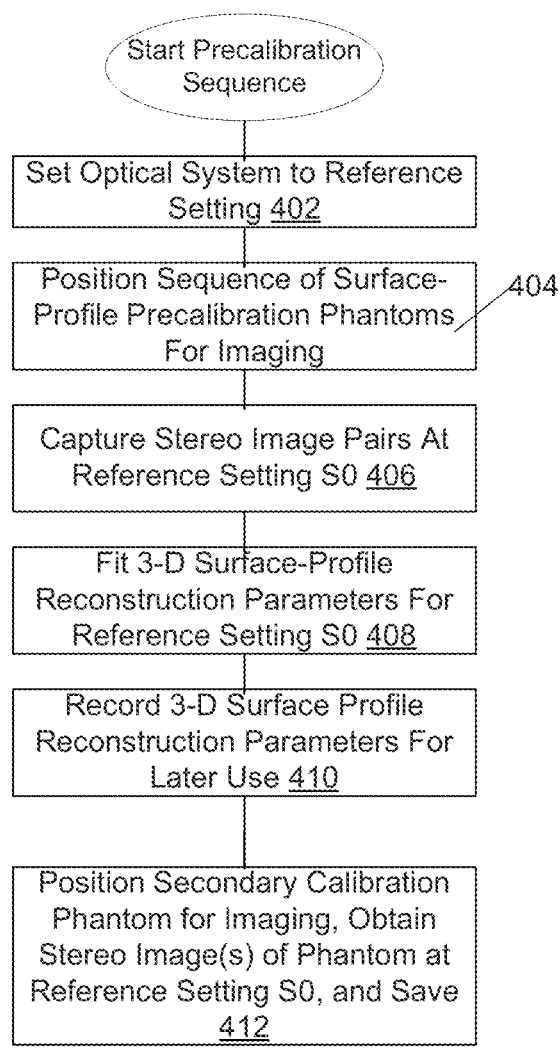
FIG. 6 is a flowchart of a precalibration procedure for determining a 3D surface map.
Figure 7:
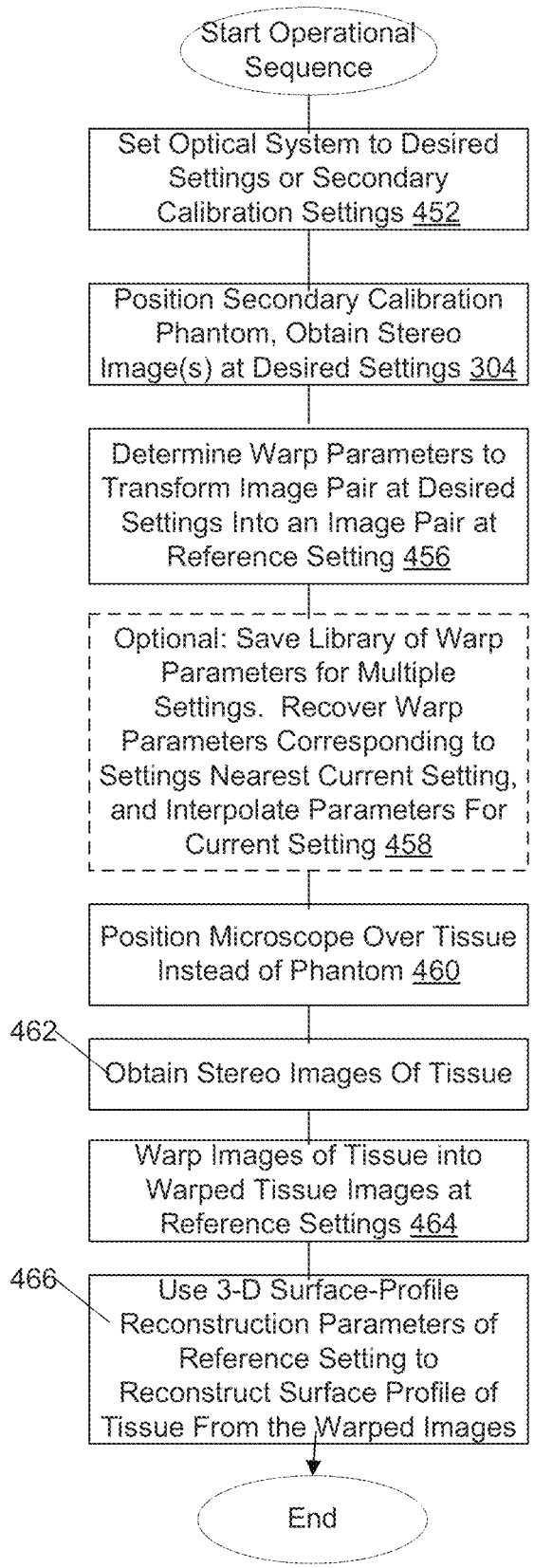
FIG. 7 is a flowchart of secondary calibration procedure for determining a 3D surface map, and modeling tumor location.

The surface profile extraction system uses a stereo optical system, such as that illustrated in FIG. 1 or 1A. With reference to FIG. 6, the optical system is set 402 to a reference setting S0 of a set of one or more reference settings. A sequence of optical precalibration phantoms are positioned 404 in view of the system, having known surface profiles, and parameters for reconstruction surface profile extraction routine 182 are derived that are sufficient for reconstructing a surface profile from a pair of stereo images taken with the optical system set 402 to the reference setting.

Techniques for stereo image calibration and reconstruction based on a pinhole camera model and radial lens distortion correction are outlined here for completeness, and are used in some embodiments. A 3D point in world space (X,Y,Z) is transformed into the camera image coordinates (x,y) using a perspective projection matrix:

$$\begin{pmatrix} x \\ y \\ 1 \end{pmatrix} = \begin{pmatrix} \alpha_x & 0 & C_x & 0 \\ 0 & \alpha_y & C_y & 0 \\ 0 & 0 & 1 & 0 \end{pmatrix} \times T \times \begin{pmatrix} X \\ Y \\ Z \\ 1 \end{pmatrix} \quad (1)$$

where $\alpha_x$ and $\alpha_y$ incorporate the perspective projection from camera to sensor coordinates and the transformation from sensor to image coordinates, $(C_x, C_y)$ is the image center, and T is a rigid body transformation describing the geometrical relationship of the effective optical centers between the views of the two cameras, 120, 122.

A precalibration phantom is prepared having reference marks at known positions in 3D space. A stereo pair of images is taken 406 of the precalibration phantom, assuming the precalibration phantom has known surface profile, providing a plurality of known points in three dimensions. A total of 11 camera parameters (6 extrinsic: 3 rotation and 3 translation; and 5 intrinsic: focal length, f, lens distortion parameter, k1, scale factor, Sx, and image center, (Cx, Cy)) are then determined through precalibration using a least squares fitting approach, and saved for later use as herein described. The intrinsic parameters include f focal length, κ•lens distortion coefficient, Sx non-square pixel scalar, Cx; Cy camera center. The extrinsic parameters include R(μx; μy; μz) rigid-body rotation, T(tx; ty; tz) rigid-body translation. Note that we now have a camera model that projects a point in the world to its image coordinates, the next step is to determine (i.e., calibrate) several unknown parameters among the equations presented above. In particular, the extrinsic camera parameters to be calibrated are the rotation and translation matrices (R; T) and the intrinsic parameters are the focal length (f), lens distortion coefficient •, scale factor (Sx), and image center (Cx; Cy).

The 3D precalibration phantoms have easily identified correspondence points or reference marks, where the correspondence points have known height relative to a phantom baseline. Each correspondence point should be identifiable in each of the images of the stereo pair.

Stereo image rectification is performed in a method similar to that of Hai Sun, pages 38-47.

Stereo image rectification is employed next to establish epipolar constraints that limit the search for correspondence points along "epipolar lines" (defined as the projection of the optical ray of one camera via the center of the other camera following a pinhole model). In addition, images are rotated so that pairs of epipolar lines are collinear and parallel to image raster lines in order to facilitate stereo matching. In an embodiment, an intensity-based correlation metric and a smoothness constraint aware used to find the correspondence points in both images of the pair. Each pair of correspondence points was is then transformed into their respective 3D camera space using the intrinsic parameters, and transformed into a common 3D space using the extrinsic parameters. Together with their respective camera centers in the common space, two optical rays were constructed with their intersection defining the 3D location of each of the correspondence point pair.

Since the 3D locations of the correspondence points are known on the precalibration phantoms, the parameters are fit 408 such that the extraction to a common 3D space gives results where extracted 3D points of an effective surface profile of the precalibration phantom match heights of the known points on the precalibration phantom. These 3D surface profile extraction parameters are then saved 410 for later use below.

Next, and not disclosed in Hai Sun, a secondary calibration phantom is positioned 412 in view of the optical system, and a stereo image pair of the runtime calibration phantom as viewed in the reference setting is captured and saved as part of calibration information. In an embodiment, the secondary calibration phantom is a two dimensional, flat, phantom having marks printed thereon. In an embodiment, the marks printed on the runtime calibration phantom are randomly generated squares of random intensities. In an alternative embodiment for use with cameras in aircraft or drones, the secondary calibration phantom is a particular, preselected, field or town. When it is desired to use the system to extract a surface profile of tissue 152, the optical system is set to an arbitrary runtime setting, typically having at least some optical system parameters, such as optical magnification, differing from those for the reference setting. The secondary calibration phantom may be used to calibrate warping parameters for the runtime setting, or may be used to calibrate warping parameters for secondary calibration points stored in a library or table as described below; a calibration for the arbitrary runtime setting determined by interpolation into the table and used for 3D surface extraction. Calibration of settings performed using the secondary calibration phantom, whether used for a runtime setting or for determining secondary calibration points, is described herein as secondary calibration.

Secondary Calibration

With the optical system set 452 to the arbitrary desired setting, the secondary calibration phantom is positioned in view of the optical system in a position approximating that where tissue 152 will be present during surgery, and a stereo image pair of the secondary calibration phantom is captured or taken 454 by cameras 120, 122 taken through the optical system with the optical system configured at secondary calibration setting S.

Next, deformation field parameters DFP for image warping routine 183 are derived 306 such that application of image warping routine 183 to the stereo image pair of the phantom with optical system at desired setting S provides a deformed stereo image pair that closely matches the stereo image pair of the secondary phantom as taken with the optical system in the reference setting S0.

The method for 3D surface extraction herein described warps stereo images captured using a desired setting S, using the deformation field obtained from images of a phantom at desired setting S and reference setting S0, into warped images corresponding to images taken at the reference setting S0. Because the reference setting S0 has been calibrated for surface extraction, the warped stereo images can then be used for surface reconstructing following the same calibration as determined for reference setting S0. The key to the technique is to find the equivalent image at a specific setting S0 that has been pre-calibrated for an image acquired at an arbitrary setting S.

Image Deformation Due to the Change in Image Acquisition Settings and Target Surface Orientation To determine image deformation due to the change in image acquisition settings (i.e., m magnification and f focal length), in an experimental embodiment a series of phantom images were acquired using a planar secondary calibration phantom with randomly generated squares of random grayscale intensity by successively changing one parameter from its reference value while maintaining other optical system parameters at the corresponding reference value; in other embodiments other secondary calibration phantoms may be used. In an embodiment, the reference values of image magnification (m0) and focal length (f0) correspond to the lowest magnification and the shortest focal length that the microscope offers, respectively. Because image magnification alters the image acquired independently from the change in focal length (f) or viewing angle ($\theta$) (which was verified with the deformation fields generated by changing m at different f and $\theta$), only one set of images is necessary to determine an image deformation field due to the change in m (acquired with f0). With m0, image deformation due to the change in f was also determined by successively increasing f from f0. For these phantom images, the secondary calibration phantom was perpendicular to an optical axis centered between the effective optical axes of the two cameras.

Figure 8:
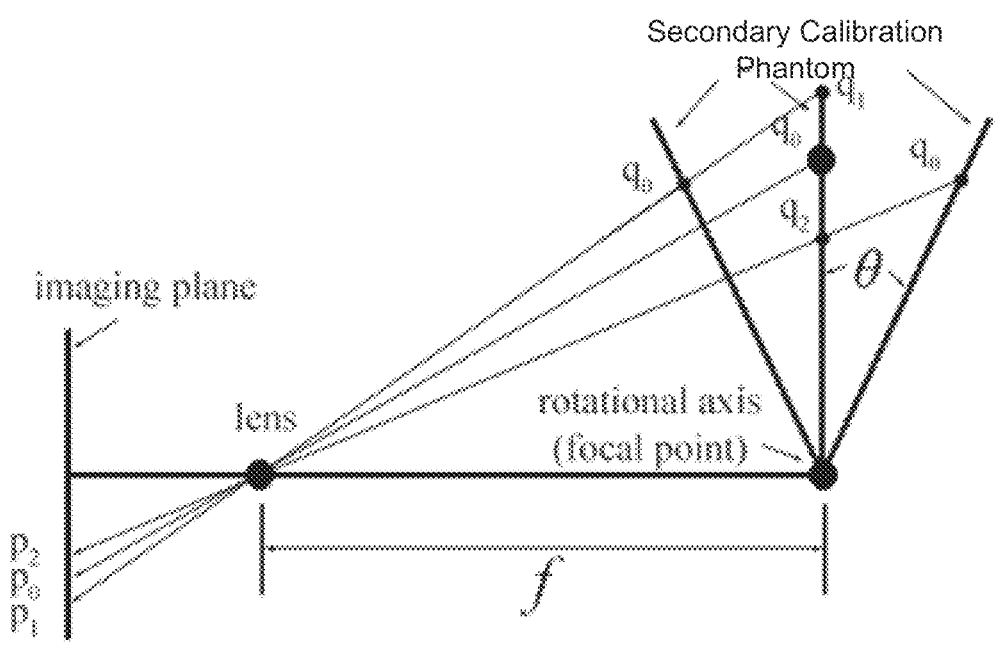
FIG. 8 is an illustration of secondary calibration
Figure 10:
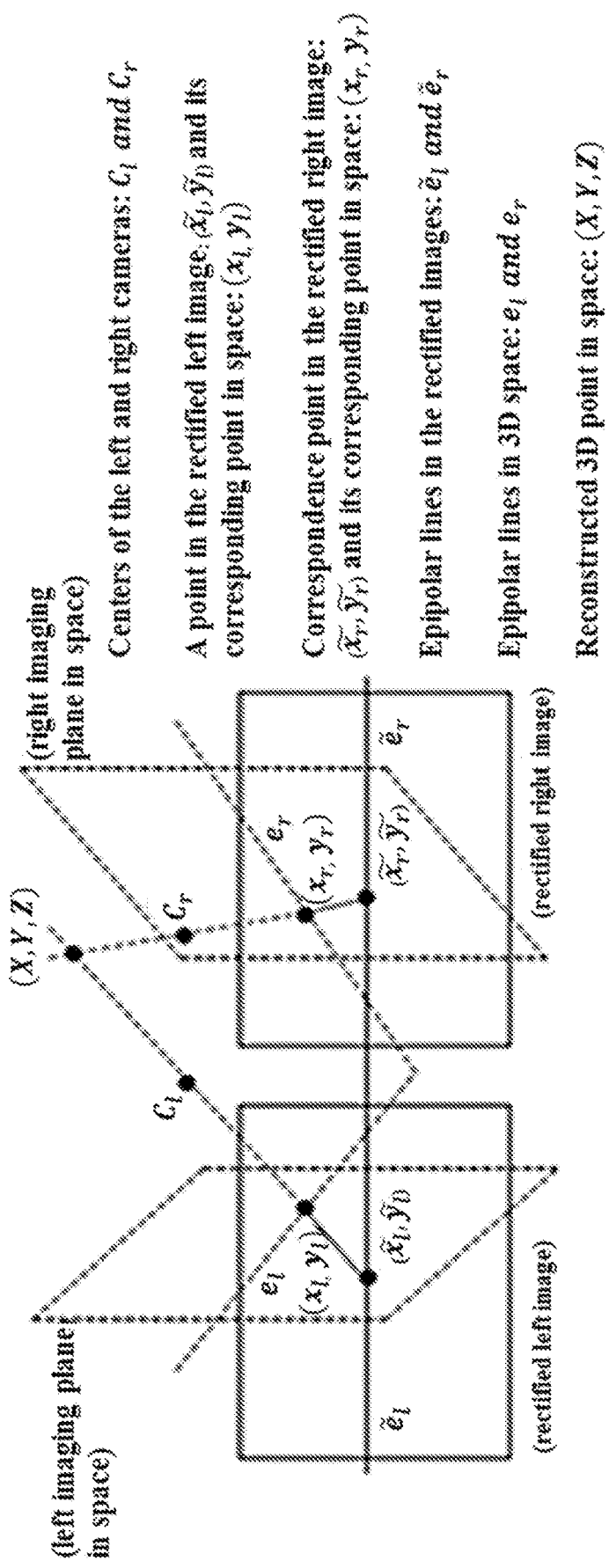
FIG. 10 is an illustration of surface reconstruction.

With reference to FIG. 8, in order to determine image deformation due to the change in $\theta$, the pinhole camera model was employed. For arbitrary material points, q0 and qi initially on the secondary calibration phantom positioned at $\theta$0, their corresponding image pixels, p0 and pi on the imaging plane, are co-linear with the pinhole camera lens. For a given material point, q0, its new pixel location when the target surface was rotated by 0, is given by the pixel location produced by the material point, qi on the original target surface (i.e., $\theta$0), that intersects with the line segment generated by the pinhole lens and q0, as illustrated in FIG. 8. Image deformation due to the change is then produced by subtracting the two pixel locations, pi and p0.

Based on the above description of generating image deformation fields due to the change in m, f, and 0, the following pseudo procedure outlines the sequence of phantom image acquisitions:

Set f=f0, and $\theta$=$\theta$0, successively increase m from m0 and acquire images for each setting of m;
Set m=m0 and $\theta$=$\theta$0, successively increase f from f0 and acquire images for each setting of f;
Set m=m0 and f=f0, successively increase $\theta$ from $\theta$0, and acquire images for each setting of $\theta$; verify that the predicted image deformation field based on pinhole camera model matched with measurement.

Image deformation due to the change in m and f are measured using the phantom images By contrast, image deformation due to the change in θ is computed based on the pinhole camera model, and is verified using the phantom images.

Once appropriate warping parameters, such as a warping deformation field, is determined, the microscope is positioned 460 over tissue 152 instead of the phantom, and stereo images of the tissue are obtained 462 from the cameras 120, 122.

Image Warping to Reference Setting

Next, the stereo images of the tissue are warped 464 by optical warping routine 183 into equivalent images as if they had been taken at the reference settings.

A pseudo algorithm to warp images obtained at an arbitrary image acquisition setting (m,f) and surface orientation relative to the optical axis (O):
Use deformation field due to the change in m to generate image at setting of (m0, f, θ);
Use the resulting image and analytical solution of deformation due to the change in θ, produce image at settings of (m0, f, θ0);
Use the resulting image and deformation field due to the change in f, to produce a warped image at the reference settings, (m0, f0, θ0);

In an alternative embodiment, a single deformation field, or warping parameters, for the entire transformation from the arbitrary setting (m, f, θ) into a warped image corresponding to an image as if it had been taken at the reference setting (m0, f0, θ0) is used in a single warping operation.

Next, the stereo precalibration parameters obtained from precalibration phantoms with the optical system at the reference setting (m0, f0, θ0) are used to reconstruct 466 a surface profile of the tissue in 3D. The reconstructed surface profile may then be used with a computer model of deformation 186 of the tissue and a pre-surgery location of a tumor or lesion as determined in three dimensions from pre-surgery images obtained by conventional medical imaging devices such as CT scanners and MRI machines to locate 468 the tumor 156 as displaced during surgery in a manner similar to that described by Hai Sun. Alternatively, or in addition to displaced tumor locations, the computer model of deformation of the tissue may be used to determine intra-surgery locations of other anatomic features of the tissue so that these features may be preserved.

Finally, image processor 180 uses a display system 190 to display the surface profile and tumor locations, or locations of other anatomic features, so that a surgeon may remove the tumor or lesion while preserving other critical anatomic features of the tissue. In an embodiment, an updated MRI (uMR) image stack is prepared 470 by warping or annotating the preoperative MRI to show the displaced locations of tumor and other structures. The determined displaced locations of tumor and other structures are displayed 472 to the surgeon, who may use this displayed information 474 to locate the tumor or additional tumor material for removal, or to determine whether the tumor has been successfully removed. Similarly, in alternate embodiments fluorescent images, differenced fluorescent images, depth resolved fluorescent images, and quantitative depth resolved fluorescent images may be displayed to the surgeon with and without uMR information. If the tumor has not all been removed, more tumor may be removed and the process repeated 476 beginning with determining warping parameters for a current optical setting 456, in most embodiments by interpolating in table 458, and capturing a new stereo image pair 462 of the tissue.

Library-Based Calibrations

It can be inconvenient to require a surgeon to position a secondary calibration phantom in the field of view of a surgical microscope when the surgeon changes focal length, magnification, or other optical parameters of the system.

Figure 9:
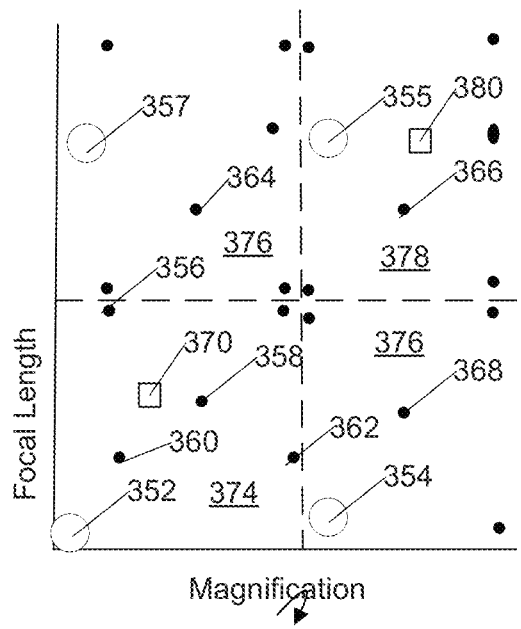
FIG. 9 illustrates points in a table or library of calibrations with primary and secondary calibration points

FIG. 9 illustrates a family of reference settings (including each reference setting S0) or primary calibration points 352, 354, together with secondary calibration points 356, 358, 360, 362, 364, 366, 368, are stored in a warp deformation field parameter (DFP(n)) and 3D reconstruction parameter multidimensional table or library 372 (FIG. 1). An encoder 374 is provided for the microscope zoom and focus controls. Table or library 372 is indexed by the zoom and focus control settings, which correspond to magnification and focal length. For simplicity, only magnification and focal length are illustrated in FIG. 9 in a two-dimensional diagram representative of a two-dimensional table, in an actual system additional optical parameters, such as microscope orientation angles θ, are provided as additional dimensions to the table. Each set of deformation field parameters is a constant representing no deformation for the primary calibration point S0 or points, or is derived by adjusting optical parameters of the system such as the image magnification (m) and focal length (f) parameters to correspond to the predetermined secondary calibration point, positioning the secondary calibration phantom, capturing an image pair is captured at this calibration point, and fitting of deformation parameters such that a warped image pair produced from the image pair closely resembles saved stereo images of the phantom captured at a reference setting S0, such as primary calibration point 352.

In this table-based embodiment, when surface profile extraction is desired at a runtime arbitrary optical setting set, such as setting 370, during surgery by a surgeon, the runtime optical settings are determined by determining the magnification m, and focal length f, using the encoder 374 on the zoom and focus controls. Angles are determined by reading microscope angle information from tracker 142. A deformation field parameter set for the runtime optical setting is then determined by interpolation from nearby entries in the table or library 372.

A runtime image pair of tissue is then captured. The runtime optical warping parameters are then used to warp the runtime image pair to an image pair that corresponds to the specific reference setting S0, 352 that was used for secondary calibration of the nearby entries in the table as heretofore described. 3D reconstruction is then performed using 3D reconstruction parameters determined for that specific reference setting.

The use of a reference setting S0 at the extreme low magnification end of the optical system zoom range, and at a nearest focus length of the optical system focus range, has advantage in that it can be reproducibly set as there is a mechanical stop at these points. Further, when an image is warped to correspond to a lower magnification setting, 3D reconstruction may be more accurately performed than when it warped to a higher magnification where portions of the warped image exceed the boundaries of images used to calibrate the 3D reconstruction parameters.

In an alternative embodiment, in order to provide more accurate 3D reconstruction at higher magnification and longer focal length settings, additional reference image acquisition settings at the midrange of optical system settings are used in addition to the extreme settings at the lowest magnification and shortest focal length. In this embodiment, additional reference settings 354, 355 are provided at a midrange of magnification. Further, in a particular embodiment, additional reference settings 355, 357 are provided at a reproducible, but greater than minimum, set-point of focal length. 3D reconstruction parameters are determined by primary calibration, similarly to the process heretofore described for determination of 3D reconstruction parameters for the reference setting S0, for each of these additional reference settings 354, 355, 357.

It is desirable that each reference setting S0, 352, 354, 355, 357 be a setting that the optical system can be reproducibly be returned to. Certain microscopes are provided with motorized focus and zoom controls, together with encoders 374. These microscopes may be provided with a preset or bookmark memory permitting them to be returned to a predetermined preset of focus and zoom; these microscopes are particularly adaptable for operation with more than one reference setting. Other microscopes may be equipped with a mechanical detent, such as a detent at a midpoint setting of magnification (or zoom). In embodiments using these optical systems, each reference setting S0, 352, 354, 355 is a setting that is bookmarked or at mechanical detents.

In a multiple-reference-setting embodiment, the plane of focal length and magnification, or in an embodiment having a single angle encoded a 3-space, or in an embodiment having two angles encoded a 4-space, is divided into quadrants, such as quadrant 374, 376, 378, cubes, or hypercubes (hereinafter quadrant) respectively.

In a multiple reference setting embodiment, secondary calibration points, such as calibration points 364, 366, and 368, are determined at multiple optical system settings in each quadrant, according to the procedure for secondary calibration described above, where each secondary calibration point provides distortion field parameters DFPs for warping an image taken at the calibration point to the primary calibration point of the quadrant within which the secondary calibration point lies. For example, in the illustration of FIG. 9, top right quadrant secondary calibration points 366 provide DFPs for warping images to correspond to images taken at the top right quadrant primary calibration point or reference setting 355; with bottom left quadrant secondary calibration points 356, 358, 360 provide DFPs for warping images to correspond to images taken at the bottom left quadrant primary calibration point or reference setting 352.

In the multiple-reference-setting embodiment, when a surgeon selects a runtime setting, such as setting 370, 380, the processor 124 uses the encoders 143 to determine the runtime setting. The processor 180 executes a selection routine to determine the quadrant in which the runtime setting occurs by comparing the runtime setting with settings of calibration points in the warp and 3D parameter table or library 372. Typically, the quadrant is chosen to be that having a reference setting, such as reference setting 352, 355 nearest in focal length to that of the runtime setting, and the nearest magnification setting less than the magnification of the runtime setting. A runtime distortion field parameter (DFP(run)) is then determined by interpolation, as heretofore described, between nearby secondary calibration points recorded in library 372.

As previously described, a runtime stereo image is then captured, and warped to correspond to images captured at the primary calibration point or reference setting, of that quadrant, such as setting 352 for the lower left quadrant 374 or setting 355 for runtime settings in the top right quadrant 378. 3D extraction is then performed on the warped image, using 3D extraction parameters recorded in library 372 and associated with the primary calibration point or reference setting 352, 355, associated with that quadrant.

Determining 3D Deformation Field

In an alternative embodiment, instead of determining specific correspondence points, determining 3D coordinates of those 3D correspondence points, and deriving a 3D surface map from a cloud of such points, a 3D image warping deformation field is determined that maps a first image, such as a left image, of each stereo pair into an image that corresponds to the second image, such as a right image, of the stereo pair. A 3-D surface map is then determined from that 3D image warping deformation field.

Image Reconstruction From Warping Field

Stereovision reconstruction can be expressed by the following equation to determine the 3D spatial coordinate, P, for a given sampling point in the rectified left image, p:

$$P=G(p,F(p))=G(p,p+u(p)), \quad (1A)$$

where F(p) is a functional form describing the image coordinate of the correspondence point of p in the rectified right image, and is obtained when the horizontal disparity, u(p), is available, and G is the geometrical operation (including transformation and triangulation) established from calibration. Therefore, reconstructing the 3D surface in space is reduced to establishing a disparity map between the two rectified images for a given set of calibration parameters. The quality (accuracy and density) and the computational efficiency of the disparity map determine overall performance in stereovision reconstruction. For purposes of this discussion, we refer to an unwarped left image and warp that image to correspond to a right image; however it is anticipated that left and right may be reversed in alternative embodiments. Establishing the disparity map between the rectified left ("undeformed") and right ("deformed") image pair is analogous to determining the motion field between the two images.

Determining a Vertically-Unconstrained 3D Warping Deformation Field

It is known that a particular point P(x,y,z) on a surface should appear along the same horizontal epipolar line $\underline{e}$ in each image of a stereo pair, although its location along that line will differ with the angle between the images and 3D height. In an embodiment, a 3D warping deformation field (3D-DFP) is determined by imposing a vertical, or epipolar, constraint while fitting deformation field parameters to the images. In a novel unconstrained embodiment, no such vertical constraint is imposed.

In the unconstrained embodiment, using a variational model and assuming the image intensity of a material point, (x,y), or its corresponding pixel does not change, a gray value constancy constraint $$I(p+w)=I(p), \quad (2)$$

is assumed in which p=(x,y) and the underlying flow field, w(p), is given by w(p)=(u(p), v(p)), where u(p) and v(p) are the horizontal and vertical components of the flow field, respectively. Global deviations from the gray value constancy assumption are measured by an energy term $$E_{Data}(u,v)=\int \psi(|I(p+w)-I(p)|^2)dp, \quad (3)$$

where a robust function, $\psi(x)=\sqrt{x^2+\varepsilon^2}$, was used to enable an $L^1$ minimization in a particular study ($\varepsilon$=0.001).

The gray value constancy constraint only applies locally and does not consider any interaction between neighboring pixels. Because the flow field in a natural scene is typically smooth, an additional piecewise smoothness constraint can be applied to the spatial domain, leading to the energy term $$E_{Smooth}(u,v) = \int \phi(|\nabla u|^2 + |\nabla v|^2) dp \quad (4)$$

where $\phi$ is a robust function chosen to be identical to $\psi$, and $\nabla$ is the gradient operator where $$|\nabla(u)|^2 = u_x^2 + u_y^2 \left( u_x = \frac{\partial u}{\partial x}, u_y = \frac{\partial u}{\partial y} \right),$$

which is analogous for v.

Combining the gray value constancy and piecewise smoothness constraints leads to an objective function in the continuous spatial domain given by $$E(u,v) = E_{Data} + \alpha E_{Smooth}, \quad (5)$$

where $\alpha$ ($\alpha > 0$; empirically chosen as 0.02 in a particular feasibility study) is a regularization parameter. Computing the optical flow is then transformed into an optimization problem to determine the spatially continuous flow field (defined by u and v) that minimizes the total energy, E. In this study, an iterative reweighted least squares algorithm, and a multi-scale approach starting with a coarse, smoothed image set were used to ensure global minimization.

Disparity Estimation Based on Optical Flow

In a particular flow-based stereo surface reconstruction study performed on intraoperative stereo pairs taken during surgical procedures, the rectified images were down-sampled to expedite processing, with sufficient resolution retained to provide adequate 3D modeling. The full-field horizontal displacements from two-frame optical flow on the two (down-sampled) rectified images served as the disparity map, u(p), from which texture-encoded 3D stereo surface is readily reconstructed from the geometrical operations defined above. Although the flow field is spatially smooth due to the smoothness constraint applied to the optimization, spurious disparities can still occur in regions of insufficient features and/or with occluded pixels, similarly to SSD-based correspondence matching. Instead of correcting for these spurious disparities in the solution field by applying appropriate constraints in optimization with additional burden in algorithmic implementation and increase in computational cost, we detect regions of spurious disparities using values of the vertical flow field, v(p). This strategy was possible because ground-truth values of zeroes for v(p) were known a priori as a direct result of the epipolar constraint where correspondence point pairs were pre-aligned on the same horizontal lines in rectified images.

Therefore, pixels with large absolute values of vertical discrepancy v(p) (such as pixels displaced above or below a certain threshold) that violate the epipolar constraint also indicate likely spurious horizontal disparities in the flow field, u(p). In some embodiments these pixels are simply excluded from stereo surface reconstruction. In an alternative embodiment, the sampling pixels are empirically filtered into regions of high, mid, or low confidence levels based on the absolute vertical disparities, abs(v), when they were either less than a first threshold, between the first threshold and a second threshold, or above the second threshold in pixels, respectively, where these particular threshold values were empirically chosen. Horizontal disparity values for pixels with a high or low confidence level were either retained or removed, while those in-between were interpolated based on those of a high confidence level. Such a two-tier threshold interpolation/exclusion scheme was effective in maximizing regions of sufficient disparity accuracies while excluding from surface reconstruction those with insufficient features such as those due to specular artifacts or occluded pixels.

An experimental embodiment using 3D reconstruction based upon optical flow using a vertically unconstrained image deformation fitting process and using vertical disparity for disparity detection provided superior surface reconstruction, and may permit more accurate determination of intraoperative tumor locations.

Interpolation, Warp to Reference, Warp to 3D, Model Movement

Figure 11:
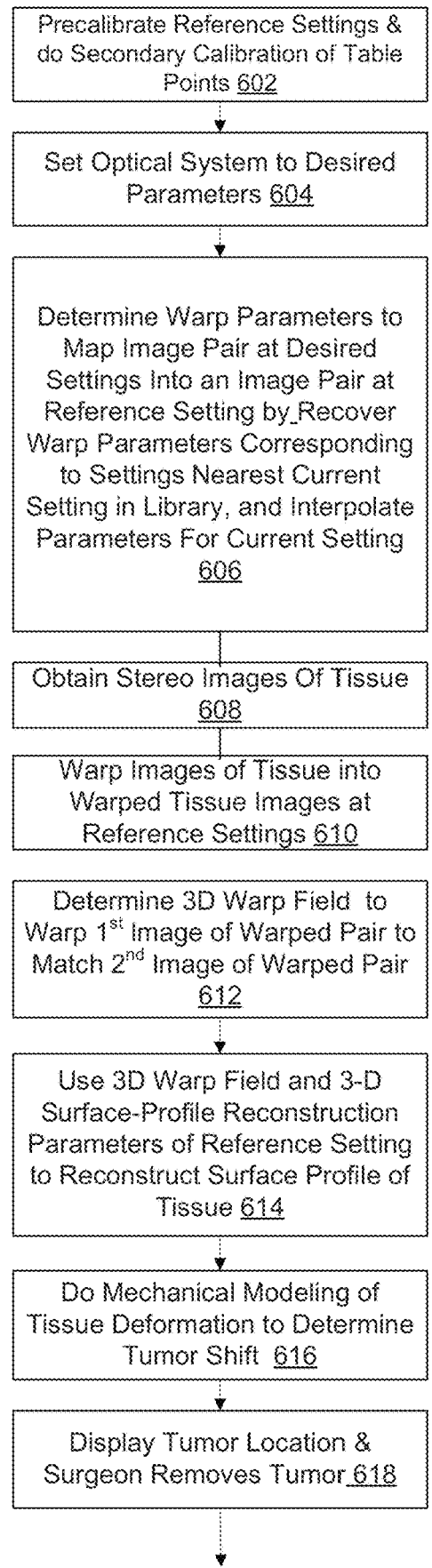
FIG. 11 is a flowchart illustrating modeling tumor shift using a combination of methods herein described.

Putting together the heretofore described procedures, as illustrated in FIG. 11, a calibration library or table 372 is prepared 602 by doing primary calibration using the 3D calibration phantoms at one or more reference settings, and 3D reconstruction parameters are stored for each setting. Secondary calibration points are then added into the table 372 by imaging a secondary calibration phantom at each reference setting, setting the optical system to correspond to each secondary calibration point, re-imaging the secondary calibration phantom, and determining warp field parameters that map the re-image of the secondary calibration phantom to match the image taken at a reference setting appropriate for use with that secondary calibration point; these warp field parameters are stored in the table.

The optical system is then set to a desired setting 604, and warp field parameters suitable for mapping images taken at the desired setting into warped images corresponding to images taken at a reference setting are determined 606 by reading warp parameters for secondary calibration points near the desired setting and interpolating to give interpolated warp parameters. A stereo image pair is obtained 608 from the cameras and the interpolated warp parameters are used to warp 610 that image pair to a warped image pair that corresponds to an image pair taken at the reference setting used for calibrating those secondary calibration points.

A vertically-unconstrained warp-field fitting operation is then performed to determine 612 3D warp field parameters for warping a first image of the warped stereo image into a second image of the warped stereo image pair, and, where vertical deformation in the warp field exceeds a first limit, the warp field is adjusted, and where vertical deformation exceeds a second limit, associated image pixels are excluded from consideration in the warp-field fitting operation in a further iteration of fitting the 3D warp field parameters to the warped image pair.

The fitted 3D warp field parameters are used to reconstruct 614 a surface profile of the tissue. This surface profile is in turn used to constrain a mechanical model of the tissue, the model is used to determine shift of structures in the tissue, such as a shift of a tumor 616, and an intraoperative location of those structures and the tumor. The intraoperative structure locations and tumor location is then displayed 618 such that a surgeon can remove the tumor.

The heretofore described procedure may be used to determine intraoperative positions of a lesion or other structures in tissue of the mammalian, including human brain or may be adapted to determining intraoperative positions in other soft-tissue organs.

Operation in Hyperspectral Reflectance Imaging Mode

The system herein described may be operated to produce hyperspectral reflectance images as follows.

In embodiments having LED-based or incandescent white light illuminators 166, the illuminators are turned on. In embodiments having illuminators as described with reference to FIG. 1E, laser 236 is turned on, and processor 180 puts a blank white display on DMD 238. In embodiments having a multiple-filter array hyperspectral camera 128 as discussed with reference to FIG. 1B, a hyperspectral reflectance image stack is then captured directly. Each pixel of each wavelength image of the stack corresponds to light imaged by a photosensor of the array imager covered by a filter having bandpass at that wavelength, such that for every image stack a number of images are collected with each image corresponding to a wavelength in the range of the electromagnetic spectrum of interest. In this way a full spectrum can be reconstructed at each pixel in of the 3d image stack. In embodiments having a single-filter, single-broad-band-camera 132 hyperspectral camera as discussed with reference to FIG. 1, or a dual-imager hyperspectral camera as discussed with reference to FIG. 1A, filters 130, 135, 139 are set to each wavelength for which reflectance imaging is desired. Then, using the image sensor 130, 138, 137 appropriate for each determined wavelength, an image of the hyperspectral reflectance image stack is captured at those wavelengths. In embodiments having a multiple-filter array imager, reflectance images are captured at one or more wavelengths corresponding to illumination wavelengths; if white light is used for illumination, a full hyperspectral image stack is captured in a single, snapshot, operation. In an embodiment, separate images of the hyperspectral image stack are captured at each of several wavelengths of interest, including wavelengths corresponding to peak absorption wavelengths of oxyhemoglobin, and deoxyhemoglobin; these images may be displayed to a user by processor 180 on monitor 192. A ratio image is also determined by ratioing intensity of corresponding pixels of the oxyhemoglobin and deoxyhemoglobin images to produce an image of hemoglobin saturation, and an image of a total of hemoglobin concentration may also be generated. Similar images at wavelengths suitable for use with other chromophores may also be used. Images may also be generated based on the scattering properties of the tissues derived from the hyperspectral reflectance images.

The hyperspectral reflectance imaging, and spatially modulated (SM) hyperspectral reflectance imaging, are therefore performed in image processing routines executing on processor 180 that retrieve the optical properties separately for each emissions wavelength based on a look-up table derived from Monte Carlo simulations of the radiation transport or a diffusion theory approximation either modeled with numerical methods or estimated from analytical forms derived under plane wave assumptions. The recovered optical properties at multiple wavelengths then allows recovery of such medically useful markers as tissue oxygenation and other endogenous properties of the tissue

Operation in Fluorescent Imaging Mode

The system herein described may be operated to produce fluorescent images as follows.

Fluorescent stimulus light source 168 is set to a preferred stimulus wavelength of a first fluorophore that is expected to be present in tissue 152. In embodiments having a multiple-filter array hyperspectral camera 128 as discussed with reference to FIG. 1B, a fluorescence image is then captured directly using photosensors of each tiling pattern having filters with bandpass at an expected fluorescence emission wavelength of the fluorophore. In embodiments having a single-filter, single-broad-band-camera 132 hyperspectral camera as discussed with reference to FIG. 1, or a dual-imager hyperspectral camera as discussed with reference to FIG. 1A, filters 130, 135, 139 are set to a first fluorescent emissions wavelength appropriate to the fluorophore. Then, using the image sensor 130, 138, 137, an image of fluorescent emitted light is captured at that wavelength. These images may be displayed to a user by processor 180 on monitor 192. Additional fluorescent images may be captured at a second, third, or fourth emissions wavelength appropriate to the fluorophore or fluorophores, further studies, and preferences of the surgeon.

In some embodiments, including many embodiments making use of multiple fluorophores, fluorescent stimulus light source 168 is set to a second stimulus wavelength of fluorophore that is expected to be present in tissue 152, in some embodiments this fluorophore is the first fluorophore, and in other embodiments it is a second fluorophore. A second fluorescence image, or set of fluorescence images, is then captured directly at one or more expected fluorescence emission wavelengths of the fluorophore. These images may also be displayed to a user by processor 180 on monitor 192. In alternative embodiments, more than two stimulus wavelengths, and/or more than two fluorescent emissions wavelengths, may be used for fluorescence imaging.

The wavelength selected for stimulus light and for the wavelength for capturing fluorescent emissions depends on the expected fluorophore, for example protoporphyrin IX has an absorption peak at 405 nanometers that may be used for stimulus light, and emissions wavelengths of 635 nanometers with a shoulder of 710-720 nanometers that may be used for fluorescent image capture. Similarly, fluorescein may be stimulated with stimulus light near 500 nanometers while emitting near 530 nanometers, a wavelength suitable for fluorescent emissions image capture. Also, Indocyanine Green (ICG) may be stimulated with light between 680-700 nanometers while emitting near 780 nanometers, a wavelength that may be used for fluorescent emissions image capture. The system is adaptable for use with other fluorophores by selecting appropriate stimulus and imaging wavelengths. Further, memory 178 has deconvolution or unmixing routines that, when executed, determine contributions to fluorescent hyperspectral captured image stacks from two, or in some embodiments more than two, separate fluorophores having different emissions wavelengths by processing a hyperspectral fluorescent emissions stack. A hyperspectral image stack essentially provides a spectrum of emissions as received by each pixel. Our work has shown deconvolving contributions from two, or in some cases more than two, fluorophores is often possible using a single emission spectra captured under a single stimulus wavelength of light and base spectra of each fluorophore present and tissue base autofluorescence. The present embodiment permits capturing separate hyperspectral image stacks under each of several stimulus light wavelengths, and this additional information is believed useful in simplifying deconvolution of contributions from some fluorophores and in extending the number of fluorophores that may be simultaneously quantified in Fluorescent Imaging Mode (FI), quantified Fluorescent Imaging Mode (qFI), Depth-Resolved Fluorescent Imaging Mode (dFI), and Quantified Depth-Resolved Fluorescent Imaging Mode (qdFI). Execution of the deconvolution or unmixing routines therefore generates independent fluorophore concentration maps for each fluorophore.

Operation in Spatial-Frequency-Modulated Reflectance Mode

Embodiments of the system having illuminators as described with reference to FIG. 1E may also be operated in a spatial-frequency-modulated reflectance-imaging mode to determine optical properties, including absorption & scattering properties, at each pixel of images of tissue 152; or, in an alternative embodiment for improved quantification and depth resolution, at each voxel of a three-dimensional model of tissue 152. In, this mode, laser 236 (or other broadband lamp) is turned on, and processor 180 puts a sequence of white display on DMD 238. In embodiments having a multiple-filter array hyperspectral camera 128 as discussed with reference to FIG. 1B, a hyperspectral reflectance image stack is then captured directly, with each pixel of each wavelength image of the stack corresponding to light imaged by a photosensor of the array imager covered by a filter having passband at that wavelength. In embodiments having a single-filter, single-broad-band-camera 132 hyperspectral camera as discussed with reference to FIG. 1, or a dual-imager hyperspectral camera as discussed with reference to FIG. 1A, filters 130, 135, 139 are set to each wavelength for which reflectance imaging is desired. Then, using the image sensor 130, 138, 137 appropriate for each determined wavelength, an image of the hyperspectral reflectance image stack is captured at that wavelength. In an embodiment, separate images of the hyperspectral image stack are captured at wavelengths including peak absorption wavelengths of oxyhemoglobin, and deoxyhemoglobin; these images may be displayed to a user by processor 180 on monitor 192. A ratio image is also determined by ratioing intensity of corresponding pixels of the oxyhemoglobin and deoxyhemoglobin images to produce an image of hemoglobin saturation. Similar images at wavelengths suitable for use with other chromophores may also be used.

The spatially modulated mode is also used at fluorescent stimulus wavelengths and fluorescent emissions wavelengths to determine reflectance, absorbance, and scattering parameters for use in modes described below, including qFI, dFI, and qdFI modes.

In an embodiment, spatially modulated mode is also used to recover the tissue surface profile in real-time using phase shifting profilometry (2). This involves retrieving the phase shift for every point in the reference plane, between a projected spatially modulated light pattern and a camera acquired image of the light pattern deformed by the surface. The phase shift is then used to calculate absolute height for all points on the surface in the reference plane. The first step is to generate the light patterns. We require 3 different patterns, each with a different phase. The reference patterns are given by:

$$s_1(x) = a_0 + \alpha_1 \cdot \cos[2\pi\, f_0 x] \quad \text{(Eq. 2)}$$

$$s_2(x) = a_0 + \alpha_1 \cdot \cos\left[2\pi\, f_0 x + \frac{2\pi}{3}\right]$$

$$s_3(x) = a_0 + \alpha_1 \cdot \cos\left[2\pi\, f_0 x + \frac{4\pi}{3}\right]$$

Here f0 is the spatial frequency of the modulation, a0 is the offset, and a1 is the amplitude intensity. Since we illuminate with projected 8-bit grayscale images, we use a0=a1=225/2. We acquire one deformed light pattern for each projected pattern, yielding 3 deformed light patterns:

$$d_1(x, y) = a_0 + \alpha_1 \cdot \cos[2\pi\, f_0 x + \phi(x, y)] \quad \text{(Eq. 3)}$$

$$d_2(x, y) = a_0 + \alpha_1 \cdot \cos\left[2\pi\, f_0 x + \frac{2\pi}{3} + \phi(x, y)\right]$$

$$d_3(x, y) = a_0 + \alpha_1 \cdot \cos\left[2\pi\, f_0 x + \frac{4\pi}{3} + \phi(x, y)\right]$$

Here $\phi(x,y)$ is the phase shift for all points (x,y) in the reference plane. Two intermediary variables are then calculated from the 6 light patterns:

$$\overline{S} = \frac{-\sqrt{8} \cdot (s_2 - s_3)}{(2s_1 - s_2 - s_3)} \quad \overline{D} = \frac{-\sqrt{8} \cdot (d_2 - d_3)}{(2d_1 - d_2 - d_3)} \quad \text{(Eq. 4)}$$

The phase shift is then given by:

$$\phi(x,y) = \text{unqwrap}(\text{artan}(\overline{D}(x,y))) - \text{unqwrap}(\text{artan}(\overline{S}(x,y))) \quad \text{(Eq. 5)}$$

When unqwrap is a 2D phase unwrapper needed to correct the $2\pi$ shifts caused by the arctan discontinuity. Finally, the absolute height at each point is calculated by:

$$h(x, y) = \frac{l_0 \phi(x, y)}{\phi(x, y) - 2\pi\, f_0 d_0} \quad \text{(Eq. 6)}$$

Operation in Wide Field Quantitative Fluorescent-Imaging (qFI) Mode

Figure 12:
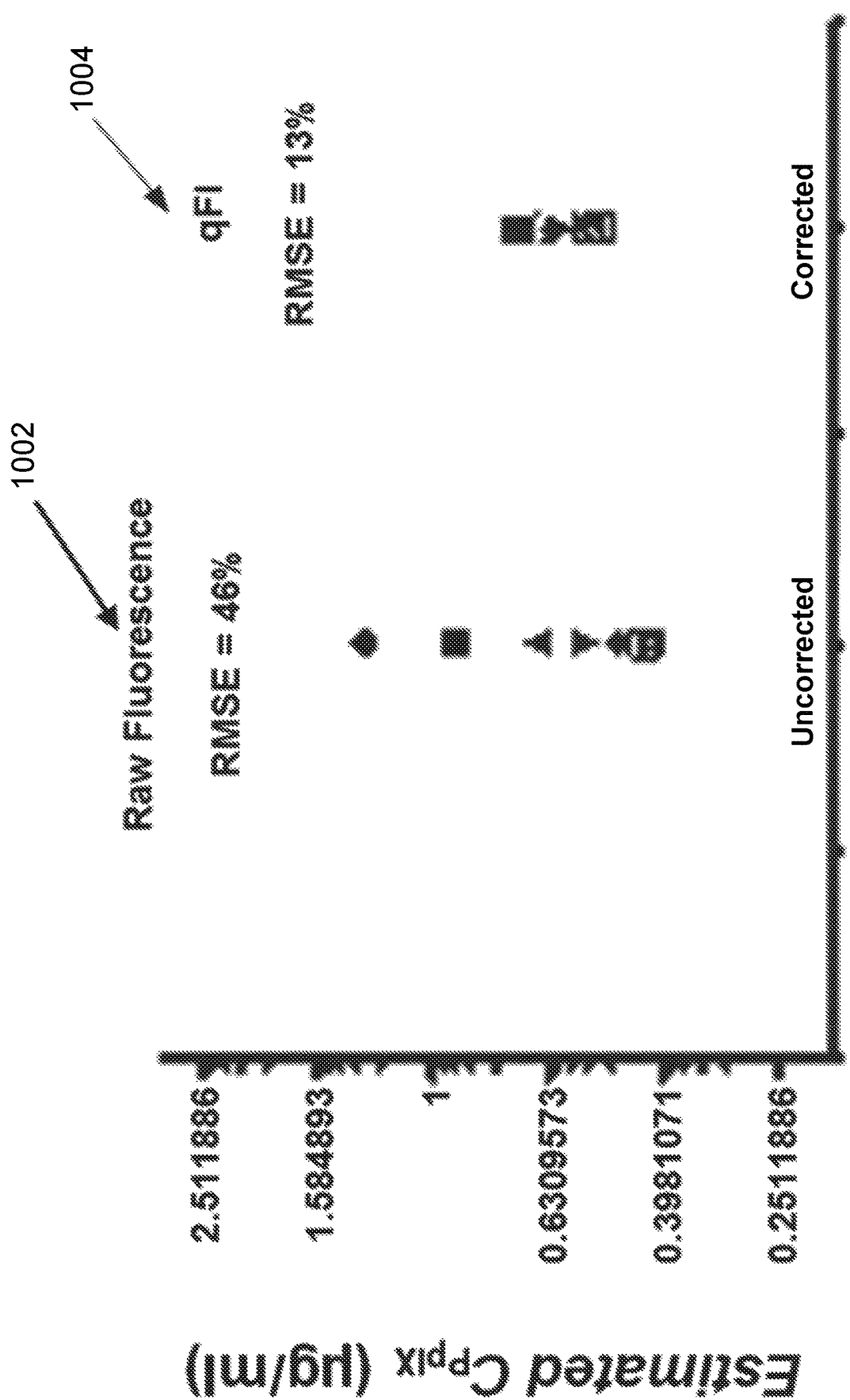
FIG. 12 is an illustration of uncorrected versus corrected estimates of fluorophore quantity.
Figure 13:
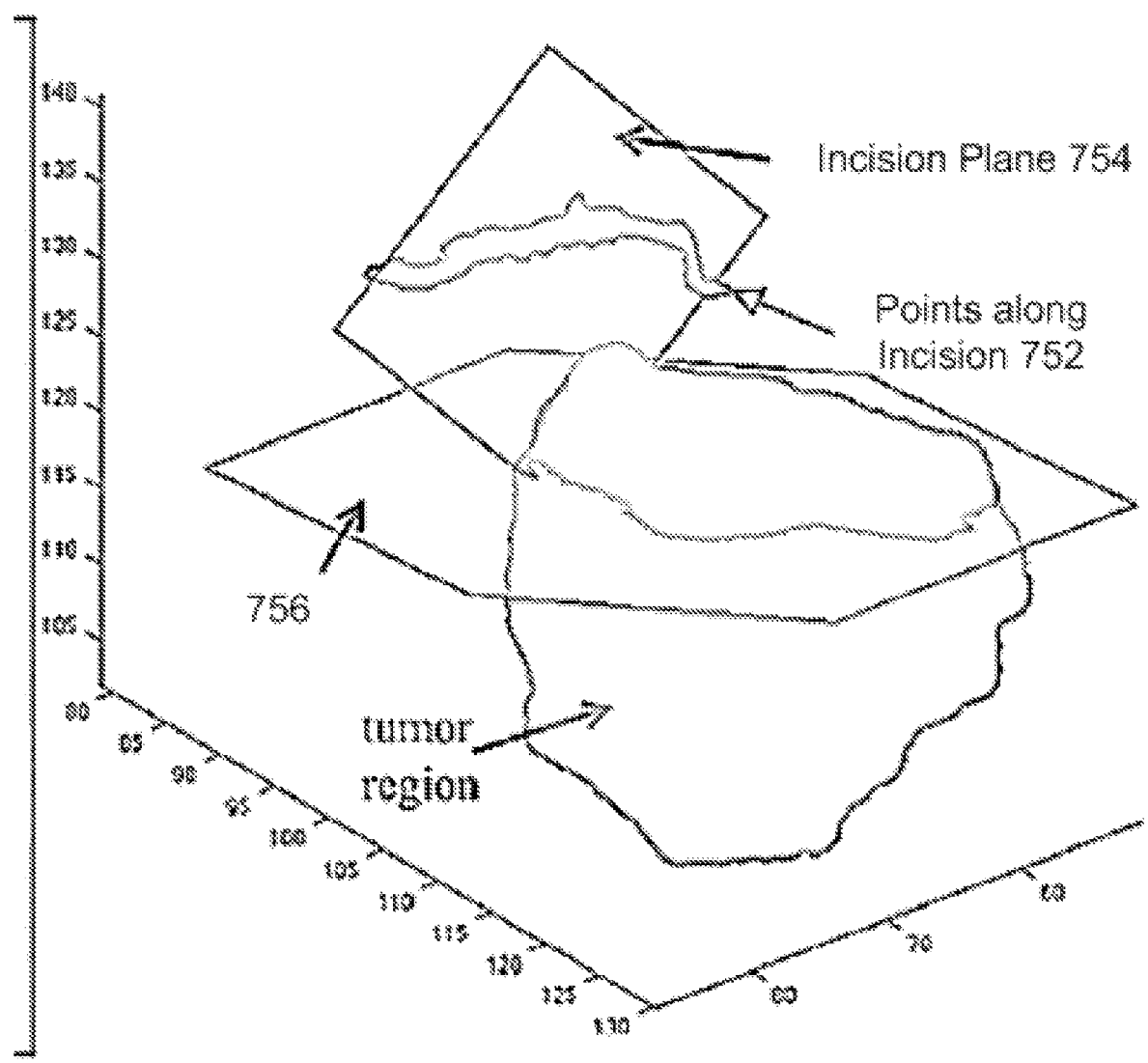
FIG. 13 is an illustration of finding an incision plane and incision depth or focal plane.

FIG. 12 illustrates readings of fluorophore intensity as observed in Fluorescent Imaging Mode of fluorophores at a constant concentration in phantoms having a variety of optical properties in left column 1002.

Figure 20A:
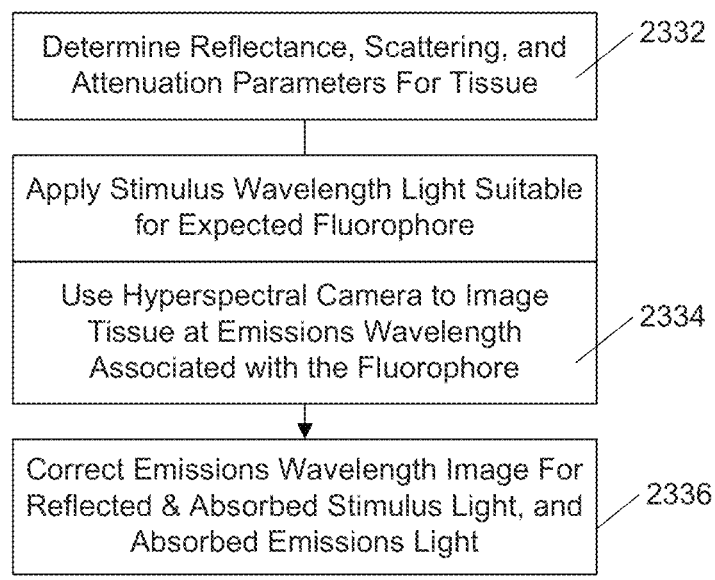
FIG. 20A is a flowchart illustrating operations of correction algorithms based on light transport models and/or data normalization schemes.
Figure 22:
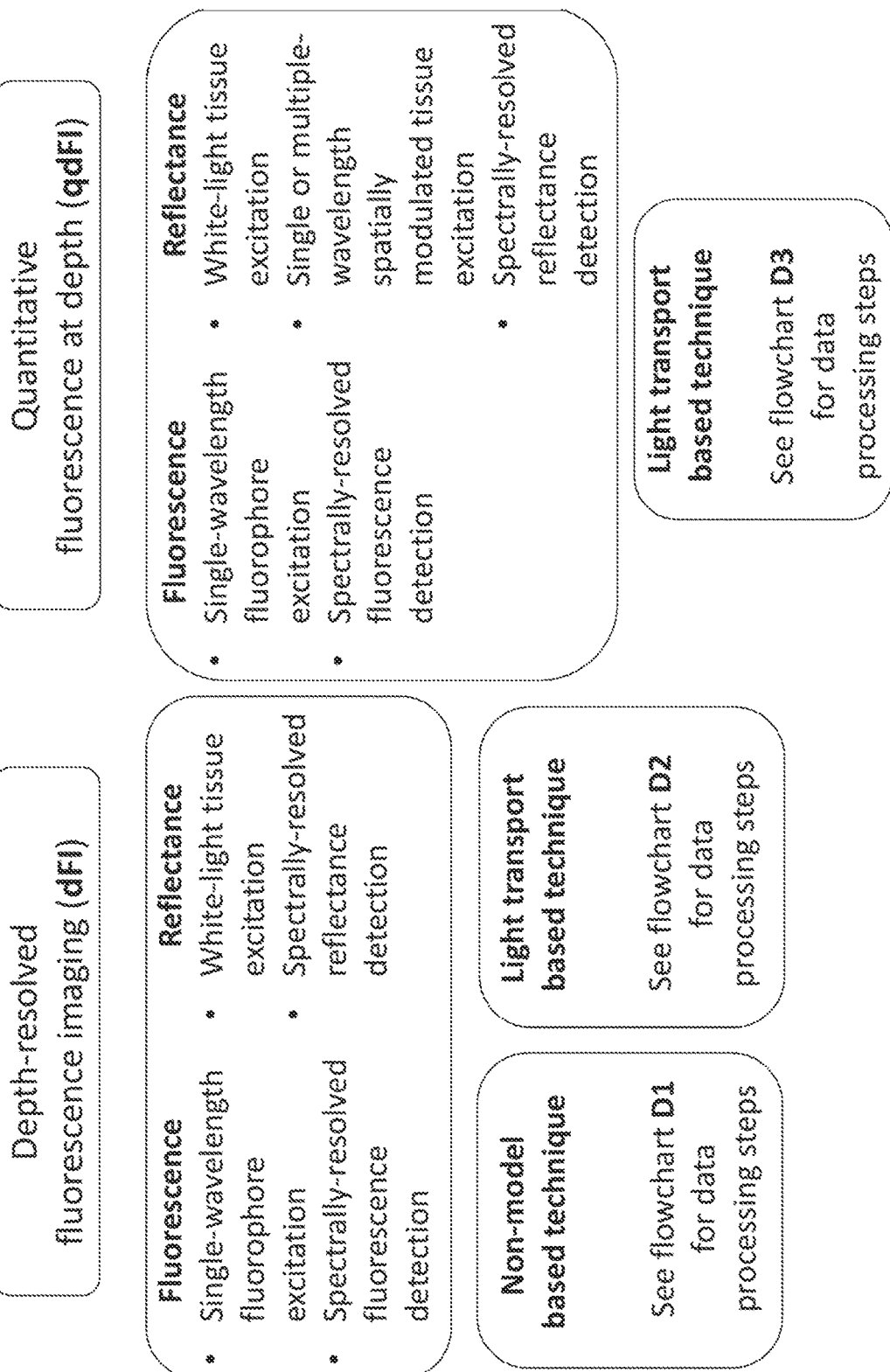
FIG. 22 is an introduction to data flow diagrams for quantitative fluorescence at depth and alternative embodiments of depth-resolved fluorescence imaging, in variations favoring fluorophores emitting in the infrared spectral range.

We apply spectral (based on spectrally-resolved detection) and/or spatial (based on spatially modulated illumination) constraints to the raw fluorescence data in order to obtain the required quantitative information by accounting for the effects of light scattering and absorption on the fluorescence images through correction algorithms based on light transport models and/or data normalization schemes. These corrections operate according to the flowchart of FIG. 20A, and begin by determining 2332 absorbance and reflectance parameters at fluorescence stimulus and emissions wavelengths for each pixel, or for each of many small multipixel regions, of the images. Fluorescence stimulus wavelength light is applied and fluorescence emission images are then acquired 2334. These parameters are then used to correct 2336 fluorescence images for stimulus light reflected or absorbed before reaching fluorophore, and for fluorescent emissions light absorbed after emission and before being released from the tissue. We briefly outline three technical alternatives to realizing wide-field qFI, each of which may be used in one or another embodiment:

(a) Technical Realization of Wide-Field qFI:

We use a wide-field qFI method which achieves a minimum sensitivity to CPpIX of 50 ng/ml with an error of no more than 20% over a field-of-view (FOV) of at least 4 cm2 in an acquisition time of less than 5 seconds. Wide-field qFI is technically challenging because corrections for light attenuation must consider contributions from surrounding tissues at every point in the FOV. In addition, tissue curvature and ambient lighting can compromise quantitative imaging, and degradation from these effects must be minimized Hence, we developed three approaches to find the optimal method which meets our specifications where each presents tradeoffs in performance fidelity vs. implementation complexity. The first two are direct extensions of our point-probe technique, in which attenuation correction is achieved through measurement of the tissue's diffuse reflectance ('spectrally-constrained'), and the two methods differ in whether the full spectrum or dual wavelength approximations are used. The third method ('spatial light modulation') illuminates the surgical surface with specific and varying spatial patterns of light which allow separation of the absorption and scattering contributions in tissue as described in the section "Operation in Spatial Frequency Modulated Reflectance Mode" above, and these absorption and scattering parameters are then used to correct the wide-field fluorescence image. Estimates of surface fluorophore concentrations, as corrected with the tissue optical properties, are illustrated in right column 1004 of FIG. 12.

(1) Spectrally-Constrained qFI with Full Reflectance Spectrum:

We used a full spectrum weighted basis solution to estimate tissue optical properties that is likely to be effective in single organ systems such as the brain where tissue optical properties are relatively homogeneous. Here, ground truth data (i.e., basis function responses) relating the measured wavelength-dependent diffuse reflectance ($Rd(\lambda)$) to the corresponding absorption ($\mu a(\lambda)$) and (reduced) scattering ($\mu s'(\lambda)$) coefficients were generated using tissue-simulating liquid phantoms with a large range of known optical properties consistent with brain tissue. A 4D set of basis functions, [$Rd, \lambda, \mu a, \mu s'$], were created from this information, and wide-field spectrally-resolved reflectance images acquired during surgery will be decomposed into Rd, and a regularized minimization (e.g., Generalized Least Squares, GLS) was used to determine the best fit of Rd values as a weighted sum of basis function responses to estimate $\mu a(\lambda)$ and $\mu s'(\lambda)$ at every image pixel. A correction image derived from estimates of $\mu a(\lambda)$ and $\mu s'(\lambda)$ will be calculated using light transport models 80 and applied to the raw fluorescence image to produce a quantitative spectrally-resolved fluorescence image. In one embodiment, GLS is applied to each (x,y) corrected fluorescence spectra to unmix the contributions from PpIX and auto-fluorescence, and construct a full FOV image of PpIX. To evaluate the technical feasibility of the approach, we generated preliminary data shown in FIG. 12 which corrects the raw fluorescence using spectral constraints to calculate optical properties that significantly decrease the spectral distortions.

Spectrally-Constrained qFI with Dual Wavelength Ratiometry:

As an alternative, we will investigate an approximate method that uses measurements of tissue reflectance at 2 select wavelengths to correct for tissue attenuation. To demonstrate technical feasibility and clinical potential, initial evaluations of this technique have occurred in tissue-simulating phantoms, ex vivo brain tumor tissue from the CNS-1 rat glioma model, and in vivo during human glioma surgery, using the fluorescence/reflectance point-probe as a gold standard The dual-wavelength approximation yielded a linear relationship between the corrected raw fluorescence and the true PpIX concentration (R-squared=0.6387 for raw vs. R-squared=0.9942 for corrected fluorescence). As a first step towards clinical evaluation, we constructed a prototype spectrally-resolved imaging system and attached it to the surgical microscope. The system collects images of the surgical field continuously across the full visible spectrum ($\lambda$=400-720 nm) and generates data in near-real time of both reflectance (under white light), $Rd(x, y, \lambda)$, and fluorescence (under violet-blue light), $F(x, y, \lambda)$. A two wavelength normalization algorithm was applied to the complete data set to derive a quantitative image of absolute PpIX concentration.

Spatially-Constrained qFI with Spatial Light Modulation:

The image processor 180 executing routines in memory 178 that perform method will estimate tissue absorption and scattering maps using spatial light modulation to correct the raw fluorescence images with the same light transport model as the full-spectrum approach. Here, the detected light pattern is affected by tissue scattering more at high modulation frequency; hence, scattering and absorption properties can be separated by scanning the frequency and relative phase of the illumination patterns. In preliminary studies of technical feasibility, a liquid-crystal-on-silicon device projected sinusoidal patterns of light intensity of varying phase onto the surface and reflected light patterns were captured with a CCD camera in tissue-simulating phantoms and in a rodent glioma model which showed that quantitative maps of tissue optical properties can be recovered with the technique.

Modeling for qFI

Some of the alternative approaches for qFI require light transport modeling in a wide-field geometry. We include factors such as curvature, variable light penetration, and excitation based on spatially modulated light. Specifically, we will merge an existing finite-element diffusion model with an existing Monte Carlo simulation algorithm—Monte Carlo is applied at small depths where diffusion theory can break down, while finite-elements will be used at greater depths where the diffusion model is accurate but Monte Carlo becomes computationally intractable (transition depth depends on wavelength since tissue absorption varies dramatically from violet-blue to red light). The fluorescence light transport model has the optical property maps and a 3D profile of the surgical surface as inputs (curvature is obtained from either a stereovision system we use routinely in the operating room or a 3D profiler based on reflection of a spatially modulated light pattern from the tissue surface). These data represent the actual geometry and relevant attenuation properties of tissue and allow the model to generate simulated fluorescence signals (i.e. basis solutions) from which the actual pixel-by-pixel PpIX concentrations are retrieved from a least-squares match of the measured response to the simulated basis solutions.

Operation in Fluorescent Depth-Resolved Imaging Mode (dFI)

Figure 15:
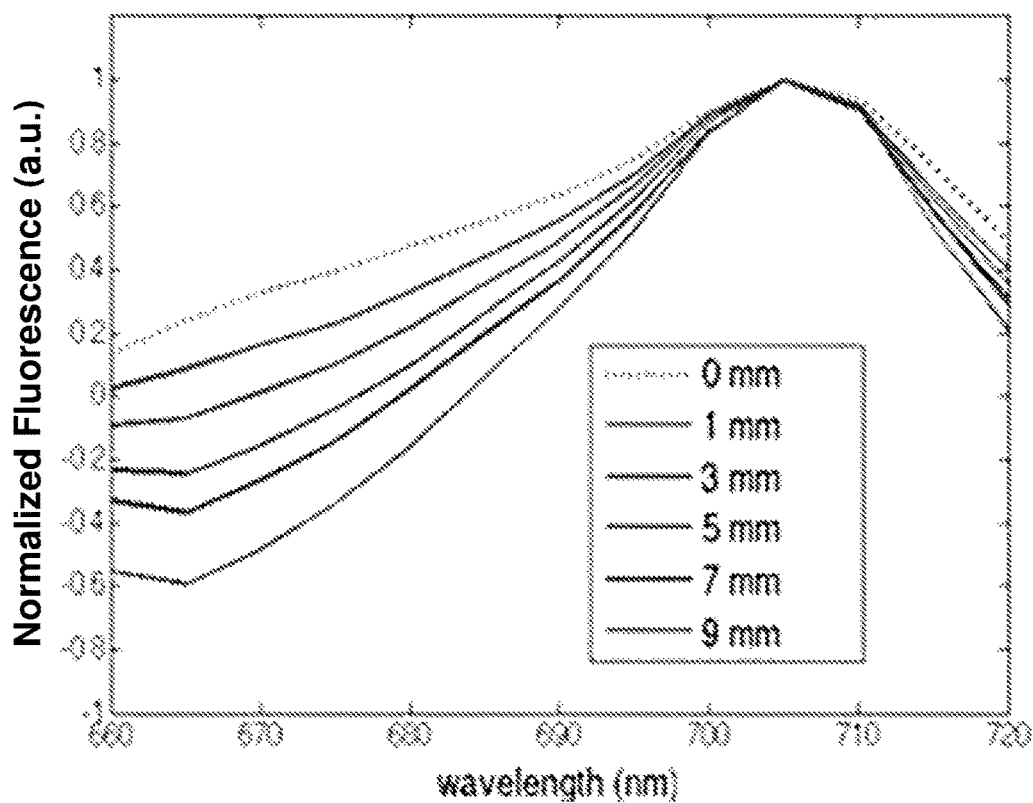
FIG. 15 illustrates differences in observed spectra of light emitted by PPIX as observed above tissue with differences in depth in tissue.
Figure 16:
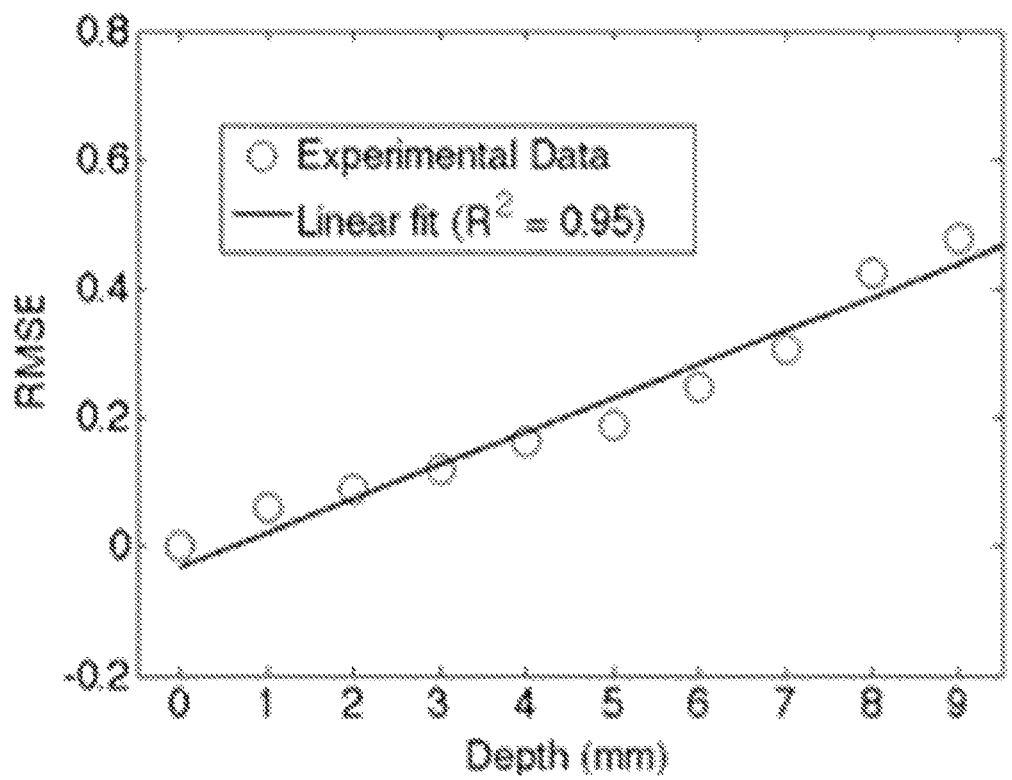
FIG. 16 illustrates fitting a ratio of intensity at two wavelengths from FIG. 15 to an equation relating spectra to depth.

Data-flow diagram D1 and D2, as illustrated in FIGS. 23-24, may prove helpful in understanding dFI mode for fluorophores, including infrared fluorophores, and diagrams D4 and D5, as illustrated in FIGS. 20-21 may prove helpful in understanding dFI mode for visible fluorophores. Also helpful are FIG. 15 and FIG. 16. FIG. 15 illustrates spectra of PpIX as emitted from tissue when the PpIX is located at different depths in tissue, and FIG. 16 illustrates a ratio of intensity of light at two wavelengths emitted by PpIX and detected above tissue at different depths as curve fit to an equation. Many other fluorophores exhibit similar spectral shifts with depth in tissue.

Figure 23A:
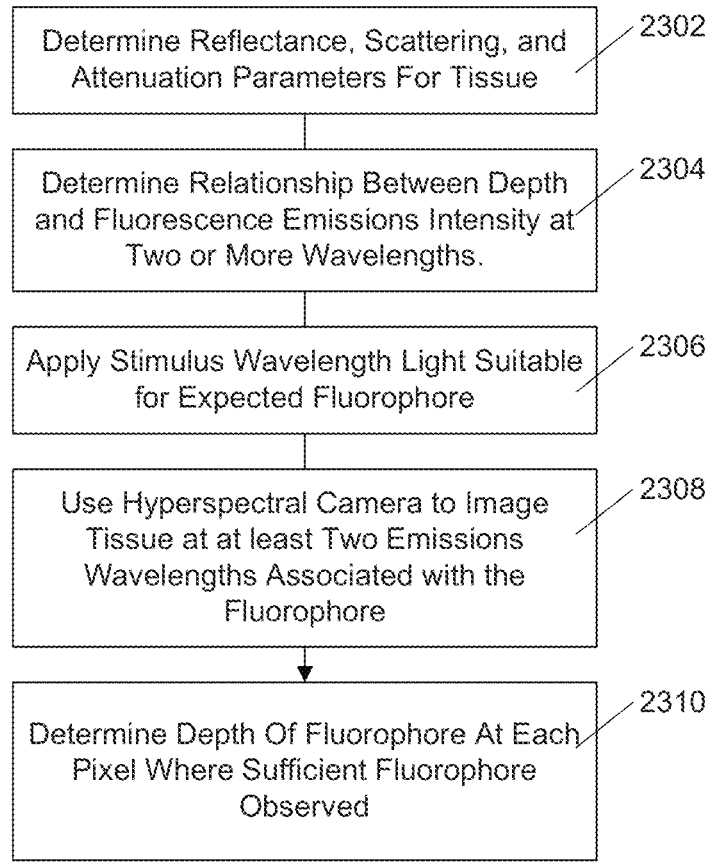
FIG. 23A is a flowchart illustrating fundamentals of both the model-based and non-model-based technique of depth-resolved fluorescent imaging.

All embodiments of depth-resolved imaging operate according to the basic flowchart of FIG. 23A. First, reflectance, scattering and absorption parameters are determined 2302 for tissue, in certain embodiments these parameters are determined by lookup in a table of parameters associated with tissue types, and in other certain embodiments by measurement of tissue using hyperspectral images taken under white light, and in particular using an image plane associated with emissions wavelengths of a fluorophore expected in the tissue. These parameters are used to determine 2304 a relationship between depth and a shift between observed emissions spectra and standard emissions spectra of the fluorophore; in embodiments using a table of parameters this will be a constant relationship for all pixels, in embodiments using measurement of tissue this may be a map of relationships of depth to spectral change that differ from pixel to pixel. While some embodiments use unstructured white light to determine these parameters, others use spatially modulated (also known as structured) light and determine a three dimensional map of scattering and absorption parameters in the tissue, allowing determination of accurate relationships between depth and spectra at each pixel.

Stimulus wavelength light is applied 2306 to the tissue, such that any of the expected fluorophore present is stimulated to fluoresce.

Measuring fluorescent emitted light at a at least a first and a second emission wavelengths associated with a fluorophore at each of a plurality of pixels; in embodiments this is accomplished by using the hyperspectral camera to record images 2308 at two, or more, emissions wavelengths associated with the fluorophore.

A depth of the fluorophore at each pixel is then determined 2310 based upon the at least the absorption parameters and differences in intensity of the fluorescent emitted light at the first and the second emissions wavelengths. In some particular embodiments, additional emission wavelengths are used. Depth is not determined for pixels without significant fluorescent emissions. The depth determination at each pixel is based upon the relationship between depth and the ratios, and the measured fluorescent emitted light.

In a particular embodiment, using the inclusion depth values at each pixel of the wide-field illumination area, a partial surface can be constructed, representing a partial topography of the tumor beneath the tissue surface. This involves thresholding the depth values at each pixel to eliminate points not in the inclusion, then using the remaining points as seeds to construct a triangular partial surface mesh. We then calculate the entire tumor geometry using a surface recreation algorithm described below:

1. Construct a 3D tetrahedral volume mesh representing the entire tissue domain interrogated. The tissue surface geometry obtained using spatially modulated illumination (see the Spatially Modulated Illumination subsection) is used as the surface of the domain, and a volume mesh is constructed based on this surface.

2. Project the illumination field onto the surface of the mesh based on directional movement orthogonal to the surface.

3. For each node in the tetrahedral mesh, cast a ray from the node to the nearest point in the illumination field.

4. If this ray intersects the partial surface of the tumor geometry, determine whether the point is in the tumor based on: (i) Surface coverage and (ii) Distance from the surface. Surface coverage is determined by creating a sphere around the point of intersection between the ray and the partial surface, then calculating the surface node density in that sphere relative to the node density outside the sphere. This represents the degree to which the surface is in front of the point of interest. Distance from the surface is a direct distance calculation between the point of intersection and the node position in the mesh. The importance of these two factors, surface coverage and distance from the surface, is determined based on user-defined weighting factors. If a point is has sufficient surface coverage, and small distance from the surface, it is included in the tumor geometry.

3D spectroscopic fluorescence tomographic reconstruction is then performed using the tetrahedral mesh created with tumor and background spatial information encoded in the mesh. Initial optical property values are used, determined as described in the Spatially Modulated Illumination section. Laplacian regularization is used for reconstruction, with nodes in the mesh weighted by their proximity to the recreated tumor geometry (4). This allows the spatial prior information to guide the reconstruction process without assuming that the tumor geometry is perfect. The multispectral fluorescence tomography reconstruction recovers the optical properties at each node in the mesh, in particular fluorophore concentration. The partial depth information obtained using spectroscopic measurements of fluorescence and diffuse reflectance allow us to disentangle the effects of tumor depth and fluorescence concentration, which previously inhibited quantitative fluorescence reconstruction.

The light modeling package NIRFAST is used for mesh creation and FEM-based modeling (5). However, a technique is being developed at Polytechnique based on Monte Carlo light transport simulations.

We develop and test wide-field methods to map subsurface fluorescence, first for (a) detection and depth determination (dFI) and for (b) PpIX (or other fluorophore) quantification at depth (qdFI). Here, 'depth' denotes distance below the surgical surface of the closest region of significant positive PpIX fluorescence ("sub-surface fluorescence topography"87). Our approach, both conceptually and practice is based on a combination of spectral and spatial constraints—although, here, the latter is critical to the separation of depth and PpIX concentration for qdFI, i.e., to distinguish accurately between weak fluorescence just below the surgical surface and stronger fluorescence at greater depth.

The resulting dFI topographic maps informs the surgeon whether PpIX-containing tissues (or other expected fluorophores) exist beyond the superficial layers of the exposed surgical surface where quantitative assessment is made with qFI. The qdFI enhancement generates a topographic map of the actual CPpIX at depths which could impact the decision to continue tumor resection in areas where, e.g., motor and/or cognitive functions can be compromised by excessive tissue removal. Absolute CPpIX can also inform the surgeon on biological properties such as proliferation and degree of invasiveness that add to the decision-making process.

A model-based dFI method, using a per-pixel map of absorbance and scattering parameters with per-pixel relationships of depth to emissions spectral shift is illustrated in FIG. 24.

In a non-modeled quantified fluorescence imaging alternative (FIG. 23) the reflectance hyperspectral imaging is used to retrieve optical properties maps (absorption and scattering) using, for example using a look-up table approach. For this case, the full spectrum is required so hyperspectral imaging of white-light excitation is thought to be a requirement because these properties differ with wavelength and affect propagation of fluorescent emitted light to the tissue surface. The optical properties thus obtained are required for model-based qFI & dFI as well as qdFI.

Operation in Quantitative Depth-Resolved Imaging (qdFI) Mode

Figure 14:
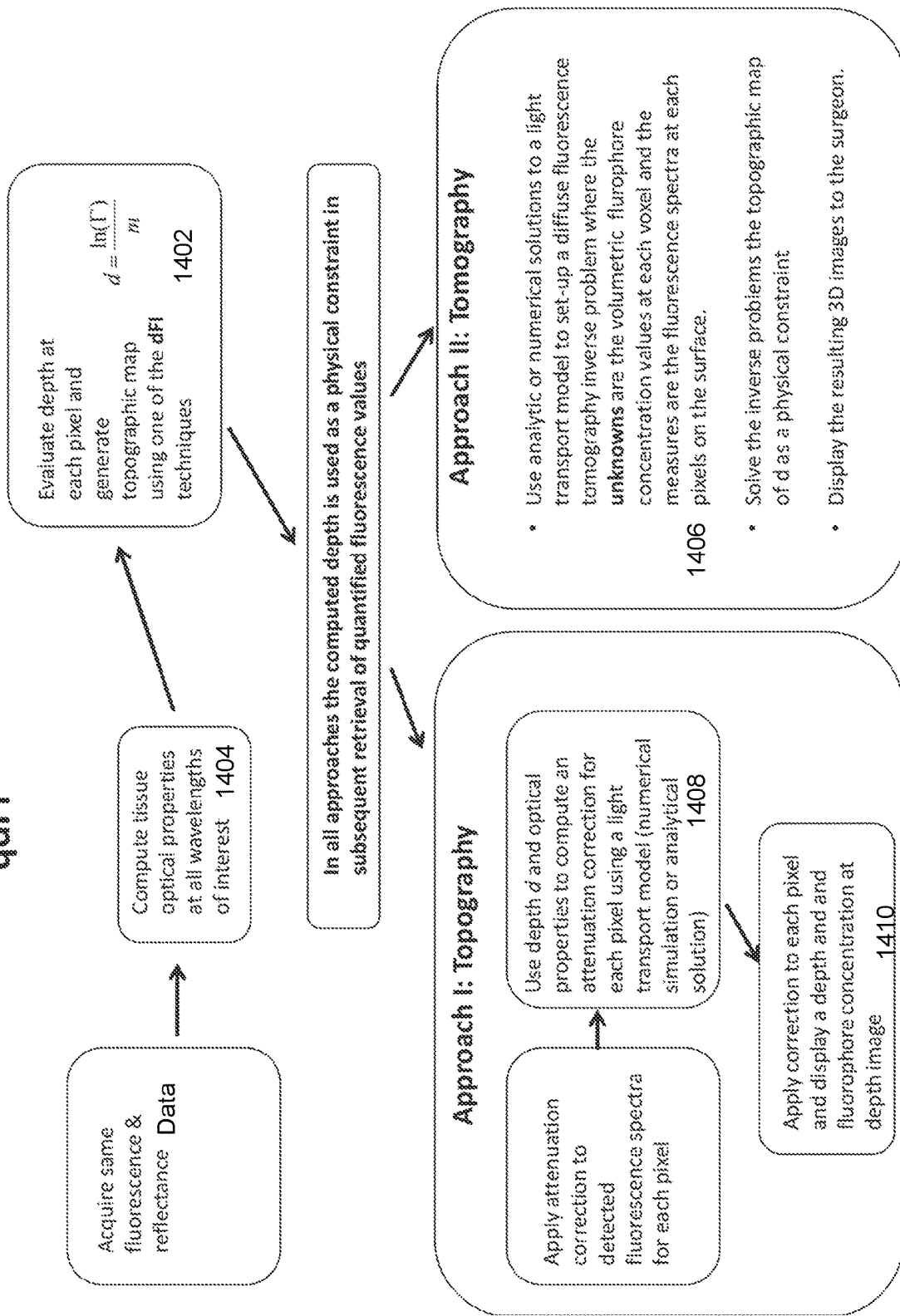
FIG. 14 is a data flow diagram representing a quantitative, depth-resolved, fluorescent imaging.

Data-flow diagram D3, as illustrated in FIG. 14, may prove helpful in understanding qdFI mode. qdFI processing follows depth determination performed 1402 according to the methods previously discussed with reference to dFI mode and FIGS. 15, 23, and 24. Reflectance parameters are determined for the tissue at stimulus wavelength, and scattering and absorbance parameters are determined for both stimulus and emissions wavelengths 1404; this is a superset of the tissue optical parameters used for the dFI mode processing. These parameters are then used to correct the fluorescent emissions intensities by either fitting fluorophore intensity in a light transport model 1406 of tissue to observed fluorescent emissions images, or by determining 1408 an attenuation correction as an inverse of a total of reflectance at stimulus wavelength and total attenuation at both stimulus and emissions wavelengths between the tissue surface and the determined fluorophore depth, and applying 1410 the correction factors.

We have demonstrated that (a) multi-wavelength excitation (400-600 nm) with integration of the fluorescence signal over all emission wavelengths and (b) spectrally-resolved detection following excitation at ~633 nm85 allow subsurface PpIX topography—the first is very accurate (±0.5 mm) to a depth up to 3 mm in brain, while the latter is less accurate (>±1 mm) but can reach depths of 10 mm or more in brain, and potentially deeper in other tissues. Thus, we optimize the wavelength combinations for excitation and fluorescence detection to meet our performance targets. For the former, we illuminate at five predetermined wavelengths between 400 and 635 nm to match the PpIX absorption peaks, and obtain hyperspectral corresponding images of fluorescence as described in the section entitled Operation in Fluorescent Imaging Mode above.

Preliminary data collected with a prototype hyperspectral imaging system where PpIX capsules are immersed in a tissue-simulating phantom were imaged and their spectra detected at depths up to 9 mm Because light is attenuated by 2 orders of magnitude for each cm of depth, the fluorescence signals in dFI are smaller than their qFI surface counterparts. Following wavelength optimization, a new dFI multispectral-detection module based on a cooled CCD camera is provided in some embodiments for improved noise and sensitivity during surgery.

Spectra at each pixel are determined from the hyperspectral images, and a depth estimated from a phantom-fitted equation as illustrated in FIG. 16. Once a depth is estimated, this depth is displayable to a user as an image having brightness representing a quantified fluorescence with a color representing depth.

Since optical properties of tissue are determined at multiple depths and at multiple wavelengths from the hyperspectral image stacks captured under spatially-modulated white light, these properties are used to correct received fluorescence spectra for tissue properties. The corrected received light at two or more wavelengths is then used to determine fluorophore ratios to estimate depth to retrieve the topographic maps and quantify fluorophore concentrations. There is also sufficient information available to deconvolved contributions to the captured spectra from two or more distinct fluorophores, permitting quantitative depth resolved fluorescent imaging of two or more fluorophores simultaneously; providing more information about tissue type than available when using only a single fluorophore.

A strategy analogous to qFI is pursued based on two approaches: (1) techniques using normalization with spectrally-resolved wide-field reflectance images and (2) methods based on accurate light transport modeling in tissue. The dFI algorithms are developed for spectrally-resolved data (both excitation and emission fluorescence), while the qdFI algorithms combine spectral and spatially-modulated data to allow both depth and CPpIX at depth to be retrieved.

Normalization techniques: Since distortion of the measured fluorescence is due to absorption features in the reflectance spectra, quantifying these elements in the wide-field spectrally-resolved reflectance images allows PpIX depth to be deconvolved from the measured fluorescence images. This is validated in phantoms from which empirical correction algorithms are derived. The technique is likely less robust than a full model-based approach (below), but reduces complexity.

Model-based methods: For qdFI (and likely maximally-accurate dFI) the light transport Diffusion Theory/Monte Carlo hybrid model is used. Solutions providing the best fit to the surgical data will be processed into a 2D topographic depth image (dFI) and a CPpIX image at depth (qdFI). Two critical inputs are required for these simulations: (a) tissue optical properties as determined using spatially modulated light as described above, and (b) 3D profile of the surgical bed as determined by stereovision techniques described above. For dFI and qdFI, absorption and scattering properties averaged over the volume of tissue between the surface and the tumor are more appropriate, although the requirement is mitigated by the relative homogeneity of brain tissue on the length scales considered here (1-10 mm) If necessary, depth-resolved maps of tissue optical properties are generated by varying the spatial frequencies and phases in the spatially-modulated excitation light method.

In order to validate the method, we fabricated tissue phantoms with different geometries (including simulated resected cavities of different curvature) and use them to evaluate conditions in which the depth accuracy falls below the threshold of ±0.5 mm for depths up to 3 mm and 1 mm for larger depths. In vivo studies will also proceed including experiments where (i) depth of tumor implantation will be varied between cohorts of animals and (ii) immediately after in vivo measurements and sacrifice, whole brains will be removed, and either sectioned for PpIX confocal fluorescence microscopy to map the subsurface tumor depth (with adjacent-section histopathologic confirmation) or dissected to remove tissue fragments for quantitative fluorometry.

Preliminary data already exist that strongly support the technical feasibility of qFI, dFI and qdFI.

Operation in Depth-Resolved Fluorescent Imaging Mode with Tomographic Display In an embodiment, surface profiles as determined from stereoscopic imaging as described above are entered into a three-dimensional model of the tissue by three-dimensional modeling routines in memory 178. Depth information as determined in the section entitled Operation in Quantitative Depth-Resolved Imaging qdFI Mode above is then entered into the three dimensional model of the tissue by marking voxels corresponding to the estimated depth of fluorophore.

The three-dimensional model is then sliced and displayed to the surgeon as a sequence of tomographic images.

Operation with Automatic Tissue Classification

The optical properties of tissue at each pixel as determined in Operation in Spatial-Frequency-Modulated Reflectance Mode, the hemoglobin, oxyhemoglobin, and deoxyhemoglobin concentrations as determined above under Operation in Hyperspectral Reflectance Imaging Mode, the surface fluorophore concentrations as determined by qFI as describe above, the depth and quantity-at-depth information as determined in the section entitled Operation in Quantitative Depth-Resolved Imaging qDFI Mode above for each pixel are all provided to a trainable classifier such as a neural network classifier, kNN classifier, or in an alternative embodiment an SVM classifier; the classifier is implemented as classification routines in memory 178 and executed on the processor. The classifier is trained to provide a classification indicative of a probability that tumor exists at a location in tissue corresponding to that pixel. Classification results for each pixel are entered into a tissue classification map that is then displayed to the surgeon.

Alternative Optical Systems

Figure 17:
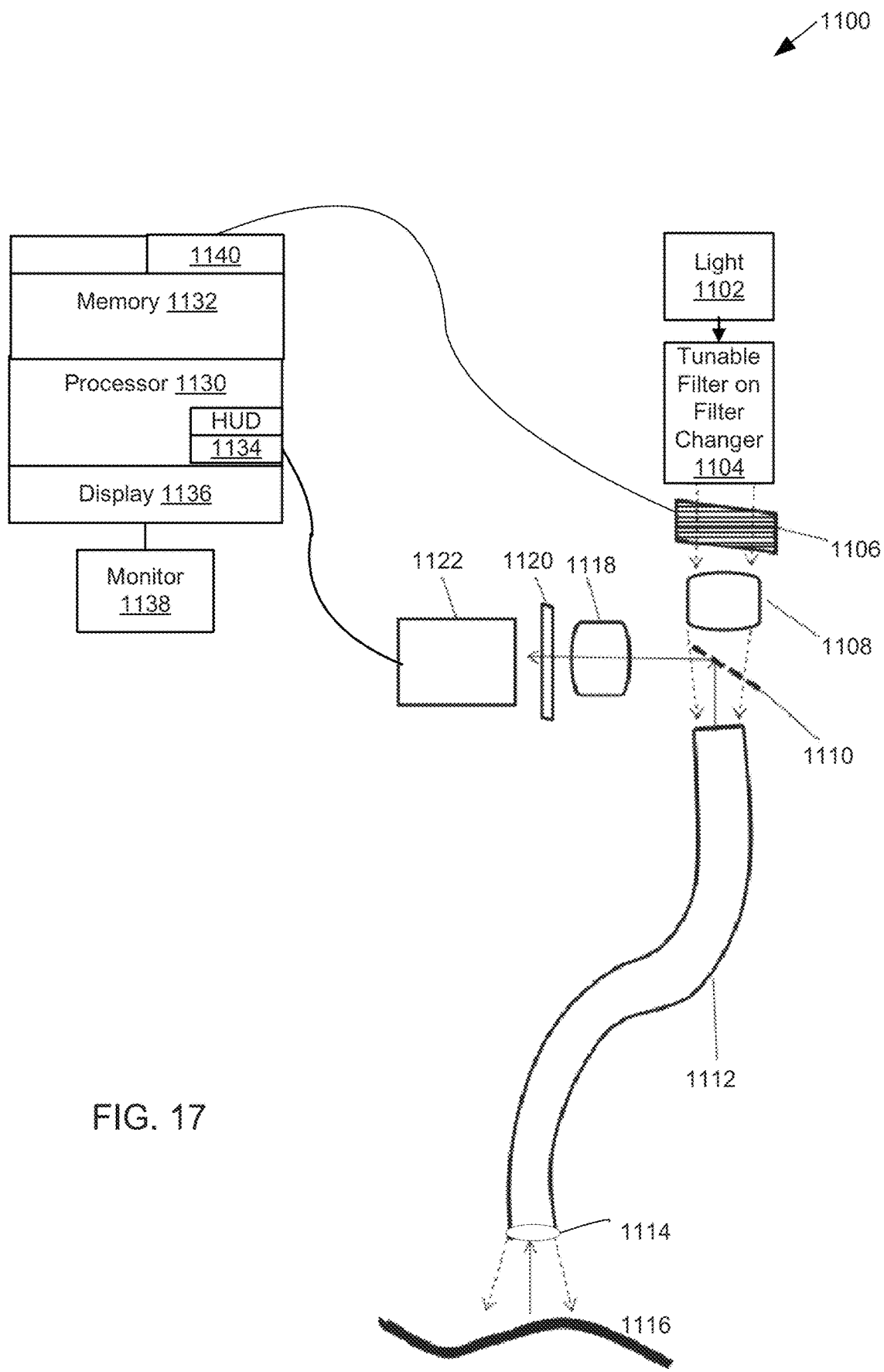
FIG. 17 is a block diagram of a first endoscopic embodiment.

An endoscopic system embodying many of the features and operating modes herein described is illustrated in FIG. 17. In the endoscope of FIG. 17, a supercontinuum laser 1102, or similar white light source, is coupled to pass light through a filter changer 1104 that is equipped with a clear filter and a tunable optical bandpass filter, the filter tunable from 400 to over 700 nanometer wavelengths with a bandpass as above described. Light from filter-changer 1104, which may be filtered light, passes through a spatial modulator 1106, such as a modulator based on a digital micromirror device where it is patterned. Light from the spatial modulator passes through a projection lens 1108 and a beam-splitter 1110 onto a proximal end of a coherent fiber bundle 1112 that runs through the endoscope. In an endoscopic embodiment, images of tissue as illuminated by spatially modulated light are processed to determine a surface profile, since endoscopes typically do not have stereo cameras 120, 122. At a second, or tissue, end of the coherent fiber bundle the patterned light passes through a tissue-viewing lens 1114 onto tissue 1116. Light from tissue 1116 is imaged through lens 1114 and passes onto the tissue end of bundle 1112, and is emitted from proximal end of bundle 1112 onto beam-splitter 1110, where it is diverted through viewing lens 1118 and an optional filter 1120 into hyperspectral camera 1122 that corresponds to hyperspectral camera 128 and may have any of the forms previously described with reference to hyperspectral camera 128. Signals derived by hyperspectral camera 128 from the light from tissue 1116 pass through camera interface 1134 and captured images are processed by processor 1130 configured with routines in memory 1132, the routines having machine readable instructions for performing hyperspectral reflectance imaging, spatially modulated reflectance imaging, fluorescent imaging (including multiple-fluorophore fluorescent imaging), quantitative fluorescent imaging, and depth-resolved fluorescent imaging. Processed images are presented to the surgeon by processor 1130 through display adapter 1136 on monitor 1138. The spatial modulator 1106 operates under control of a display adapter 1140 under control of processor 1130. Since only one image is available, 3-dimensional surface extraction is not possible and non-modeled versions of fluorescent depth resolution are used in the routines in memory 1132, such as that described in the draft article attached hereto and entitled A Non-Model Based Optical Imaging Technique For Wide-Field Estimation Of Fluorescence Depth In Turbid Media Using Spectral Distortion.

In use, surgical tools inserted through a lumen of the endoscope of the embodiment of FIG. 17 may be used by a surgeon to perform surgery, such as excision of polyps in a large intestine of a subject, under observation through images on monitor 1138.

Figure 18:
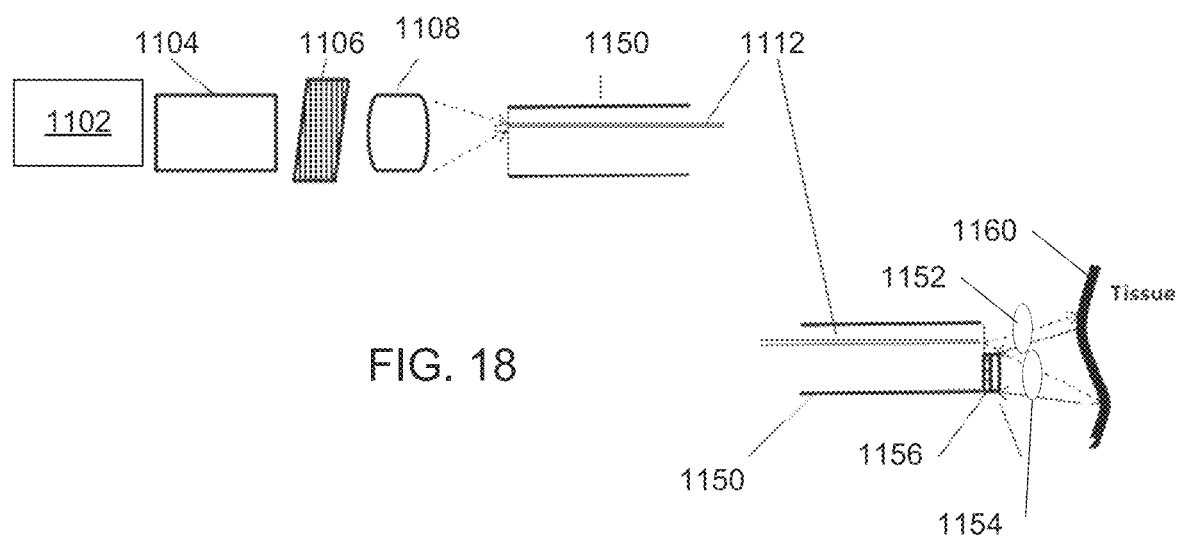
FIG. 18 is a block diagram of a second endoscopic embodiment.

In an alternative endoscopic embodiment, illustrated in FIG. 18, a light source 1102, filter-changer 1104, spatial modulator 1106, and lens 1108 are provided that provide light to a proximal end of coherent fiber bundle 1112 in an endoscope 1150. At tissue end of bundle 1112 and a part of endoscope 1150 are an illumination projection lens 1152 that projects light from bundle 1112 onto tissue 1160, and an imaging lens 1154 that focus light from tissue 1160 on a hyperspectral imager 1156. Hyperspectral imager 1156 is an integrated multiple-filter imaging device similar to that previously discussed with reference to imaging device 199.

Alternatives

In a simplified dFI embodiment lacking spatial modulation capability, a library of typical light scattering and absorption parameters for tissues of different types at fluorescent imaging wavelengths is included in memory 178, 1132. In this embodiment, an operator selects a predominant surface tissue type from entries in the library; the associated scattering and absorption parameters from the library are then used instead of parameters determined by measuring tissue to determine relationships of depth to spectral shift with fluorophore depth.

It is expected that the system and methods disclosed herein are applicable to three-dimensional quantitative mapping autofluorescence of nicotine-adenine-dinucleotide (NAD) in tissue, and for three-dimensional quantitative mapping autofluorescence of activated calcium channels in tissue in real time. Since calcium channels are physiologically important in both cardiac muscle tissue and central nervous tissue, realtime quantitative maps of calcium channels are potentially useful in both cardiac surgery and neurosurgery.

It is also expected that the present system can image concentrations of two or more fluorophores, using spectral information in the hyperspectral image stack to deconvolve contributions of each of several fluorophores and thereby provide images representing each fluorophore separately. This permits displaying concentrations of intrinsic fluorophores PpIX and NAD, or concentrations of two targeted agents having different fluorescent emissions spectra, separately to a surgeon and thereby permit better discrimination of healthy and diseased tissues.

Figure 1F:
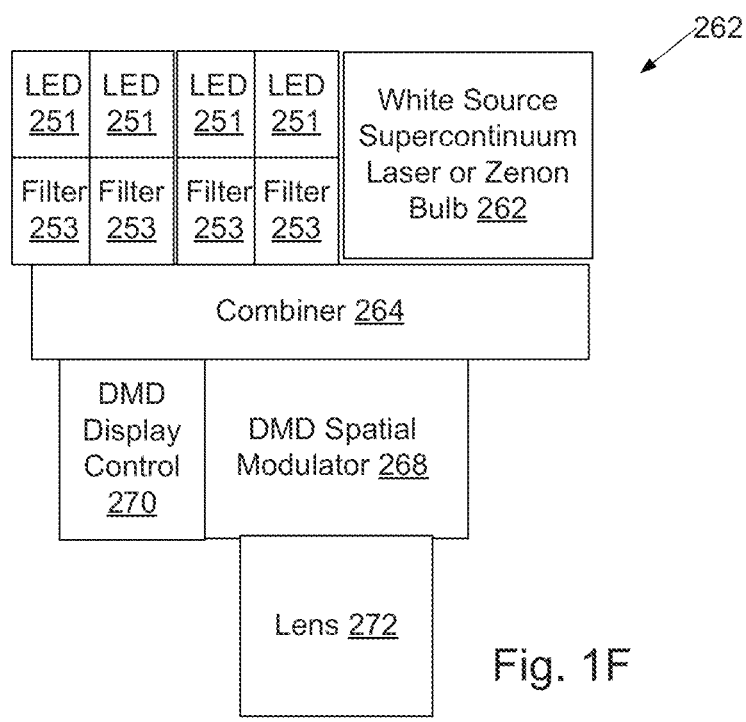
FIG. 1F illustrates a light source having white and fluorescent stimulus wavelength capability as both a spatially modulated and unmodulated light source.
Figure 1G:
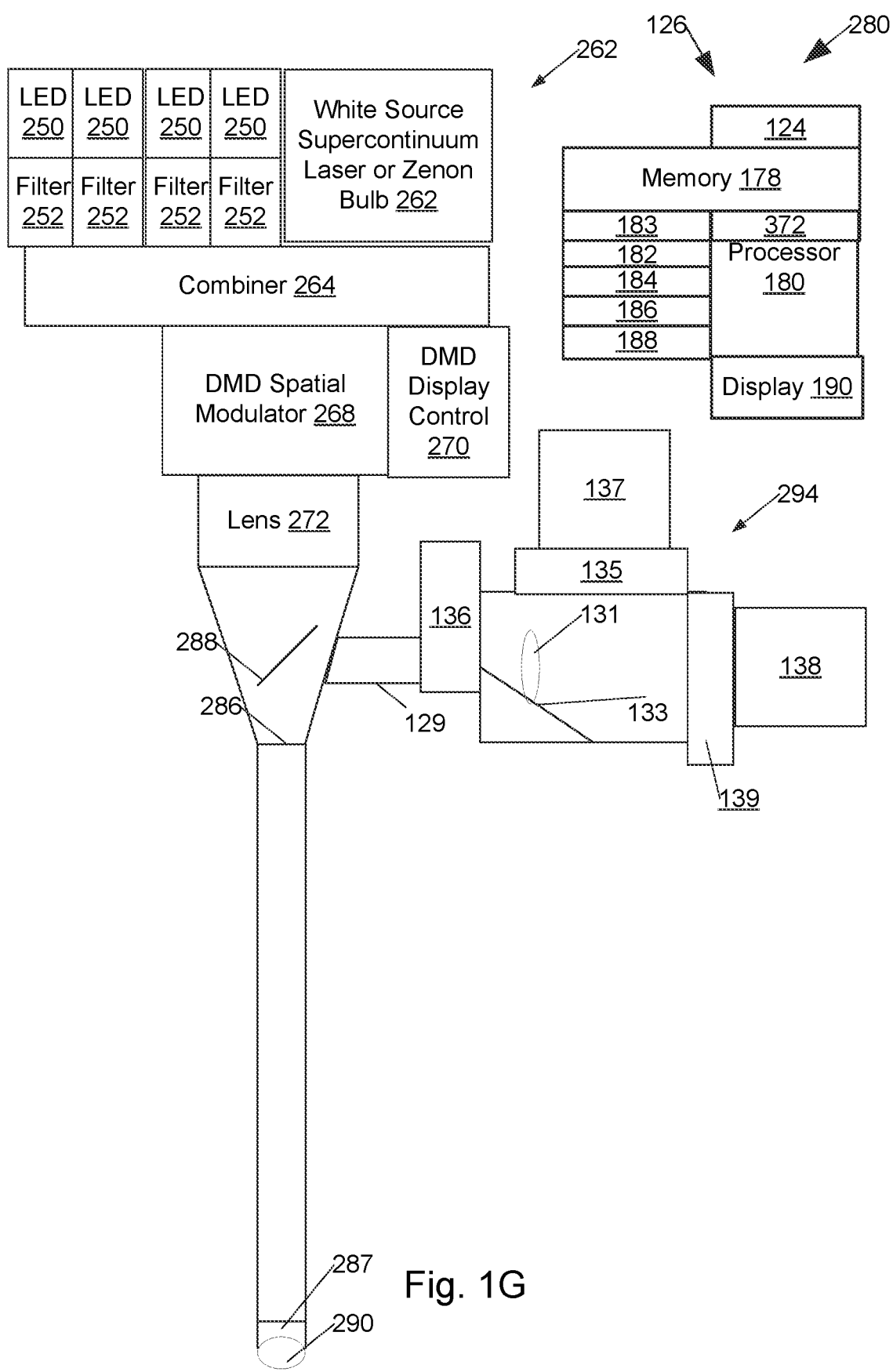
FIG. 1G illustrates an imaging system adapted for use in laparoscopic surgery.

In an alternative implementation intended for use in open surgery, a camera system 2502, including fluorescent stimulus illuminators and structured light illuminators as discussed with reference to FIG. 1C, 1D, or 1F, at least one hyperspectral camera as discussed with reference to FIG. 1, 1A, or 1B, and at least one additional camera to support stereovision which in a particular embodiment is a second hyperspectral camera, are located in view of a surgical site 2506 of a subject 2508. Camera system 2502 provides stereo images to an image processor 2504 like that previously discussed with reference to image processing system 126, and which performs stereo surface extraction, as well as hyperspectral image processing for heme oxygenation and surface and subsurface mapping of fluorescent agents, as heretofore described. Camera system 2502 may be ceiling mounted, or mounted on a movable stand permitting relocation within an operating room; if camera system 2502 is mounted on a movable stand it is equipped with tracking transponders 2512.

In addition to being coupled to display images on monitor 2510, image processor 2504 is coupled to display images on a head-mounted display 2513 that is equipped with tracking transponders 2514 sufficient to determine both viewing angle and position of head-mounted display 2513. Head-mounted display 2513 is adapted to be worn by, and in front of eyes of, a surgeon, not shown; head-mounted display 2513 is configured with a beamsplitting mirror 2515 that permits superposition of displayed images into a visual field of the surgeon. A tracking subsystem 2516, similar to the tracker 142 previously discussed, is provided to determine positions and angles of head mounted display 2513, and camera system 2502, In this embodiment, image processor 2504 is configured to construct a three-dimensional computer model of a surface of the surgical site 2506, and to annotate this model with information determined through hyperspectral imaging, such as maps of heme oxygenation and ischemia, maps of inflammation biomarkers, maps of fluorescent emissions from autofluorescent biomarkers such as PpIX or NAD, and quantified and depth-resolved maps of fluorophore concentrations as determined by qFI, dFI, and qdFI imaging as described above. The image processor then renders the annotated model into an image representing the surgical site 2506 (with annotations) as viewed from a tracked location of the head-mounted display 2513, so that images displayed through head-mounted display 2513 portray the information derived from hyperspectral imaging superimposed on the surgeon's direct view of the surgical site, in doing so the image processor also renders and displays the partial surface model of depth-resolved fluorophore concentrations determined as described in the Depth-Resolved Fluorescent Imaging (dFI) section above.

Figure 25:
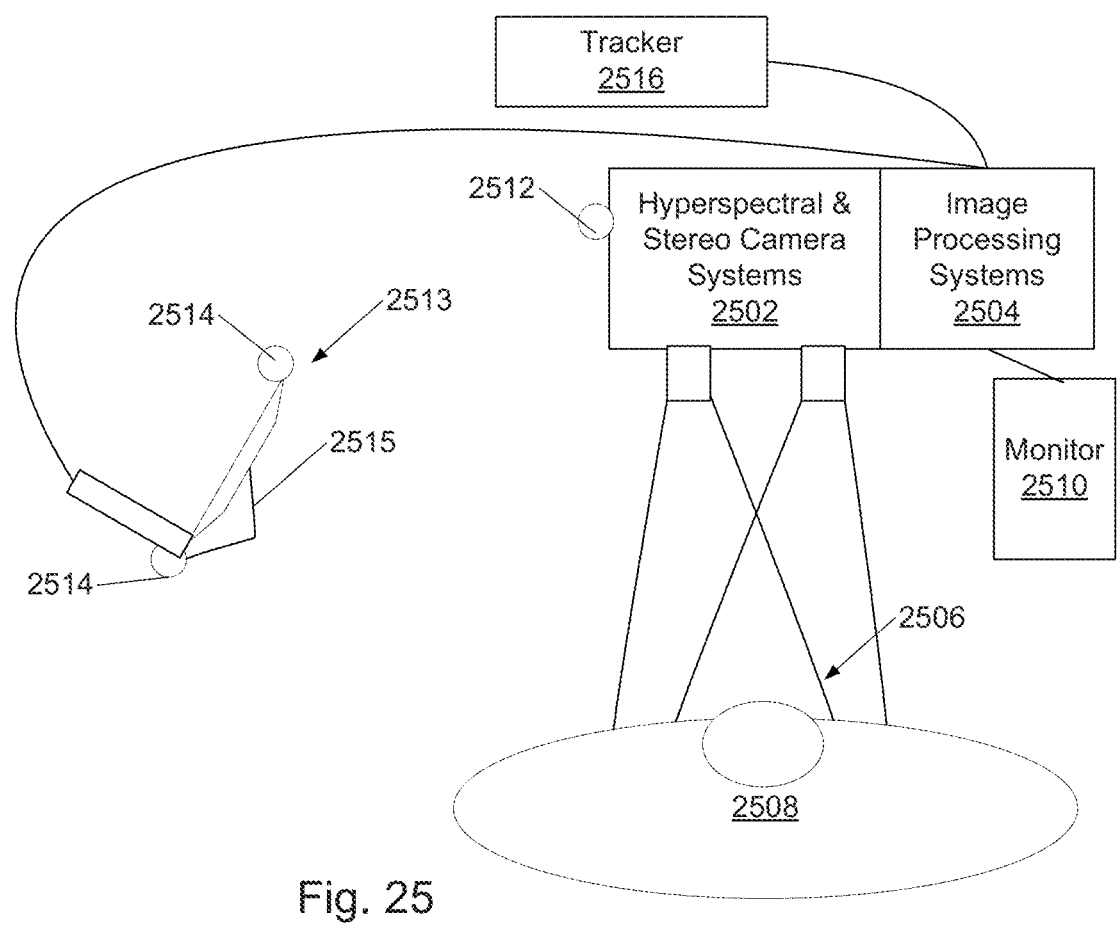
FIG. 25 is a block diagram of a fluorescent depth-resolved and hyperspectral imaging system adapted to provide images through a head-mounted display system.

It is believed that the embodiment of FIG. 25, when displaying information derived by hyperspectral imaging such ischemia and as heme oxygenation, will be helpful to surgeons performing open-heart procedures intended to relieve ischemia. The embodiment is also expected to be useful when imaging fluorophore concentrations for a wide variety of cancer surgeries, and for assessing tissue viability during tissue debridement and diabetic amputation surgeries.

Combinations

It is anticipated that any one of the fluorescent stimulus light sources herein discussed with reference to FIG. 1C, 1D, or 1F may be combined with any one of the hyperspectral cameras discussed with reference to FIG. 1A or 1B, or with a camera having a single wideband photodetector and tunable filter into a hyperspectral imaging system and coupled to the digital image processing system described herein to form a system adapted for use in quantitative and depth resolved fluorescent imaging. Various combinations will, however, have differing resolution and accuracy of depth determination and quantification.

Further, it is anticipated that the following specific combinations of features will prove functional:

An optical and image processing system designated A including a fluorescent stimulus light source adapted to provide light at a fluorescent stimulus wavelength; a spatial modulator coupled to modulate light forming spatially modulated light; projection apparatus configured to project onto tissue light selected from the group consisting of fluorescent stimulus light and spatially modulated light; a hyperspectral camera configured to receive light from tissue; and an image processing system coupled to receive images from the hyperspectral camera and configured with a memory containing machine readable instructions for performing at least one function selected from the group consisting of quantitative fluorescent imaging, and depth resolved fluorescent imaging and for displaying resultant processed fluorescent images.

An optical and image processing system designated AA incorporating the system designated A wherein the function comprises depth resolved fluorescent imaging, and wherein the machine readable instructions include instructions for determining a relationship between depth and ratios of intensity at a first and a second emissions wavelength for a fluorophore in tissue; applying stimulus wavelength light; measuring fluorescent emitted light at a at least the first and the second emission wavelengths associated with the fluorophore at each of a plurality of pixels; determining a depth of the fluorophore at each pixel based upon the relationship between depth and the ratios, and the measured fluorescent emitted light.

An optical and image processing system designated AB incorporating the system designated A or AA wherein the relationship between depth and ratios of intensity at the first and the second emissions wavelength are determined from images of the tissue.

An optical and image processing system designated AC incorporating the system designated A, AA, or AB wherein the relationship between depth and ratios of intensity at the first and the second emissions wavelength is determined on a per-pixel basis from the images of the tissue.

An optical and image processing system designated AD incorporating the system designated A, AA, or AB wherein the relationship between depth and ratios of intensity is determined from values in a library of tissue types.

An optical and image processing system designated AE incorporating the system designated A, AA, AB, AC, or AD wherein the function include quantitative fluorescent imaging, and wherein the machine readable instructions include instructions for: determining reflectance and absorbance parameters at each pixel of an image at a stimulus wavelength; and using the reflectance and absorbance parameters to correct fluorescence emission images.

An optical and image processing system designated AE incorporating the system designated A, AA, AB, AC, or AD wherein the machine readable instructions include instructions for providing spatially modulated light when obtaining images from which the reflectance and absorbance parameters are determined.

An optical and image processing system designated AF incorporating the system designated A, AA, AB, AC, AD, or AE, wherein there are at least two cameras adapted to capture digital stereo images and the machine readable instructions further comprise instructions for extracting a surface profile from the stereo images.

An optical and image processing system designated AG including the system designated AF, wherein the machine readable instructions further comprise instructions for determining an intraoperative location of structures located in preoperative medical images, and for displaying the determined intraoperative location.

An optical and image processing system designated AH including the system designated AG and wherein the machine readable instructions further comprise instructions for displaying the determined intraoperative location with the processed fluorescent images.

An optical and image processing system designated AI including the system designated AG or AH and wherein the machine readable instructions further comprise instructions for extracting a surface profile from depth-resolved fluorescent images.

An optical and image processing system designated AI including the system designated AG, AH, or AI further comprising a tracking subsystem adapted to determine a location and viewing angle of a display and wherein the machine readable instructions further comprise instructions for displaying rendered information selected from the group consisting of depth-resolved fluorescent images and intraoperative locations of structures as viewed from the determined location and viewing angle.

Conclusion

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

We claim:

1. An optical and image processing system comprising:
a light source adapted to provide, in a first mode, light at a fluorescent stimulus wavelength;
a spatial modulator coupled to modulate light from the light source, forming spatially modulated fluorescent stimulus light, the spatial modulator configured to provide a plurality of different spatial light modulation patterns comprising light at the fluorescent stimulus wavelength, the spatial light modulation patterns each characterized by a spatial frequency;
projection apparatus configured to project onto tissue the spatially modulated fluorescent stimulus light, the tissue being illuminated with the plurality of different spatial light modulation patterns at the fluorescent stimulus wavelength, each spatial light pattern providing light varying in intensity across the tissue according to the spatial frequency;
a hyperspectral camera configured to receive light from the tissue and generate images therefrom; and
an image processing system coupled to the hyperspectral camera and configured with a memory containing machine readable instructions for performing depth resolved, fluorescent imaging by driving the spatial modulator to provide at least a first and a second predetermined spatial-light modulation pattern of the plurality of different spatial light modulation patterns, receiving first images generated by the hyperspectral camera at the fluorescent stimulus wavelength, at least one second image at a first fluorescent emissions wavelength while the tissue is illuminated with light of the fluorescent stimulus wavelength, and at least one third image at a second fluorescent emissions wavelength different from the first fluorescent emissions wavelength while the tissue is illuminated with the light of the fluorescent stimulus wavelength, for processing the received first, second, and third images generated by the hyperspectral camera to generate processed fluorescent images, and for displaying the processed fluorescent images;
wherein the first predetermined spatial light modulation pattern has a same spatial frequency as the second predetermined spatial light modulation pattern, and wherein the first predetermined spatial modulation pattern has spatial phase different from a spatial phase of the second predetermined spatial modulation pattern;
wherein the machine readable instructions for generating the processed fluorescent images comprise instructions for:
determining a relationship between depth and ratios of intensity in the second and third images for a fluorophore in tissue from images of the tissue as illuminated with the plurality of different spatial light modulation patterns;
applying stimulus wavelength light; and
determining a depth of the fluorophore at each pixel based upon the relationship between depth and the ratios of intensity in the second and third images;
where the hyperspectral camera is adapted to pass light received from the tissue through a filter device selected from the group consisting of a tiling pattern of optical filters on photosensors of an image sensor, the tiling pattern of optical filters comprising filters of at least 13 distinct wavelength bands between 400 nanometers and 1000 nanometers, and a tunable filter.

2. The system of claim 1 wherein the relationship between depth and ratios of intensity at the first and the second fluorescent emissions wavelength is determined on a per-pixel basis from the images of the tissue.

3. The system of claim 2 wherein the machine readable instructions further comprise instructions for determining optical properties of tissue, the optical properties of tissue including at least absorbance, and for correcting depth-resolved fluorescent images for the absorbance to provide images of absolute fluorophore concentration.

4. The system of claim 3 wherein the optical properties of tissue are determined at each voxel of a three-dimensional voxel-based model, and the three-dimensional voxel-based model is used in constructing the images of absolute fluorophore concentration.

5. The system of claim 1 wherein the light source is adapted to operate in a second mode providing light at fluorescent emissions wavelength and wherein the machine readable instructions for determining optical properties of tissue comprise instructions for:
determining reflectance and absorbance parameters at each pixel of an image at the fluorescent stimulus wavelength from the received first images, and determining absorbance parameters at each pixel of the image at the emissions wavelength from received images obtained while the light source is operated in the second mode and the tissue is illuminated with a plurality of spatial light patterns; and
using the reflectance and absorbance parameters at stimulus wavelength and the absorbance parameters at the emissions wavelength to correct the processed fluorescent images.

6. The system of claim 5 wherein the machine readable instructions include instructions for providing spatially modulated light when obtaining images from which the reflectance and absorbance parameters at stimulus and emissions wavelengths are determined.

7. An optical and image processing system of claim 6 wherein there are at least two cameras adapted to capture digital stereo images and the machine readable instructions further comprise instructions for extracting a surface profile from the stereo images.

8. An optical and image processing system of claim 7, wherein the machine readable instructions further comprise instructions for determining an intraoperative location of structures located in preoperative medical images, and for displaying the determined intraoperative location.

9. An optical and image processing system of claim 8 wherein the machine readable instructions further comprise instructions for displaying the determined intraoperative location with the processed fluorescent images.

10. An optical and image processing system of claim 7, wherein the machine readable instructions further comprise instructions for extracting a surface profile from depth-resolved fluorescent images.

11. An optical and image processing system of claim 7, further comprising a tracking subsystem adapted to determine a location and viewing angle of a display and wherein the machine readable instructions further comprise instructions for displaying rendered information selected from the group consisting of depth-resolved fluorescent images and intraoperative locations of structures as viewed from the determined location and viewing angle.

12. The system of claim 1 where the light source further comprises a broadband illumination source coupled to provide light through a tunable filter having a passband at the fluorescent stimulus wavelength, light from the tunable filter being provided to the spatial modulator; and wherein the spatial modulator and projection apparatus is configurable to illuminate the tissue with the spatial light pattern in three different spatial phases.

13. The system of claim 1 where the hyperspectral camera is a wavelength-selective camera
where the light from the tissue passes through the tunable filter before reaching an imager.

14. The system of claim 1 wherein, during processing to generate the processed fluorescent images, the image processing system is configured to determine scattering and absorption parameters of the tissue at voxels of a three-dimensional model of the tissue and to use the scattering and absorption parameters to correct fluorescent emissions received from the hyperspectral camera at the fluorescent emissions wavelength.

15. An optical and image processing system comprising:
a light source adapted to provide, in a first mode, light at a fluorescent stimulus wavelength;
a spatial modulator coupled to modulate light from the light source, forming spatially modulated fluorescent stimulus light, the spatial modulator configured to provide a plurality of different spatial light modulation patterns comprising light at the fluorescent stimulus wavelength, the spatial light modulation patterns each characterized by a spatial frequency;
projection apparatus configured to project onto tissue the spatially modulated fluorescent stimulus light, the tissue being illuminated with the plurality of different spatial light modulation patterns at the fluorescent stimulus wavelength, each spatial light pattern providing light varying in intensity across the tissue according to the spatial frequency;
a hyperspectral camera configured to receive light from the tissue and generate images therefrom; and
an image processing system coupled to the hyperspectral camera and configured with a memory containing machine readable instructions for performing depth resolved, fluorescent imaging by driving the spatial modulator to provide at least a first and a second predetermined spatial-light modulation pattern of the plurality of different spatial light modulation patterns, receiving first images generated by the hyperspectral camera at the fluorescent stimulus wavelength, at least one second image at a first fluorescent emissions wavelength, and at least one third image at a second fluorescent emissions wavelength, for processing the received first, second, and third images generated by the hyperspectral camera to generate processed fluorescent images, and for displaying the processed fluorescent images;
wherein the first predetermined spatial light modulation pattern has a same spatial frequency as the second predetermined spatial light modulation pattern, and wherein the first predetermined spatial modulation pattern has spatial phase different from a spatial phase of the second predetermined spatial modulation pattern;
determining a relationship between depth and ratios of intensity in the second and third images for a fluorophore in tissue;
applying stimulus wavelength light;
determining a depth of the fluorophore at each pixel based upon the relationship between depth and the ratios of intensity in the second and third images; and
wherein the relationship between depth and ratios of intensity at the first and the second fluorescent emissions wavelengths are determined from images of the tissue;
wherein the machine readable instructions further comprise instructions for determining optical properties of tissue, the optical properties of tissue including at least absorbance, and for correcting depth-resolved fluorescent images for the absorbance to provide images of absolute fluorophore concentration;
wherein the optical properties of tissue are determined at each voxel of a three-dimensional voxel-based model, and the three-dimensional voxel-based model is used in constructing the images of absolute fluorophore concentration; and
wherein fluorophore concentration parameters of the three-dimensional voxel-based model are fit to at least the obtained second and third images, the fitting including simulating the three-dimensional voxel-based model using Monte Carlo based modeling of near-surface voxels and diffusion-based modeling of deep voxels.

* * * * *